US005786168A

United States Patent [19]
Ishizaka et al.

[11] Patent Number: 5,786,168
[45] Date of Patent: Jul. 28, 1998

[54] METHOD FOR RECOMBINANT PRODUCTION OF ANTIGEN NON-SPECIFIC GLYCOSYLATION INHIBITING FACTOR (GIF)

[75] Inventors: Kimishige Ishizaka, La Jolla; Yun-Cai Liu, San Diego, both of Calif.; Toshifumi Mikayama, Gunma-machi, Japan

[73] Assignees: Kirin Beer Kabushiki Kaisha, Tokyo, Japan; La Jolla Institute for Allergy and Immunology, San Jose, Calif.

[21] Appl. No.: 455,633

[22] Filed: May 31, 1995

Related U.S. Application Data

[63] Continuation of Ser. No. 61,041, filed as PCT/US92/04614 Jun. 3, 1992, abandoned, which is a continuation-in-part of Ser. No. 709,375, Jun. 3, 1991, abandoned, which is a continuation-in-part of Ser. No. 533,889, Jun. 4, 1990, abandoned.

[51] Int. Cl.[6] .............................. C12P 21/02; C07H 21/04

[52] U.S. Cl. .................... 435/69.1; 435/69.7; 435/252.3; 435/320.1; 530/307; 530/395; 530/397; 530/412; 530/413; 536/23.1; 536/23.4; 536/23.5

[58] Field of Search ................................ 435/69.1, 252.3, 435/320.1, 69.7; 530/395, 397, 412, 413, 307; 536/23.1, 23.5, 23.4

[56] References Cited

U.S. PATENT DOCUMENTS 4,843,004 6/1989 Platsoucas .
4,946,788 8/1990 Delespesse .

FOREIGN PATENT DOCUMENTS

WO9011301 10/1990 WIPO .
WO9219727 11/1992 WIPO .

OTHER PUBLICATIONS

Bowie J U; Reidhaar-Olson J F; Lim W A; Sauer R T. Deciphering the message in proteinsequences: tolerance to amino acid substitutions. Science, (1990 Mar. 16) 247 (4948) 1306–10.

Lindley et al. (1987) FEBS Lett. vol. 226, pp. 96–100.

Tagaya et al. (Oct., 1991), PNAS. vol. 88, pp. 9117–9121.

Ban, (1991), Cell, vol. 66, pp. 1–3.

Tagaya, et al.,*Molecular Cloning of a cDNA that Encodes Glycosylation Inhibiting Factor (GIF) Recognized by Anti–Lipomodulin Antibody*, Cytokine Biochemistry and Biology (1232), (Apr. 1992).

Thomas, et al., *Glycosylation–Inhibiting Factor From Human T Cell Hybridomas Constructed from Pepipheral Blood Lymphocytes of a Bee Venom–Sensitive Allergic Patient*, The Journal of Immunology, vol. 148, 729–737, No. 3, Feb. 1, 1992.

Kenji Katamura, et al.; Biochemical Identification of Glycosylation Inhibiting Factor; 1990; vol. 87 pp. 1903–1907. PNAS.

Hiroyuki Ohno, et al.; Effect of Phospholipase $A_2$ Inhibitors on Mouse T Lymphocytes; 1989 vol. 1 No. 4. International Immunology.

Makoto Iwata, et al.; Relationship Between T Cell Receptors and Antigen–Binding Factors; Dec. 15, 1989; vol. 143, 3909–3016. J. of Immunology.

Makoto Iwata, et al.; Construction of Antigen–Specific Suppressor T Cell Hybridomas From Spleen Cells of Mice . . . ; Nov. 15, 1988; vol. 141, 3270–3277. J. of Immunology.

Makoto Iwata, et al.; Relationship Between T Cell Receptors and Antigen–Binding Factors; Dec. 15, 1989; vol. 143, 3917–3924. J. of Immunology.

Paula Jardieu, et al.; Carrier–Specific Suppression of Antibody Responses by Antigen Specific Glycosylation . . . ; Mar. 1, 1987; vol. 138,1494–1501. J. of Immunology.

Robert J. Wise; Expression of a human proprotein processing enzyme; Correct Cleavage of the von Willebrand . . . Proc. Natl Acad Sci; vol. 87, pp. 9378, 1990.

Masahiro Hosaka Art–X–Lys/Arg–Arg Motif as a Signal for Precursor . . . The Journal of Biological Chemistry; vol. 266, No. 19, 1991; pp. 12127–12130.

Anthony Lanahan, et al.; Growth Factor–Induced Delayed Early Response Genes, Molecular and Cellular Biology, Sep. 1992 pp. 3919–3929 vol. 12, No. 9.

Graeme J. Wistow, et al.; A Macrophage Migration Inhibitory Factor is Expressed. Proc. Natl. Acad. Sci USA, vol. 90 pp. 1272–1275, Feb. 1993.

Weishui Y. Weiser, et al.; Molecular cloning of a cDNA encoding a human . . . Proc. Natl. Acad. Sci USA vol. 86, pp. 7522–7526, Oct. 1989.

John R. David, M.D., Erratum, The Journal of Immunology, vol. 151, 1 No. 9 Nov. 1, 1993.

*Primary Examiner*—Elizabeth C. Kemmerer
*Assistant Examiner*—David S. Romeo
*Attorney, Agent, or Firm*—Fish & Richardson, P.C.

[57] ABSTRACT

Polypeptides, polynucleotides, fragments thereof, and monoclonal antibodies thereto are provided for antigen-specific and antigen-non-specific glycosylation inhibiting factor and a method for recombinant production of biologically active polypeptides from a structural gene encoding the polypeptide.

26 Claims, 5 Drawing Sheets

Murine GIF full length Sequence

```
                    .         .         .         .        50         .
         GGCACGACGTCAGGTCCCTGGCTTGGGTCACACCGCGCTTTGTACCGTCCTCCGGTCCAC

.         .         .        100         .         .
         GCTCGCAGTCTCTCCGCCACCATGCCTATGTTCATCGTGAACACCAATGTTCCCCGCGCC
                                    M  P  M  F  I  V  N  Y  N  V  P  R  A
                                    |-------------------------------------
                                    |                                    |---

.         .        150         .         .         .
         TCCGTGCCAGAGGGGTTTCTGTCGGAGCTCACCCAGCAGCTGGCGCAGCGCACCGGCAAG
          S  V  P  E  G  F  L  S  E  L  T  Q  Q  L  A  Q  R  T  G  K
         -----|                                                      |
              |                                                      |

.        200         .         .         .         .
         CCCGCACAGTACATCGCAGTGCACGTGGTCCCGGACCAGCTCATGACTTTTAGCGGCACG
          P  A  Q  Y  I  A  V  H  V  V  P  D  Q  L  M  T  F  S  G  T

250         .         .         .         .        300
         AACGATCCCTGCGCCCTCTGCAGCCTGCACAGCATCGGCAAGATCGGTGGTGCCCAGAAC
          N  D  P  C  A  L  C  S  L  H  S  I  G  K  I  G  G  A  Q  N
         |-------------------------------------|
         |                                     |
                                               |-----------------------
                                               .        350         .
         CGCAACTACAGTAAGCTGCTGTGTGGCCTGCTGTCCGATCGCCTGCACATCAGCCCGGAC
          R  N  Y  S  K  L  L  C  G  L  L  S  D  R  L  H  I  S  P  D
         -----------------|                    |----------------------
                                               .        400         .
         CGGGTCTACATCAACTATTACGACATGAACGCTGCCAACGTGGGCTGGAACGGTTCCACC
          R  V  Y  I  N  Y  Y  D  M  N  A  A  N  V  G  W  N  G  S  T
         ---------------------|  |-------------------------------------
                    .         .        450         .         .         .
         TTCGCTTGAGTCCTGGCCCCACTTACCTGCACCGCTGTTCTTTGAGCCTCGCCTCTCCAC
          F  A  *
         ------|
               |    .        500         .         .         .         .
         GTAGTGTTCTGTGTTTATCCACCGGTAGCGATGCCCACCTTCCAGCCGGGAGAAATAAAT
                  550         .         .         .         .        600
         GGTTTATAAGAGACCAAAAAAAAAAAAAAAAAAAAAAAAAAAAAAAAAAAAAAAAAAAAA
                    .         .         .         .
         AAAAAAAAAAAAAAAAAAAAAAAAAAAAAAAAAAA
```

FIG. I

Human GIF cDNA full length Sequence

```
                .         .         .         .        50         .
         CAGGCACGTAGCTCAGCGGCGGCGCGGCGCGTGCGTCTGTGCCTCTGCGCGGGTCTCCTG

.         .         .        100         .         .
         GTCCTTCTGCCATCATGCCGATGTTCATCGTAAACACCAACGTGCCCCGCGCCTCCGTGC
                         M   P   M   F   I   V   N   T   N   V   P   R   A   S   V

.         .   SacI150        .         .         .
         CGGACGGGTTCCTCTCCGAGCTCACCCAGCAGCTGGCGCAGGCCACCGGCAAGCCCCCC
           P   D   G   F   L   S   E   L   T   Q   Q   L   A   Q   A   T   G   K   P   P

.        200         .         .         .         .
         AGTACATCGCGGTGCACGTGGTCCCGGACCACGTCATGGCCTTCGGCGGCTCCAGCGAGC
           Q   Y   I   A   V   H   V   V   P   D   Q   L   M   A   F   G   G   S   S   E

250  PstI    .         .         .         .        300
         CGTGCGCGCTCTGCAGCCTGCACAGCATCGGCAAGATCCGCGGCGCGCAGAACCGCTCCT
           P   C   A   L   C   S   L   H   S   I   G   K   I   G   G   A   Q   N   R   S

.         .         .         .        350         .
         ACAGCAAGCTGCTGTGCGGCCTGCTGGCCGAGCGCCTGCGCATCAGCCCGGACAGGGTCT
           Y   S   K   L   L   C   G   L   L   A   E   R   L   R   I   S   P   D   R   V

.         .         .        400         .         .
         ACATCAACTATTACGACATGAACGCGGCCAATGTGGGCTGGAACAACTCCACCTTCGCCT
           T   I   N   Y   Y   D   M   N   A   A   N   V   G   W   N   N   S   T   F   A

.         .        450        •SmaI       .         .
         AAGAGCCGCAGGGACCCACGCTGTCTGCGCTGGCTCCACCCGGGAACCCGCCGCACGCTG
           *

.        500         .         .         .         .
         TGTTCTAGGCCCGCCCACCCCAACCTTCTGGTGGGGAGAAATAAACGGTTTAGAGACTAA

550
         AAAAAAAAAAAAAAAAAA
```

FIG. 2

METHOD FOR RECOMBINANT PRODUCTION OF ANTIGEN NON-SPECIFIC GLYCOSYLATION INHIBITING FACTOR (GIF)

This is a continuation of application Ser. No. 08/061,041, filed May 14, 1993, now abandoned, which is a continuation-in-part of PCT/US92/04614, filed Jun. 3, 1992, which is a continuation-in-part of Ser. No. 709,375, filed Jun. 3, 1991, now abandoned, which is a continuation-in-part of Ser. No. 533,889, filed Jun. 4, 1990 now abandoned.

This invention was made with Government support under grant numbers AI11202, AI14784, and AI32834 awarded by the National Institutes of Health. The Government has certain rights in the invention.

FIELD OF THE INVENTION

The invention relates to human glycosylation inhibiting factor (GIF) which can be used to suppress the human immune response to an antigen and polynucleotide sequences encoding GIF.

DESCRIPTION OF THE BACKGROUND ART

Although the immune response is often seen as beneficial, in certain circumstances the immune response to an antigen can actually be harmful to the animal in which the immune response occurs. An example where the immune response creates a condition wherein the host is subject to serious pathologic sequelae is in such autoimmune diseases as lupus erythematosus. In lupus erythematosus, antibodies are often present which react with determinants in the thyroid, erythrocytes, DNA, and platelets of the host.

Another example of where the suppression from immune response would be described is in the treatment of allergies. It has been established that IgE antibodies against allergens cause hay fever, and are involved in the other allergic diseases such as extrinsic asthma. The crucial role of IgE antibodies in the allergic diseases raised the possibility that the regulation and suppression of the IgE antibody formation against allergens would be one of the fundamental treatments for allergic diseases. For example, in the serum of hay fever patients sensitive to ragweed allergens, IgE antibodies against the allergens are always detected. The IgE antibody titer goes up after the pollen season, and then declines only slightly during the rest of the year. Since the half life of IgE in the serum is only 2 to 3 days, the persistence of the IgE antibody titer indicates that the antibodies are being synthesized continuously by the lymphoid cells of the patients in spite of the lack of allergen exposure.

Over the past 20 years, several different attempts were made to control the IgE antibody response in experimental animals. One of the approaches was to improve classical immunotherapy or desensitization treatment, in which allergic patients receive repeated injections of a minute dose of allergen. It was shown that the desensitization treatment can improve clinical symptoms in some patients. However, the IgE antibody titer in the serum of hay fever patients did not decline after the treatment. The major immunological effects of the treatment is an enhancement of the IgG antibody formation, and the suppression of an increase in the IgE antibody titer after the pollen season.

A limitation in the desensitization, or immunosuppression treatment is that patients cannot tolerate a large dose of allergen because of side effects. In order to overcome this difficulty, attempts were made to use a chemically modified allergen, such as urea-denatured antigen or polyethylene glycol (PEG)-conjugates of the antigen for the treatment. Since the modified antigens do not bind to antibodies against the native antigen, relatively large doses of the modified antigen can be injected without causing allergic symptoms. However, the modified antigen can stimulate antigen-specific T-cells. Evidence was obtained that intravenous injections of the modified antigen into mice resulted in the generation of antigen-specific suppressor T-cells which suppressed the primary IgE antibody response to the native antigen. However, the treatment had minimal effects on the on-going IgE antibody formation, if the treatment were initiated after the antibody titer reached maximum (Takatsu and Ishizaka, *J. Immunol.*, 117: 1211, 1976). In agreement with the observations in the mouse, clinical trials of polyethylene-glycol-conjugated allergen in hay fever patients showed that the treatment failed to diminish the IgE antibody titer. Failure of the repeated injections of the modified antigen to suppress the on-going IgE antibody formation is probably due to the presence of a relatively large population of antigen-specific helper T-cells in the allergic patients. Since the modified antigen not only induces the generation of antigen-specific suppressor T-cells, but also expands the population of helper T-cells, this latter effect of the treatment might have overcome the effect of suppressor T-cells. This interpretation is supported by the fact that transfer of antigen-specific suppressor T-cells into immunized mice resulted in the suppression of the on-going IgE antibody formation (Takatsu and Ishizaka, *J. Immunol.*, 117: 1211, 1976). The results collectively suggested that the persistent IgE antibody formation in hay fever patients could be suppressed, if it were possible to generate the antigen-specific suppressor T-cells without expanding the helper T-cell populations.

Since 1980, the inventors have investigated various ways in which IgE synthesis is selectively regulated in an immunoglobulin isotype-specific manner. As a result of this research, two types of T-cell factors have been found which have affinity for IgE and selectively regulate IgE synthesis. One of the IgE-binding factors (IgE-BF) selectively enhances the IgE response, while the other type of IgE-BF selectively suppresses the response. The major difference between the IgE-potentiating factors and IgE-suppressive factors appears to be carbohydrate moieties in the molecules. The IgE-potentiating factors bind to lentil lectin and concanavalin A, while IgE-suppressive factors fail to bind to these lectins (Yodoi, et al., *J. Immunol.*, 128: 289, 1982). Analysis of the cellular mechanism for the selective formation of either IgE-potentiating factors or IgE-suppressive factors, as well as gene cloning of the factors, indicated that the IgE-potentiating factor and IgE-suppressive factor share a common structural gene and that the nature of the carbohydrate moieties and biologic activities of the factors are established during the post-translational glycosylation process (Martens, et al, *Proc. Nat'l Acad. Sci., U.S.A.*, 84: 809, 1987). Under the physiological conditions, this glycosylation process is controlled by two T-cell factors which either enhance or inhibit this process. These factors are denominated glycosylation inhibiting factor (GIF) and glycosylation enhancing factor (GEF).

A unique property of GIF is its biochemical activity. This lymphokine binds to monoclonal antibodies against lipomodulin (a phospholipase inhibitory protein) and appears to be a phosphorylated derivative of a phospholipase inhibitory protein (Uede, et al., *J. Immunol*, 130: 878, 1983). It was also found in the mouse that the major source of GIF is antigen-specific suppressor T-cells (Ts) (Jadieu, et al., *J. Immunol.*, 133: 3266, 1984). Subsequent experiments on ovalbumin (OVA)-specific suppressor T-cell hybridomas indicated that stimulation of the hybridoma cells with antigen (OVA)-pulsed syngeneic macrophages resulted in the formation of GIF that has affinity for OVA (antigen-binding GIF). However, the same hybridomas constitutively secreted GIF having no affinity for OVA (nonspecific GIF). Studies on the relationship between nonspecific GIF and OVA-binding GIF indicated that the antigen-binding GIF is composed of an antigen-binding polypeptide chain and a nonspecific GIF (Jardieu, and Ishizaka, in *Immune Regulation By Characterized Polypeptides*, Goldstein, et al., eds., Alan R. Liss, Inc., N.Y., p595, 1987). It was also found that the antigen-binding GIF shares common antigenic determinants with antigen-specific suppressor T-cell factors (TsF) described by the other investigators, and suppressed the antibody response in an antigen (carrier)-specific manner. Furthermore, not only antigen-binding GIF, but also antigen-specific TsF described by other investigators, bound to immunosorbent coupled with monoclonal anti-lipomodulin (141 -B9), and were recovered by elution of the immunosorbent at acid pH.

Despite the major limitations of desensitization in treating allergy, this technique continues to be the method of choice. Consequently, there is significant need for a technique which is antigen-specific yet does not have associated with it the side effects seen with existing desensitization regimens.

The suppression of the immune response is crucial in order to prevent host versus graft (HVG) and graft versus host rejection (GVH). Unfortunately, in the case of both autoimmune disease as well as in HVG and GVH, the immune response suppression uses highly toxic drugs which are of limited effectiveness and act systemically, rather than specifically. The severe limitations of such therapy point to the need for immunosuppressive agents which have less toxicity, but greater specificity.

An improved way to suppress an immune response to an antigen in a human would be to administer an immunosuppressively effective amount of human GIF which can specifically bind to the antigen. In so doing, the concentration of T suppressor factor is favored and, as a result, the immune response to the antigen is decreased. The present invention provides a means for accomplishing this result.

SUMMARY OF THE INVENTION

The invention provides substantially purified human antigen-specific and antigen non-specific GIF and the nucleotide sequence encoding GIF. A general method for the recombinant production of biologically active polypeptides is also provided.

BRIEF DESCRIPTION OF THE DRAWINGS

FIG. 1 shows the nucleotide and deduced amino acid sequence of a cDNA clone for murine GIF.

FIG. 2 shows the nucleotide and deduced amino acid sequence of a cDNA clone for human GIF.

DETAILED DESCRIPTION OF THE INVENTION

Figure 3:
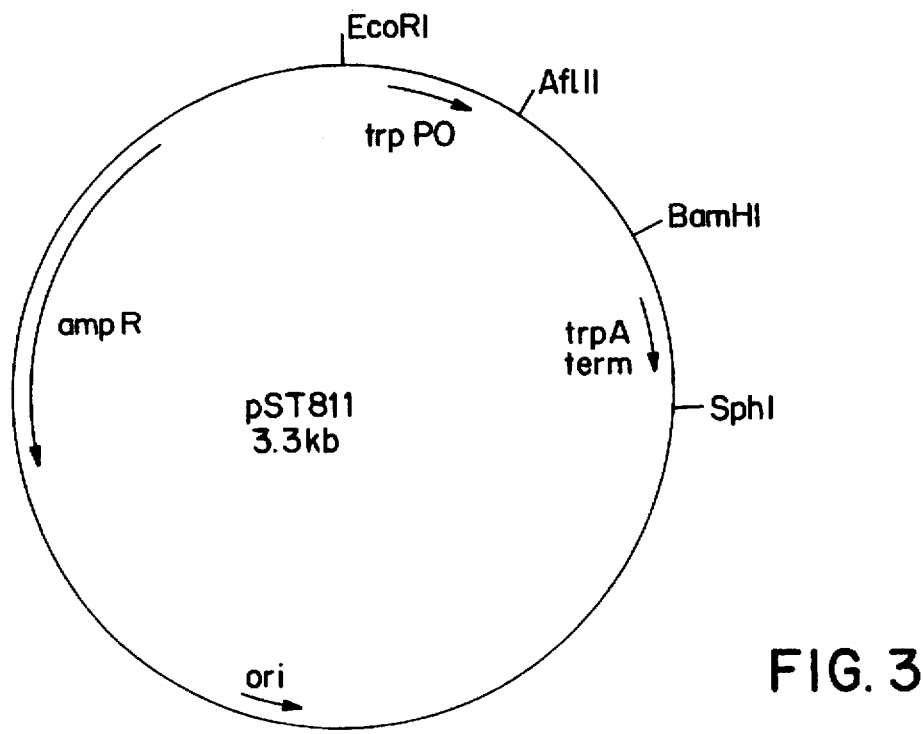
FIG. 3 shows a map of the pST811 vector.

The present invention relates to substantially pure human antigen-specific GIF with specificity for an antigen associated with an undesirable immune response. This human antigen-specific GIF is highly useful for the immunosuppression of the undesirable immune response in an antigen-specific manner.

Preferred in the present invention are human antigen-specific GIFs which can specifically bind allergens. In an especially preferred embodiment of the invention, a human antigen-specific GIF is disclosed which binds to an epitope on bee venom phospholipase $A_2(PLA_2)$, the major allergen in honey bee venom. This specificity enables this antigen-specific GIF, and like antigen-specific GIFs with the same specificity, to be used to suppress the human immune response to $PLA_2$. In another especially preferred embodiment of the invention, a human antigen-specific GIF is disclosed which binds to an epitope on Japanese cedar pollen which can be used to suppress the human immune response to this antigen.

The teaching used to produce GIF with antigen-specificity to bee venom $PLA_2$ can be readily extended to other antigens by those of skill in the art to prepare and purify other GIF molecules with antigenic specificity for those other antigens without undue experimentation. As a consequence, the broad pioneering nature of the invention enables the preparation of human antigen-specific GIFs for other allergens which can be used to suppress such immune response mediated disorders as autoimmune disease and allergy. The production of various human antigen-specific GIFs is especially facilitated where the antigen of the undesirable immune response is known such as with most allergies and various autoimmune diseases.

The human $PLA_2$-specific GIF of the invention is obtained from, or has the identifying characteristics of, an antigen-specific GIF obtained from the cell line AC5 having ATCC accession number HB 10473. The human Japanese cedar pollen-specific GIF of the invention is obtained from, or has the identifying characteristics of, an antigen-specific GIF obtained from the cell line 31E9 (ATCC HB 11052).

Methods of Producing and Characterizing Hybridomas

The general method used for production of hybridomas is well known (Kohler, et al., *European J. Imm.*, 6: 292, 1976). Briefly, peripheral blood mononuclear cells (PBMC) from a human allergic to honey bee venom were cultured in the presence of chemically modified $PLA_2$. Non-adherent cells were recovered and then cultured with IL-2 and lipocortin-1 prior to fusion with lymphoblastoid cell line BUC. Hybridomas were screened for production of human GIF specific for $PLA_2$.

More generally, the invention is directed to a method of producing a continuous hybridoma cell line which produces human antigen-specific GIF comprising:

(a) obtaining human antigen-primed T-cells which are activated to the antigen and cultured in the presence of IL-2 and a phospholipase $A_2$ inhibitor; and (b) combining the activated T-cells by fusion with a fusion partner cell line to produce hybridomas capable of producing human antigen-specific GIF.

The antigen-primed T-cells can be obtained from any sample, including the mononuclear cell fraction of peripheral blood. The antigen-primed T-cells can then be activated by culturing in the presence of the antigen to which they have been primed, followed by expanding the activated T-cells in the presence of interleukin-2 (IL-2) and a phospholipase $A_2$ inhibitor. An especially useful phospholipase $A_2$ inhibitor for such purposes is lipocortin. Alternatively, synthetic compounds with $PLA_2$ inhibitory activity can be used such as 2-(p-amylcinnamoyl)-amino-4-chlorobenzoic acid, (ONO-RS-082, ONO Pharmaceutical Co.).

Under certain circumstances, such as where the primary antigen is toxic to the T-cells, it is desirable to chemically modify the antigen. Agents useful for such modification include guanidine HCl and cyanogen bromide, but those of skill in the art can easily ascertain similar agents without undue experimentation. Generally, it is preferred to use agents which do not destroy the external structure of the antigen, since it is thought that such external structures are important in suppressor T-cell epitopic recognition of the antigen. However, this issue is not significant for most antigens, such as many allergens, which are not cytotoxic. Consequently, with typical allergens, the native molecules can be used to stimulate the T-cells.

The present invention is directed to a method for generating antigen-specific human T-cells and T-cell hybridomas which produce human antigen-specific GIF, which are specifically reactive with an antigen which is associated with an immune response to be immunosuppressed.

The isolation of T-cell hybridomas producing a human antigen-specific GIF with the antigenic specificity of the human antigen-specific GIF of the invention can be accomplished using routine screening techniques to determine the elementary reaction pattern of the human antigen-specific GIF of interest. Thus, for example in the case of human GIF specific for $PLA_2$, if a human antigen-specific GIF being tested suppresses the immune response of cells from a patient allergic to $PLA_2$, then the human antigen-specific GIF being tested and the human GIF specific for $PLA_2$ produced by the hybridoma of the invention are equivalent.

Still another way to determine whether a human antigen-specific GIF has the specificity of a human antigen-specific GIF of the invention is to pre-incubate the human antigen-specific GIF of the invention with the antigen with which it is normally reactive (for example, bee venom $PLA_2$), and determine if the human antigen-specific GIF being tested is inhibited in its ability to bind the antigen. If the human antigen-specific GIF being tested is inhibited then, in all likelihood, it has the same epitopic specificity as the human antigen-specific GIF of the invention.

As used in this invention, the term "epitope" is meant to include any determinant capable of specific interaction with a human antigen-specific GIF or the monoclonal antibodies of the invention. Epitopic determinants usually consist of chemically active groupings of molecules such as amino acids or sugar side chains and usually have specific three dimensional structural characteristics, as well as specific charge characteristics.

In still another aspect, the invention relates to a method of producing substantially pure human antigen-specific GIF comprising:

(a) culturing a continuous hybridoma cell line capable of producing human antigen-specific GIF such that the cell line produces human antigen-specific GIF; and (b) isolating substantially pure human antigen-specific GIF from the culture.

The continuous hybridoma cell lines so used can themselves be produced as described above. In addition, during culturing the hybridoma cell line is preferably stimulated to produce human antigen-specific GIF by exposing the hybridoma cells to syngeneic macrophages which have been pulsed with the antigen to which the antigen-specific GIF binds, or with antibodies to the CD3 or T-cell receptor.

Various techniques can be used to isolate or substantially purify the human antigen-specific GIF from the culture. A particularly useful technique is affinity purification using the antigen, for example attached to a solid phase, to which the antigen-specific GIF binds. A modification of this technique is to use two affinity absorption steps, if desirable, to substantially purify the human antigen-specific GIF. In such a process, the step of isolating substantially pure human antigen-specific GIF includes:

(i) reacting the hybridoma cell line culture with a monoclonal antibody specifically reactive with human GIF;

(ii) eluting the human GIF from the monoclonal antibody;

(iii) reacting the eluted GIF with the antigen to which the human antigen-specific GIF binds;

(iv) eluting the human antigen-specific GIF from the antigen; and (v) recovering the human antigen-specific GIF.

Alternatively, immunosorbent coupled to the monoclonal antibody against antigen-specific GIF such as 110BH3, may be used instead of antigen-coupled immunosorbent. The step of isolating substantially pure human antigen-specific GIF includes:

(i) reacting the hybridoma cell line culture with a monoclonal antibody to which the human antigen-specific GIF binds;

(ii) eluting the human GIF from the monoclonal antibody;

(iii) reacting the eluted GIF with a monoclonal antibody specifically reactive with human GIF;

(iv) eluting the human antigen-specific GIF from the monoclonal antibody; and (v) recovering the human antigen-specific GIF.

Purification of human antigen-specific GIF is facilitated by adjusting the hybridoma cells to serum-free culture medium, such as ABC. After treatment of the subclone with anti-CD3, followed by culture of the hybridoma cells in Protein A-coated tissue culture dishes, antigen-binding GIF in culture supernatants can be purified by ion-exchange chromatography, described above. Under such conditions, the process of isolating substantially pure human antigen-specific GIF includes:

(i) contacting the hybridoma cell line culture supernatant with an anionic exchange matrix;

(ii) eluting the human GIF from the matrix;

(iii) reacting the eluted GIF with a monoclonal antibody specifically reactive with human GIF or with the antigen to which the human antigen-specific GIF binds, or both;

(iv) eluting the human antigen-specific GIF; and (v) recovering the human antigen-specific GIF.

Thus, ion-exchange chromatographic purification is used in combination with affinity-purification to isolate human antigen-specific GIF, for example, by using the antigen to which the antigen-specific GIF binds or by using an antibody specifically reactive with human GIF, or both, as described above.

In the preferred embodiment, DEAE (diethylaminoethyl) Sepharose is the matrix utilized for purification of antigen-specific human GIF. Other ion-exchange materials which can be utilized include virtually any of the commercially available anion exchange agaroses and celluloses, such as polysulfated agaroses, specifically including but not limited to QAE (quaternary amine) derivatives, ecteola (epichlorohydrintri-ethanolamine), TEAE (triethylaminoethyl) derivatives, and AE (aminoethyl) cellulose. The specific parameters for binding and eluting from these various ion-exchange materials can be known to those of skill in the art, or can be readily ascertained, without undue experimentation.

When the hybridoma cell line culture supernatant is added to the anion-exchange matrix equilibrated with about 20 mM salt, e.g., NaCl, much of the GIF will pass through the column and the remainder are eluted with salt concentrations up to about 60 mM. Preferred for elution from DEAE are concentrations of NaCl from about 20 mM to about 60 mM contained in 10 mM Tris.

A monoclonal antibody which is particularly useful in the affinity purification of human GIF is the monoclonal antibody produced by a cell line 388$F_1$ or monoclonal antibodies having the specificity of a monoclonal antibody produced by cell line 388$F_1$ and a monoclonal antibody produced by a cell line 110BH3 or monoclonal antibodies having the same specificity.

THERAPEUTIC USES OF HUMAN ANTIGEN-SPECIFIC AND ANTIGEN NON-SPECIFIC GIF

The term "suppressive" denotes a lessening of the detrimental effect of the undesirable immune response in the human receiving therapy. The term "immunosuppressively effective" means that the amount of human antigen-specific or non-specific GIF used is of sufficient quantity to suppress the cause of disease or symptoms due to the undesirable immune response.

The dosage ranges for the administration of the human GIF of the invention are those large enough to produce the desired effect in which the symptoms of the immune response show some degree of suppression. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 0.001 mg/kg/dose to about 2 mg/kg/dose, preferably about 0.001 mg/kg/dose to about 0.2 mg/kg/dose, in one or more dose administrations daily, for one or several days.

The human GIF of the invention can be administered parenterally by injection or by gradual perfusion over time. The human GIF of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the human antigen specific and antigen non-specific GIF of the invention, the medicament being used for therapy of an undesirable immune response to an antigen wherein the antigen is capable of binding by the human GIF of the invention.

The present invention is also directed to monoclonal antibodies, and B-cell hybridomas which produce them, which are specifically reactive with human GIF. In addition, the invention provides monoclonal antibodies (and B-Cell hybridomas) which are specifically reactive with antigen-specific GIF but not with nonspecific GIF. A representative monoclonal antibody of this type is 110BH3.

As stated above, techniques for production of hybridomas are well known to those of skill in the art. In brief, the B-cell hybridomas of the invention were prepared by immunizing BALB/c mice with affinity-purified human GIF and later boosted. Two weeks after the last immunization, spleen cells were obtained from the animals and transferred to syngeneic BALB/c mice which had been lethally irradiated. The syngeneic recipients were immunized twice with purified human GIF and 2 weeks after the last immunization the spleen cells were fused with SP 2/0-14AG myeloma cell line. Hybridomas were screened for monoclonal antibody production to human GIF.

The isolation of hybridomas producing monoclonal antibodies with the reactivity of the monoclonal antibodies of the invention can be accomplished using routine screening techniques to determine the elementary reaction pattern of the monoclonal antibody of interest. Thus, if a monoclonal antibody being tested reacts with human GIF, but does not react with mouse GIF, then the antibody being tested and the antibody produced by the hybridomas of the invention are equivalent.

The isolation of other hybridomas producing monoclonal antibodies with the specificity of monoclonal antibody 388$F_1$, or any other monoclonal antibody of the invention, can be accomplished by one of ordinary skill in the art by producing anti-idiotypic antibodies (Herlyn, et al., *Science*, 232: 100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies produced by the second animal, which are specific for the monoclonal antibodies produced by a single hybridoma which was used to immunize the second animal, it is now possible to identify other clones with the same idiotype as the antibody of the hybridoma used for immunization and thereby greatly simplify and reduce the amount of screening needed to find other hybridomas producing monoclonal antibodies with the specificity of the monoclonal antibodies of the invention.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity as a monoclonal antibody of the invention by determining whether the monoclonal antibody being tested prevents the monoclonal antibody of the invention from binding to a particular antigen, for example human GIF, with which 388$F_1$ is normally reactive. If the monoclonal antibody being tested competes with 388$F_1$, for example, as shown by a decrease in binding by 388$F_1$, then it is likely that the two monoclonal antibodies bind to the same epitope. The similar test can be utilized for monoclonal antibody 110BH3.

Still another way to determine whether a monoclonal antibody has the specificity of a monoclonal antibody of the invention, such as 388F$_1$, is to pre-incubate 388F$_1$ with an antigen with which it is normally reactive, for example, human GIF, and determine if the monoclonal antibody being tested is inhibited in its ability to find the antigen. If the monoclonal antibody being tested is inhibited then, in all likelihood, it has the same epitopic specificity as the monoclonal antibody of the invention.

Under certain circumstances, monoclonal antibodies of one isotype might be more preferable than those of another in terms of their diagnostic or therapeutic efficacy. Particular isotypes of a monoclonal antibody can be prepared either directly, by selecting from the initial fusion, or prepared secondarily, from a parental hybridoma producing monoclonal antibody of different isotype, by using the sib selection technique to isolate class-switch variants (Steplewski, et al., *Proceedings of National Academy of Sciences, USA*, 82: 888653, 1985; Spira, et al., *Journal of Immunological Methods*, 74: 307, 1984). Thus, the monoclonal antibodies of the invention would include class-switch variants having the specificity of monoclonal antibody 388F$_1$ which is produced by ATCC HB 10472. This cell line was placed on deposit for 30 years at the American Type Culture Collection (ATCC) in Rockville, Md. prior to Jun. 4, 1990.

The term "antibody" as used in this invention is meant to include intact molecules as well as fragments thereof, such as, for example, Fab and F(ab')$_2$, which are capable of binding the epitopic determinant.

The monoclonal antibodies of the invention can also be used in immunoaffinity chromatography for the purification of the various types of human GIF mentioned herein. One way by which such immunoaffinity chromatography can be utilized is through the use of, for example, the binding of the monoclonal antibodies of the invention to CNBr-Sepharose-4B, Affigel (BioRad), or Tresyl-activated Sepharose (Pharmacia). These solid phase-bound monoclonal antibodies can then be used to specifically bind human GIF from mixtures of other proteins to enable its isolation and purification. The bound GIF can be eluted from the affinity chromatographic material using techniques known to those of ordinary skill in the art such as, for example, chaotropic agents, low pH, or urea.

In another embodiment, the invention provides a substantially pure fusion polypeptide R$_1$-[X$_1$-X$_2$-X$_1$-X$_2$-Lys-Arg]-R$_2$, wherein R$_1$ is a carrier peptide, R$_2$ is a polypeptide encoded by a structural gene, X$_1$ is Lys or Arg, and X$_2$ is any amino acid. The "carrier peptide", or signal sequence, is located at the amino terminal end of the fusion peptide sequence. In the case of eukaryotes, the carrier peptide is believed to function to transport the fusion polypeptide across the endoplasmic reticulum. The secretory protein is then transported through the Golgi apparatus, into secretory vesicles and into the extracellular space or, preferably, the external environment. Carrier peptides which can be utilized according to the invention include pre-pro peptides which contain a proteolytic enzyme recognition site. Acceptable carrier peptides include the amino terminal pro-region of calcitonin or other hormones, which undergo cleavage at the flanking dibasic sites. Procalcitonin is processed by prohormone convertase which recognizes Lys-Arg cleavage site. However, it should be noted that the invention is not limited to the use of this peptide as a carrier. Other carrier peptides with similar properties to pro-calcitonin described herein are known to those skilled in the art, or can be readily ascertained without undue experimentation.

In one embodiment of the invention, a carrier peptide which is a signal sequence is included in the expression vector, specifically located adjacent to the N-terminal end of the carrier protein. This signal sequence allows the fusion protein to be directed toward the endoplasmic reticulum. Typically, the signal sequence consists of a leader of from about 16 to about 29 amino acids, starting with two or three polar residues and continuing with a high content of hydrophobic amino acids; there is otherwise no detectable conservation of sequence known. While the vector used in the example of the present invention uses the pro-region of calcitonin, other signal sequences which provide the means for transport of the fusion protein to the endoplasmic reticulum and into the external environment, will be equally effective in the invention. Such signal sequences are known to those of skill in the art.

The carrier peptide of the invention contains a proteolytic enzyme recognition site which has a dibasic motif (Lys-Arg) which contains an additional Arg/Lys residue at the P4 and P6 positions. Differences in the cleavage recognition site may imply that different processing enzymes exist for the proteolytic specificity. Preferably, the cleavage site is about 6 amino acids having the sequence X$_1$-X$_2$-X$_1$-X$_2$-Lys-Arg, where X$_1$ is Lys or Arg and X$_2$ is any amino acid. This recognition site allows for an unexpectedly high level of active protein encoded by the structural gene to be produced.

Examples of processing enzymes which recognize the proteolytic site include the mammalian enzyme, furin, the homologue of the yeast propeptide processing enzyme Kex2, and other prohormone convertases (PCs). Preferably, the carrier peptide of the invention contains at the cleavage site within the precursor, a proteolytic enzyme recognition site, with a polynucleotide sequence encoding Arg/Lys-X$_2$-Arg/Lys-X$_2$-Lys-Arg.

The fusion polypeptide of the invention includes a polypeptide encoded by a structural gene, preferably at the carboxy terminus of the fusion polypetide. Any structural gene is expressed in conjunction with the carrier and cleavage site. The structural gene is operably linked with the carrier and cleavage site in an expression vector so that the fusion polypeptide is expressed as a single unit. GIF is an example of a structural gene that can be used to produce a fusion polypeptide of the invention.

The invention provides a substantially pure polypeptide. The term "substantially pure" as used herein refers to a polypeptide which is substantially free of other proteins, lipids, carbohydrates or other materials with which it is naturally associated. One skilled in the art can purify the polypeptide using standard techniques for protein purification, such as affinity chromatography using a monoclonal antibody which binds an epitope of the polypeptide. The substantially pure polypeptide will yield a single major band on a polyacrylamide gel. The purity of the polypeptide can also be determined by amino-terminal amino acid sequence analysis. The polypeptide includes functional fragments of the polypeptide, as long as the activity of the polypeptide remains. Smaller peptides containing the biological activity of polypeptide are included in the invention.

The invention also provides polynucleotides encoding the fusion polypeptide. These polynucleotides include DNA, cDNA and RNA sequences. It is understood that all polynucleotides encoding all or a portion of the fusion polypeptide are also included herein, as long as they encode a polypeptide of which the cleavage product has biological activity. Such polynucleotides include naturally occurring, synthetic, and intentionally manipulated polynucleotides. For example, the polynucleotide may be subjected to site-directed mutagenesis. The polynucleotide sequence also includes antisense sequences and sequences that are degenerate as a result of the genetic code. There are 20 natural amino acids, most of which are specified by more than one codon. Therefore, all degenerate nucleotide sequences are included in the invention as long as the amino acid sequence of the fusion polypeptide encoded by the nucleotide sequence is functionally unchanged.

The invention also provides polynucleotides which are complementary to the nucleotide sequences of the invention. A "complementary" nucleotide sequence will hybridize to a specific nucleotide sequence under conditions which allow the complementary sequence to hybridize. These conditions include temperature, pH, buffer and nucleotide composition. For example, the positive and negative strands of a double-stranded DNA molecule are complementary nucleotide sequences. Polynucleotides of the invention include fragments which are at least 15 bases in length, and typically 18 bases or greater, which selectively hybridize to genomic DNA which encodes the polypeptide of interest. Selective hybridization denotes conditions (e.g., pH, temperature, buffer) which avoid non-specific binding of a nucleotide sequence to the target DNA which is its complement.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features; and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucleic Acid Research, 9: 879, 1981).

An antigen non-specific GIF containing cDNA library, for example, can be screened by injecting the various cDNAs into oocytes, allowing sufficient time for expression of the cDNA gene products to occur, and testing for the presence of the desired cDNA expression product, for example, by using antibody specific for antigen non-specific GIF polypeptide or by using functional assays for GIF activity. Alternatively, a cDNA library can be screened indirectly for antigen non-specific GIF polypeptides having at least one epitope using antibodies specific for antigen non-specific GIF polypeptides. Such antibodies can be either polyclonally or monoclonally derived and used to detect expression product indicative of the presence of antigen non-specific GIF cDNA.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA.

The development of specific DNA sequences encoding a polypeptide can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., Nucl. Acid Res. 11: 2325, 1983).

A cDNA expression library, such as lambda gt11, can be screened indirectly for expression of a polypeptide having at least one epitope, using antibodies specific for the polypeptide. Such antibodies can be either polyclonally or monoclonally derived and used to detect expression product indicative of the presence of protein encoded by the cDNA.

DNA sequences encoding the fusion polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the polynucleotide sequences may be inserted into a recombinant expression vector. The term "recombinant expression vector" refers to a plasmid, virus or other vehicle known in the art that has been manipulated by insertion or incorporation of the genetic sequences for antigen non-specific GIF, for example, and a carrier peptide. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56: 125, 1987), the pMSXND expression vector for expression in mammalian cells (Lee and Nathans, *J. Biol. Chem.* 263: 3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding the polypeptide of the invention can be expressed in either prokaryotes or eukaryotes. Hosts can include microbial, yeast, insect and mammalian organisms. The preferred host of the invention is a eukaryote. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. It is preferable that the host cell of the invention naturally encodes an enzyme which recognizes the cleavage site of the fusion protein. However, if the host cell in which expression of the fusion polypeptide is desired does not inherently possess an enzyme which recognizes the cleavage site, the genetic sequence encoding such enzyme can be cotransfected to the host cell along with the polynucleotide sequence for the fusion protein.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982).

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies.

The above disclosure generally describes the present invention. A more complete understanding can be obtained by reference to the following specific examples which are provided herein for purposes of illustration only, and are not intended to limit the scope of the invention.

EXAMPLE 1

PREPARATION OF HYBRIDOMA CELL LINES PRODUCING HUMAN ANTIGEN-SPECIFIC GLYCOSYLATION INHIBITING FACTOR (GIF) AND PURIFICATION TECHNIQUES

A. ANTIGENS

Lyophilized phospholipase $A_2(PLA_2)$ from bee venom was purchased from Sigma Chemical Co., St. Louis, Mo. Denatured $PLA_2$ (-$PLA_2$) and cyanogen bromide-treated $PLA_2$ were prepared by the method described by King, et al., *Arch. Biochem and Biophys.*, 172: 661, 1976. For the preparation of D-$PLA_2$, 5 mg of $PLA_2$ were dissolved in 0.1M Tris HCl buffer, pH 8.6, and denatured in 6M guanidine HCl in the presence of 5 mg/ml dithiothreitol. After 18 hours at room temperature, sulfhydryl groups were carboxymethylated with iodoacetic acid. The denatured protein was dialyzed against 0.02M acetic acid and kept at −40° C. until use. For the cleavage of methionine bonds in $PLA_2$, 10 mg bee venom $PLA_2$ was dissolved in 0.4 ml distilled water, and 1.2 ml formic acid containing 100 mg CNBr were added. After 2 hours at room temperature, the mixture was diluted two-fold with $H_2O$ and lyophilized in Speed Vac. Native $PLA_2$ was coupled to Tresyl activated Sepharose (Pharmacia) following the procedures recommended by the manufacturer. Unless otherwise stated, 1 mg protein was coupled to 1 ml Sepharose.

B. ANTIBODIES

Purified human E myeloma protein PS, monoclonal mouse IgE from the hybridoma H-1 DNP-E-26 (Liu, et al., *J. Immunol.*, 124: 2728, 1980) and monoclonal anti-CD3 (OKT 3) were the same preparations as those described in a previous article (Carini, et al., *J. Immunol. Methods*, 127: 221, 1990). Ascitic fluid containing the monoclonal anti-T-cell receptor $\alpha\beta$, WT 31C, (Spits, et al., *J. Immunol.*, 135: 1922, 1985) was kindly supplied by Dr. J. DeVries, DNAX Institute of Molecular and Cellular Biology, Palo Alto, Calif. The mouse monoclonal antibody against rabbit lipomodulin 141B9 (Iwata, et al., *J. Immunol.*, 132: 1286, 1984) was the same preparation as that described in a previous article (Askasaki, et al., *J. Immunol.*, 131: 3172, 1986). Specifically-purified goat antibodies against mouse IgG, which contained both anti-heavy ($\gamma$) chain and anti-light chain, were previously described (Suemura, et al. *J. Immunol*, 125: 148, 1980). Fluoresceinated goat anti-mouse IgG antibodies were purchased from Cappel. Human IgE and anti-lipomodulin antibody (141B9) were coupled to CL-Sepharose 4B; approximately 5 mg of protein were coupled to 1 ml Sepharose.

C. CELL LINES

RPMI 8866 lymphoblastoid cells were cultured in RPMI 1640 medium enriched with 10% fetal calf serum, 2 mM L-glutamine, 50 µM 2-mercaptoethanol and antibiotics (RPMI 1640 culture medium). The mouse T-cell hybridoma 12H5 cells (Iwata, et al., *J. Immunol.*, 140: 2534, 1988) were maintained in high glucose Dulbecco's modified Eagle's medium (DMEM) described in a previous article (Huff, et al., *Proc. Natl. Acad. Sci., USA*, 129: 509, 1982). A hypoxanthine guanine phosphoribosyltransferase-deficient mutant of the human lymphoblastoid cell line CEM (BUC) cells were previously described (Huff & Ishizaka, *Proc. Natl. Acad. Sci., USA*, 81: 1514, 1984).

D. CELL CULTURE AND CONSTRUCTION OF HYBRIDOMAS

Peripheral blood was obtained from a patient allergic to honey bee venom, and mononuclear cells of the blood (PBMC) were obtained by centrifugation on Ficoll-Paque (Pharmacia). To activate antigen-primed T-cells, PBMC were suspended in RPMI 1640 culture medium at the concentration of $3\times10^6$ nucleated cells/ml, and cultured for three days in the presence of 10 µg/ml D-$PLA_2$ or CNBr-treated $PLA_2$. Non-adherent cells were recovered, resuspended in fresh culture medium ($2\times10^5$ cells/ml), and then cultured for four days with 60 units/ml purified IL-2 (chromatographically purified human IL-2, Electronucleonics, Silver Spring, Md.), in the presence of 3 µg/ml recombinant human lipocortin 1, which was kindly supplied by Drs. J. Browning and B. Pepinsky, Biogen.

To construct T-cell hybridomas, $1.2 \times 10^7$ T-cells, which had been propagated by IL-2, were mixed with twice the number of BUC cells (a subline of CEM). Mixed cells were pelleted together and fused by using polyethylene glycol (1300–1600 MW., Sigma). Detailed procedures for cell fusion were as previously described (Huff, et al., *Proc. Nat'l. Acad. Sci., U.S.A.* 81: 1514, 1984). Cells were resuspended in hypoxanthine/aminopterin/thymidine (HAT)-containing DMEM, and $5 \times 10^4$ cells were seeded in each well of 96 well plates. Hybrid clones were maintained in complete DMEM with biweekly subcultures. In order to stimulate the T-cell hybridomas, the cells were treated with 8 µg/ml OKT 3 for 40 minutes at 0° C., and the antibody-treated cells ($1 \times 10^6$/ml) were seeded in Limbro tissue culture wells (Flow Labs, McLean, Va.) which had been coated with 10 µg/ml anti-MGG. Culture supernatants were obtained after 24 hour culture.

E. DETECTION OF CD3 AND TcR

The hybridoma cells ($1 \times 10^6$/sample) were incubated 40 minutes at 0° C. with 8 µg/ml OKT 3 or a 1:1000 dilution of anti-TcRαβ(WT31)-containing ascitic fluid in RPMI 1640 medium supplemented with 5% FCS and 10 µM NaN3. As controls, aliquots of the same cells were treated with the same concentration of mouse $IgG_{2a}$ (Becton-Dickinson, isotype control). Cells were washed twice with PBS containing 5% FCS, and then incubated with fluoresceinated anti-mouse IgG for 40 minutes. After washings, cell-associated fluorescence was analyzed by using FACScan from Becton-Dickinson.

The CD3$^+$ hybridoma cells were identified by rosetting using ox erythrocytes coated with anti-mouse IgG. The antibodies were coupled to erythrocytes by the method of Wilhelm, et al., (*J. Immunol. Methods*, 90: 89, 1986). Briefly, 0.5 ml of packed ox erythrocytes were washed 4 times with saline, and resuspended in 0.75 ml of 0.5 µg/ml purified anti-MGG; 25 µl of CrCl$_3$ (16.5 mg CrCl$_3$ dissolved in 5 ml saline) were added to the cell suspension under gentle mixing, and the cell suspension was incubated for 1 hour at 30° C. The anti-MGG-coupled erythrocytes were washed 4 times with saline and resuspended in 5 ml FCS (approximately $1 \times 10^9$ erythrocytes/ml). To detect the CD3$^+$ cells, pellets of $10^6$ hybridoma cells were suspended in 80 µl of DPBS containing 5% FCS and 8 µg/ml OKT 3. After 45 minutes at 0° C., the cells were washed twice and resuspended in 80 µl DPBS-5% FCS, and 20 µl of a suspension of anti-MGG-coated erythrocytes and crystal violet were added to the cell suspension. The mixtures were centrifuged at 200 g for 5 minutes and tubes were incubated for 2 hours at 0° C. The pellets were gently resuspended and examined for rosetting cells under microscope.

F. ENRICHMENT OF CD3$^+$ CELLS

Hybridoma cells treated with 8 µg/ml OKT 3 ($1.5 \times 10^6$ cells) were mixed with anti-MGG coupled erythrocytes (ca $4 \times 10^8$ erythrocytes) to form rosettes by the procedures described above. Pellets were resuspended and applied to the top of Percoll gradient consisting of 60% and 50% Percoll layers. Tubes were centrifuged for 20 minutes at 1200 RPM (700 g) at room temperature. The pelleted cells were washed twice with culture medium, and the erythrocytes were lysed by treatment with 0.83% NH$_4$Cl buffer for 1 minute at 0° C. The cells were washed with and resuspended in DME culture medium and cultured to expand the cell population.

Further enrichment of CD3$^+$ cells was carried out by cell sorting. Hybridoma cells were treated with OKT 3 and stained with fluoresceinated anti-MGG. The positively stained cells were selected by sorting the cells by using FACSTAR (Becton-Dickinson).

G. PURIFICATION AND DETECTION OF IgE-BF

Culture supernatant of T-cell hybridomas were filtered through Diaflo YM 100 membranes (Amicon Corp., Lexington, Mass.) and the filtrates were concentrated ten-fold by ultrafiltration through YM5 membranes. IgE-BF in the filtrates were purified by using IgE-coupled Sepharose by the described procedures (Ishizaka & Sandberg, *J. Immunol*, 126: 1692, 1981). The presence of IgE-BF in culture filtrates or acid eluate fraction from IgE-Sepharose was assessed by inhibition of rosette formation of FcεR$^+$B lymphoblastoid cell line, RPMI 8866 cells with human IgE-coated ox erythrocytes (E-IgE) by the procedures previously described (Kisaki, et al., *J. Immunol.*, 138: 3345, 1987). The proportion of rosette forming cells (RFC) in 300 RPMI 8866 cells was determined in triplicate and was expressed as the average ±SD.

Rodent IgE-BF formed by the 12H5 cells were detected by the same procedure, except that rat IgE-coated ox erythrocytes were employed as indicator cells, and mesenteric lymph node cells of Lewis strain rate infected with Nippor-tronngylus brasiliensis were used as a source of FcεR$^+$B cells (Yodoi & Ishizaka, *J. Immunol*, 124: 1322,1980).

H. DETECTION OF GIF

GIF was detected by using T-cell hybridoma 12H5 cells (Iwata, et al., *J. Immunol.*, 140: 2534, 1988). A suspension of the hybridoma cells was mixed with an equal volume of a test sample, and the cell suspensions were cultured for 24 hours with 10 µg/ml mouse IgE. Culture supernatants were filtered through CF50A membranes, and filtrates containing IgE-BF were fractionated on lentil lectin Sepharose (Yodoi, et al., *J. Immunol.*, 125: 1436, 1980). Both unbound proteins (effluent fraction) and those eluted with 0.2M α methylmannoside (eluate fraction) were assessed for the presence of IgE-BF by rosette inhibition technique. When the 12H5 cells were cultured with mouse IgE alone, essentially all IgE-BF formed by the cells bound to lentil lectin Sepharose and were recovered by elution with α methylmannoside. Thus, the ratio of the percent rosette inhibition between the effluent/eluate fraction is less than 0.2. If a sufficient amount of GIF were added to the culture of 12H5 cells together with mouse IgE, the majority of IgE-BF formed by the cells lacked affinity for lentil lectin and were recovered in the effluent fraction (Iwata & Ishizaka, *J. Immunol.*, 141: 3270, 1988). Thus, GIF was taken as (+), if the ratio of the percent rosette inhibition between the effluent/eluate fraction were 3.0 or higher.

I. FRACTIONATION OF GIF

In order to determine whether GIF from hybridomas has affinity for bee venom PLA$_2$, culture filtrates of hybridoma cells were fractionated on antigen-coupled Sepharose. Hybridoma cells were treated with OKT 3 antibody (8 µg/ml) and 8 ml aliquots of the antibody treated or untreated cell suspension ($1.5 \times 10^6$ cells/ml) were cultured in anti-MGG-coated tissue culture flasks. Culture supernatants were concentrated four-fold, and a 2 ml sample was absorbed with 0.4 ml IgE-Sepharose. The effluent fraction was mixed with 0.5 ml PLA$_2$-Sepharose overnight, and immunosorbent was packed into a small column. After effluent fraction was recovered, the column was washed with DPBS, and then eluted with 1.0 ml glycine HCl buffer, pH 3.0. Partial purification of GIF on anti-lipomodulin (141B9) Sepharose was carried out by the procedures previously described (Akasaki, et al., *J. Immunol.*, 136: 3172, 1987).

J. DETERMINATION OF PHOSPHOLIPASE INHIBITORY ACTIVITY

Affinity-purified GIF was treated with alkaline phosphatase as previously described (Uede, et al., *J. Immunol*, 139: 898, 1983). Briefly 1 ml of the preparation was dialyzed against Tris-HCl buffer, pH 8.2 and was mixed with 1 unit of insoluble alkaline phosphatase (calf intestinal, Sigma) for 2 hours at room temperature. After centrifugation, the supernatant was dialyzed against 0.1M Tris-HCl buffer, pH 8.0. Phospholipase $A_2$ inhibitory activity of the alkaline-phosphatase treated samples was determined using *E coli* which were biosynthetically labeled with $^3$H-oleic acid and porcine pancreatic $PLA_2$ (Sigma) (Rothut, et al., *Biochem. Biophys. Res. Commun.*, 117: 878, 1983). Detailed procedures were described in Ohno, et al. (Internat. Immunol., 1: 425, 1989). Briefly, porcine pancreatic $PLA_2$ ($1\times10^{-5}$ units) was mixed with GIF in a total volume of 150 μl. After 5 minutes at 25° C., 50 μl of a suspension of $^3$H-labeled *E coli* (5000 cpm) was added, and the mixtures were incubated for 5 minutes at 25° C. The reaction was stopped by the addition of 50 μl 2M HCl, and 50 μl of 100 mg/ml BSA was added to the mixtures. The suspensions were centrifuged for 1 minute at 5500 g, and radioactivity in 250 μl of supernatant was measured in a scintillation spectrometer.

K. ION EXCHANGE COLUMN CHROMATOGRAPHY

Culture supernatant of AC5 cells in serum-free medium was concentrated 25 to 100 fold by ultrafiltration. After centrifugation at 10,000 rpm for 20 min, the supernatant was diluted 8-fold with distilled water, adjusted to pH 8.0 with Tris, and immediately applied to a DEAE-Sepharose CL-6B (Pharmacia) column (3 ml volume) which was equilibrated with 10 mM Tris HCl buffer, pH 8.0. After effluent (passed-through) fraction was recovered, the column was washed with 4 column volumes of 10 mM Tris-HCl buffer containing 20 mM NaCl, and the washing was combined to the passed through fraction. Proteins bound to the column were eluted successively with 4 column volumes of 10 mM Tris HCl buffer, pH 8.0 containing 50 mM, 75mM, 100 mM, 150 mM, and 200 mM NaCl. Each eluate fraction was concentrated and dialyzed against Dulbecco's phosphate buffered saline (DPBS).

L. GEL FILTRATION

One ml sample in DBPS was applied to a Superose 12 column (1.6×50 cm, Pharmacia), connected to HPLC (Beckman, System Gold). Proteins were eluted from the column with DPBS at a flow rate of 1 ml/min, and appropriate fractions were collected. The column was calibrated with human IgE (PS protein, MW: 185,000), bovine serum albumin (BSA, MW: 67,000), ovalbumin (MW: 43,000), soybean trypsin inhibitor (MW: 20,100), and cytochome C (MW: 12,500). All standard proteins except IgE were obtained from Sigma. Retention time for the standard proteins were 41.97, 52.08, 55.135, 62.097, and 71.67 min, respectively.

M. AFFINITY-PURIFICATION OF GIF

Culture supernatant of CL3 clone in complete DME medium was concentrated 5-fold by ultrafiltration, and GIF in the supernatant was absorbed to 141B9-Sepharose or anti-GIF Sepharose by recycling the supernatant overnight through the immunosorbent column (5 ml volume) (Iwata, et al., *J.Immunol.*, 141: 3270, 1988). The immunosorbent was washed with 20 column volumes of DPBS, and proteins bound to the beads were recovered by elution with 0.1M glycine HCl buffer, pH 3.0. Murine GIF from the 231 F1 cells was purified by the same technique using the 141B9-Sepharose.

In order to isolate GIF in culture supernatant of AC5 cells in protein-free medium, the supernatant was concentrated 50 to 100-fold by ultrafiltration. An appropriate fraction of the supernatant from a DEAE-Sepharose column was concentrated to 5–6 ml and mixed overnight at 4° C. with 1.0 to 1.5 ml of Affigel 10-immunosorbent coupled with monoclonal anti-GIF antibody. The suspension was packed into a small column and the immunosorbent was washed with 40 column volumes of DPBS. In some experiments, the immunosorbent was washed with 40 column volumes of DPBS and 20 column volumes of PBS containing 0.5M NaCl. Proteins bound to the immunosorbent were eluted with 0.05M glycine HCl buffer containing 0.15M NaCl, pH 3.0–3.2.

N. DETECTION OF GIF BY SDS-PAGE

Affinity-purified GIF was dialyzed against 0.01% SDS in deionized water, and lyophilized in a Speed vac (Savant Instruments, Hicksville, N.Y.). Samples were then analyzed by SDS gel electrophoresis in 15% polyacrylamide slab gel by using the Laemmli system (Laemmli, U.K., *Nature*, 227: 680, 1970). Gels were fixed and protein bands were detected by silver staining (Ochs, et al., *Electrophoresis*, 2: 304, 1981). Molecular weight standards were obtained from Pharmacia.

O. ELISA ASSAYS

In order to detect monoclonal anti-GIF antibody, the method described by Steele, et al. (*J.Immunol.*, 142: 2213, 1989) was employed with slight modifications. Briefly, Immulon I plates (Dynatech) were coated overnight with 100 μl of affinity-purified GIF diluted with 0.1M carbonate coating buffer, pH 9.6. Plates were washed 3 times with phosphate buffered saline (PBS) containing 0.05% Tween 20 between each of the following steps. Plates were blocked with 2% BSA in PBS for 6–9 hours. One hundred microliters of each test sample was then added to the well, and plates were kept overnight at 4° C. Binding of mouse Ig to the plate was detected by using alkaline phosphatase-coupled goat anti-mouse Ig (Zymed Lab, So. San Francisco, Calif.) and alkaline phosphatase substrate (Sigma). ELISA signal was read in a microplate reader MR 5000 (Dynatech Lab) with a 410 nm filter 30 min after the addition of substrate. Isotype of monoclonal antibodies was determined with ELISA assay by using an isotyping kit for mouse mAb (Zymed Lab).

For the detection of GIF in fractions of an affinity-purified GIF preparation, a biotin-avidin system and amplification method (Stanley, et al., *J.Immunol. Methods*, 83: 89, 1985) were employed to increase the sensitivity. Maxi-Sorp microtiter plates (Nunc, Copenhagen, Denmark) were coated with 50 μl of each fraction. After incubation for 2 hours at 37° C., plates were washed with Tween/PBS and blocked with 2% BSA overnight at 4° C. After washing, 50 μl of biotin-coupled mAb 141-B9 (200 ng/ml) were added to each well and the plate was incubated for 2 hours at 37° C. The plate was washed and 50 μl of a 1:1500 dilution of streptavidin-alkaline phosphatase conjugate (Zymed Lab) were added to each well. After incubation for 1 hour at 37° C., quantities of alkaline phosphatase bound to the wells were measured by amplification system (Stanley, et al., *J.Immunol. Methods*, 83: 89, 1985), (GIBCO-BRL, Bethesda, Md.). ELISA signal was determined at 490 nm.

EXAMPLE 2

CHARACTERIZATION OF HYBRIDOMAS PRODUCING HUMAN ANTIGEN-SPECIFIC GIF

As described above, PBMC of a bee venom-sensitive patient were cultured for three days in the presence of 10 μg/ml D-$PLA_2$, and activated T-cells were propagated by IL-2 for four days in the presence of 3 μl/ml recombinant lipocortin. T-cells were then fused with BUC cells to construct hybridomas. In this experiment, 4 hybridoma clones were obtained. Each hybridoma clone was cultured in complete DMEM and culture supernatants were filtered through YM100 membranes. Filtrates were concentrated ten-fold and assessed for the presence of GIF by using the 12H5 cells. The results shown in Table I indicate that two of the four hybridoma clones constitutively secrete GIF.

TABLE I

Selection of GIF-Producing Hybridomas

| Hybridoma | GIF Activity[a] Effluent/Eluate | $^3$H-Oleic Acid Release[c] Release (cpm) | Inhibition (%) |
|---|---|---|---|
| Cl 1 | 0/26 (−) | ND | — |
| Cl 2 | 2/33 (−) | 390 ± 27 | 4 |
| Cl 3 | 29/0 (+) | 257 ± 25 | 37 |
| Cl 7 | 27/5 (+) | 303 ± 17 | 26 |
| Control | 0/31[b] | 408 ± 15 | — |

[a]Culture filtrates of each clone were concentrated ten-fold. One volume of the filtrate was added to an equal volume of a suspension of the 12H5 cells, and the cells were cultured for 24 hours in the presence of 10 μg/ml mouse IgE. Numbers in the column represent the percent of rosette inhibition by the effluent/eluate fractions from lentil lectin Sepharose. The proportion of IgE-RFC in the absence of IgE-BF was 24.4 ± 0.3 (SD)%.
[b]The 12H5 cells were cultured with 10 μg/ml mouse IgE alone, and IgE-BF in culture filtrates were fractionated on lentil lectin Sepharose.
[c]Culture filtrates were fractionated on 141B9-Sepharose, and acid eluates from the immunosorbent were concentrated to 1/100 volume of the original culture supernatant. The samples were treated with alkaline phosphatase, and dephosphorylated materials were assessed for the ability to inhibit pancreatic phospholipase A2.

The presence of CD3 determinants on the hybridoma clone CL3 was assessed by fluorocytometry and the rosetting technique. The cells were treated with 8 μg/ml monoclonal antibody OKT3 and then stained with fluoresceinated goat anti-mouse Ig. Less than 10% of the total cells were stained. It was also found that only 6–8% of the OKT3-treated cells formed rosettes with anti-MGG-coupled erythrocytes. As a consequence, the CD3$^+$ cells were enriched using the rosetting procedures described in Example 1. Cells which formed rosettes with anti-MGG coupled erythrocytes were separated from non-rosetting cells by density gradient centrifugation on Percoll layers and were expanded by culture in complete DMEM. The same procedures were repeated three times to enrich the CD3$^+$ cell population. Treatment of the final cell preparation with OKT3 antibody followed by incubation with anti-MGG-coated erythrocytes showed that 80–90% of the cell population formed rosettes. Approximately 75% of the cells were stained by OKT3 in cytofluorometry. However, when culture of the cells for 2 weeks with four passages resulted in the decline of CD3$^+$ cells to approximately 52% (as determined by cytofluorometry), the CD3$^+$ cell population was further enriched by cell sorting and expanding the cells by culture. After repeating the cell sorting twice, a CL3 population was obtained which stably expressed CD3. Fluorescent staining of the population with OKT3 and WT31 (anti-TcRαβ) indicated that essentially 100% of the cells expressed CD3 and the majority of the cells expressed TcRαβ. The CD3$^+$ cell population and CD3$^-$ population were cultured and culture filtrates were assessed for the presence of GIF by using the 12H5 cells. The GIF activity was detected in culture filtrates of CD3$^+$ cells, but not in the culture filtrates of CD3$^-$ population. The results indicated that the source of GIF is CD3$^+$ cells.

Since one of the unique properties of mouse GIF is that the monoclonal anti-lipomodulin (141B9) binds the lymphokine, it was decided to determine whether human GIF from the CL3 cells would be absorbed with 141 B9-coupled Sepharose. The CD3$^+$, CL3 clone was cultured to yield 1 liter of culture supernatant. After filtration through a YM100 membrane, the filtrates were concentrated to 5 ml, and fractionated on 1 ml 141-B9 Sepharose. After recovering the effluent fraction, the immunosorbent column volumes of 10 column volumes of DPBS, and then eluted with 5 column volumes of glycine-HCl buffer, pH 3.0. After dialysis against DPBS, distribution of GIF activity in the fractions was determined by using the 12H5 cells. The results shown in Table II indicate that essentially all GIF activity in the culture filtrate bound to 141-B9 Sepharose and was recovered by elution at acid pH.

TABLE II

Human GIF From CL3 Clone Purified By Affinity Chromatography On Anti-Lipomodulin Sepharose[a]

| Fraction from 141B9-Sepharose[b] | Dilution | GIF Activity[c] Effluent/Eluate |
|---|---|---|
| Effluent | 1:10 | 0/31 (−) |
| Washing | 1:10 | 0/35 (−) |
| Eluate | 1:10 | 42/0 (+) |
|  | 1:40 | 45/0 (+) |
|  | 1:80 | 39/0 (+) |
| Media Control | — | 0/34 |

[a]Culture supernatants of the CL3 clone were filtered through YM100 membranes, and filtrates were concentrated 200-fold. 5 ml of the concentrated filtrate was fractionated on 1 ml 141B9-Sepharose.
[b]After recovering the effluent fraction, the immunosorbent was washed with 5 column volumes of DPBS, and then eluted with 5 column volumes of glycine HCl buffer, pH 3.0.
[c]GIF activity was assessed by using the 12H5 cells by the same procedures described in Table I. Numbers in the column represent percent rosette inhibition by the effluent/eluate fractions from lentil lectin Sepharose. The proportion of IgE-RFC in the absence of IgE-BF was 22.9 ± 0.6 (SD) % in this assay. (+) indicated the presence of GIF.

Previous experiments provided evidence that murine GIF is a phosphorylated derivative of a phospholipase inhibitory protein (Uede, et al., *J. Immunol.*, 139: 898, 1983). Thus, GIF in the culture filtrates of CL3 clone was purified by using the 141B9-Sepharose. Culture filtrate of the three other clones, CL1, CL2, and CL7 were fractionated on the 141B9-Sepharose in a similar manner. The acid eluates from the immunosorbent were treated with alkaline phosphatase, and assessed for the ability to inhibit the release of $^3$H-oleic acid from biosynthetically labeled *E. coli* by pancreatic phospholipase A$_2$ (Rothut, et al., *Biochem. Biophys. Res. Commun.*, 117: 878, 1983). The results included in Table I indicate that the affinity-purified GIF from CL3 and CL7 exerted phospholipase inhibiting activity, while the same fraction from CL1 and CL2 failed to inhibit phospholipase A$_2$.

EXAMPLE 3

ANTIGEN-BINDING PROPERTIES OF GIF

Previous experiments have shown that antigen-activated T-cells propagated with IL-2 in the presence of lipocortin constitutively released GIF that had no affinity for bee venom PLA$_2$, but cross-linking of CD3 on the same cells resulted in the formation of GIF having affinity for the antigen-coupled Sepharose together with IgE-BF (Carini, et al., *J. Immunol. Meth.* 127: 221, 1990). In view of these findings, it was decided to determine whether the CL3 clone produces antigen-binding GIF and IgE-BF. The cells were treated with OKT3 at 0° C., and the antibody-treated cells (1.5×10$^6$ cells/ml) were cultured in the anti-MGG-coated cells. As a control, untreated CL3 cells were cultured in the anti-MGG-coated wells. Culture supernatants were filtered through YM100 membranes and concentrated seven-fold by ultra-filtration. The concentrated culture filtrates were absorbed overnight with 1 ml IgE-Sepharose, and unbound protein fraction and 2 ml of washings were combined. The IgE-Sepharose was thoroughly washed, and eluted with glycine HCl buffer. The eluate fractions from IgE-Sepharose were assessed for the presence of IgE-BF by using RPMI 8866 cells as the source of $FceR^+$ cells.

TABLE III

Failure Of The GIF From The CL3 Clone To Bind To Bee Venom $PLA_2$

| Treatment[a] | IgE-BF[b] (%) | GIF Activity In $PLA_2$-Sepharose[c] | | |
|---|---|---|---|---|
| | | Eluate | Washing | Eluate |
| OKT 3 | 23 | 34/0(+) | 21/0 (+) | 0/24(−) |
| None | 0 | 28/0(+) | 22/13(±) | 0/26(−) |

[a]Untreated or CD3-treated cells were cultured in anti-MGG-coated wells.
[b]30 ml culture supernatant were filtered through YM100, and filtrates were concentrated to 4 ml. The samples were absorbed with 1.0 ml IgE-Sepharose. Acid eluate fraction was adjusted to 4.0 ml and assessed for IgE-BF by rosette inhibition. The proportion of IgE-BF in the absence of IgE-BF was 37.7 ± 1.0%.
[c]1.0 ml of the effluent fraction from IgE-Sepharose was fractionated on $PLA_2$-Sepharose. The effluent, washing and acid eluate fractions were adjusted to 1.3 ml, and were assessed for GIF activity by using the 12H5 cells. Numbers in the column represent percent rosette inhibition by the effluent/eluate fractions from lentil lectin Sepharose. The proportion of IgE-RFC in the absence of IgE-BF was 21.7 ± 0.6 (SD) %.

The results shown in Table III indicate that anti-CD3-treated cells formed IgE-BF, while untreated cells failed to produce a detectable amount of IgE-BF. The effluent fraction from IgE-Sepharose was concentrated two-fold and 1 ml samples were fractionated on 0.25 ml $PLA_2$-Sepharose. The effluent fraction, washing, and eluate fraction were adjusted to 1.5 ml, and the samples assessed for GIF activity. As shown in Table III, GIF from both unstimulated and anti-CD3 treated cells failed to bind to $PLA_2$-Sepharose.

It was thought that the failure of the GIF from anti-CD3 treated CL3 cells to bind $PLA_2$ might be related to the use of $D-PLA_2$ for the activation of T-cells. In order to investigate this possibility, more T-cell hybridomas from PBMC of a bee venom sensitive patient were constructed. The protocol for the construction of T-cell hybridomas was exactly the same as that described above, except that PBMC were stimulated with 10 µg/ml CNBr-treated $PLA_2$ instead of $D-PLA_2$. As the results of this experiment, 22 hybridoma clones were obtained. The GIF assay of culture filtrates of each clone indicated that 10 out of 22 clones constitutively formed GIF (results not shown). Seven GIF-secreting clones were treated with OKT3 and the antibody-treated cells were cultured in anti-MGG-coated dishes. Culture filtrates were concentrated four-fold and absorbed with IgE-Sepharose.

TABLE IV

Formation Of Antigen-Binding GIF By Anti-CD3-Treated Hybridoma Cells[a]

| Clone | IgE-BF[b] (%) | GIF Activity in $PLA_2$-Sepharose[c] | |
|---|---|---|---|
| | | Effluent | Eluate |
| AC5 | 20 | 0/21 (−) | 31/0 (+) |
| AF10 | 36 | 19/0 (+) | 0/21 (−) |
| BA6 | 8 | 29/0 (+) | 0/24 (−) |
| BE12 | 65 | 0/31 (−) | 25/0 (+) |
| BF5 | 65 | 0/27 (−) | 20/0 (+) |

TABLE IV-continued

Formation Of Antigen-Binding GIF By Anti-CD3-Treated Hybridoma Cells[a]

| Clone | IgE-BF[b] (%) | GIF Activity in $PLA_2$-Sepharose[c] | |
|---|---|---|---|
| | | Effluent | Eluate |
| CB7 | 64 | 0/28 (−) | 17/0 (+) |
| CE5 | 58 | 0/28 (−) | 35/0 (+) |

[a]$1.2 \times 10^7$ cells were treated with OKT 3. Cells were resuspended in 8 ml culture medium and seeded in an anti-MGG-coated flask. Culture supernatant were concentrated four-fold and absorbed with IgE-Sepharose. Effluents from IgE-Sepharose were then fractionated on $PLA_2$-Sepharose and GIF activity in the effluent and eluate fraction was determined.
[b]Acid eluate fractions from IgE-Sepharose were assessed for the presence of IgE-BF. The proportion of IgE-RFC in the absence of IgE-BG was 26.3 ± 0.6 (SD) %.
[c]GIF activity was determined by using the 12H5 cells. Numbers represent the percent rosette inhibition by the effluent/eluate fractions from lentil lectin Sepharose. Proportion of IgE-RFC in the absence of IgE-BF was 26.0 ± 0.7 (SD) %. (+) indicates the presence of GIF.

As shown in Table IV, acid eluate fraction from IgE-Sepharose of 6 out of 7 clones contained detachable amounts of IgE-BF. The effluent fractions from IgE-Sepharose were then fractionated on $PLA_2$-Sepharose, and the effluent and eluate fractions from the immunosorbent were assessed for GIF activity. The results shown in Table IV indicate that the majority of GIF from 5 out of 7 clones bound to $PLA_2$-Sepharose and recovered by elution at acid pH. In order to confirm that cross-linking of CD3 is required for these clones to produce antigen-binding GIF, the 5 clones were cultured in anti-MGG-coated cells without treatment with anti-CD3. As expected, culture supernatants did not contain IgE-BF, and GIF in the supernatant failed to bind to $PLA_2$-Sepharose.

The present invention provides a technique to allow the development of GIF-producing T-cell populations from PBMC of patients allergic to bee venom $PLA_2$, and to establish GIF-producing hybridomas from the T-cells. Representative hybridomas express CD3 determinants and TCRαβ, indicating that they are T-cell hybridomas. Furthermore, the TcR complex on the hybridomas appears to be functional. Both parent T-cells (Carini, et al., *J. Immunol. Methods*, 127: 221, 1990) and the majority of the GIF-producing hybridomas (Tables III, IV) produced IgE-BF upon cross-linking of CD3. Cross-linking of TcRαβ or CL3 and AC5 clones by the monoclonal antibody WT31 and anti-MGG also resulted in the formation of IgE-BF (results not shown). Further testing of representative $CD3^+$ hybridomas showed that all of the CL3, BE12, AC5 and CB7 clones expressed both CD4 and CD8. Since BUC cells employed for construction of the hybridomas are $CD4^+$ $CD8^-$ (personal communication from Dr. J. Stobo), it is not clear whether the parent T-cells of the hybridomas co-expressed both CD4 and CD8.

The present experiments showed that some of the T-cell hybridomas produced antigen($PLA_2$)-binding GIF upon cross-linking of CD3 on the cells. This finding is in agreement with the fact that representative murine GIF-forming hybridomas formed antigen-binding GIF upon stimulation with antigen-pulsed syngeneic macrophages or by cross-linking of CD3 on the cells (Iwata & Ishizaka, *J. Immunol*, 141: 3270, 1988, Iwata, et al., *J. Immunol.*, 143: 3917, 1989), and suggested similarities between the antigen-binding GIFs from the two species. In the murine system, the antigen-binding GIF obtained from the hybridomas suppressed the in vivo antibody response in carrier (antigen)- specific manner. It was also found that the antigen-binding GIF from the hybridomas were composed of antigen-binding polypeptide chain and non-specific GIF (Jardieu and Ishizaka, in *Immune Regulation by Characterized Polypeptides*, G. Goldstein, et al., ed., Alan R. Liss, New York, p.595, 1987), and that the antigen-binding chain shared a common antigenic determinant 14-12 with those of the effector type suppressor T-cell factor (TseF) (Iwata, et al. ibid, 1989). Separate experiments have shown that both the monoclonal anti-lipomodulin antibody 141-B9 and anti-I-J antibodies bound not only GIF, but also non-antigen binding chain (I-J$^+$ chain) of TseF and TsiF (Jardieu, et al., *J. Immunol.*, 138: 1494, 1986, Steele, et al., *J. Immunol.*, 142: 2213, 1989). These findings collectively suggest that the antigen-binding GIF is identical to TseF. Parent T-cells of a representative murine Ts hybridoma 71B4 were obtained by stimulation of OVA-primed spleen cells by homologous antigen, followed by propagation of the antigen-activated T-cells in the presence of GIF. (Iwata & Ishizaka, *J. Immunol.*, 141: 3270, 1988). The same strategy was employed to obtain the parent cells of the human T-cell hybridomas in the present experiments. Indeed, both non-specific GIF and PLA$_2$-binding GIF from the human hybridomas bound to 141B9-Sepharose which previous studies had shown could also absorb murine TsFs (Steele, et al., *J. Immunol.*, 142: 2213, 1989). It could be that PLA$_2$-binding GIF from the human T-cell hybridomas represents human antigen-specific TseF. However, it is still possible that the antigen-binding GIF may be a counterpart of murine TsiF. Recent experiments in our laboratory have shown that the typical murine helper T-cell clone D10.G4.1 can produce antigen-binding GIF, if the cells were precultured in the presence of a phospholipase A$_2$ inhibitor, and then stimulated with antigen(conalbumin)-pulsed antigen-presenting cells (Ohno, et al., *Internat. Immunol*, 2: 257, 1990). It was also found that this antigen-binding GIF bound to the monoclonal antibody 14-30, which is specific for TsiF (Ferguson and Iverson, *J. Immunol.*, 136: 2896, 1986), rather than the monoclonal antibody 14-12. Green, et al., (*J. Mol. Cell Immunol.*, 3: 95, 1987) also reported that D10.G4.1 clone produced antigen-binding TsF upon antigenic stimulation with UV-irradiated antigen-pulsed macrophages, and that this factor, together with accessory molecules, induced the generation of the effector type, antigen-specific Ts. Since PBMC from allergic patients contain helper T-cells, it is still possible that the antigen-binding GIF from the human hybridomas represents TsiF rather than TseF.

Takeuchi, et al., (*J. Immunol*, 141: 3010, 1988) established Ts clones from PBMC of KLH-primed individuals, who had received repeated injections of a large dose of homologous antigen. Modulin, et al., (*Nature*, 322: 459, 1986) also established Ts clones from lesions of lepromatous leprosy patients. However, prior to the present invention, effector molecules mediating suppressor activity (TsF) from human Ts cells have not been identified. Similarities between human GIF and mouse GIF suggest that the PLA$_2$-binding GIF from human T-cell hybridomas may represent TsF from human suppressor T-cells. The T-cell hybridomas, which produce antigen-binding GIF, will facilitate biochemical characterization of the molecules. It has been repeatedly shown in the mouse that Ts as well as TsF (antigen-binding GIF) suppressed the in vivo IgE antibody response more effectively than the IgG antibody response (Ishizaka, et al., *J. Immunol.*, 114: 110, 1975). If the allergen-binding GIF from the human T-cell hybridomas actually represent TsF, it is a reasonable expectation that the T-cell factor may suppress the IgE antibody response of the donor of parent T-cells.

EXAMPLE 4

PREPARATION OF HYBRIDOMA CELL LINES PRODUCING CEDAR POLLEN-SPECIFIC GIF

Japanese cedar pollen is a major allergen in Japan and causes seasonal allergic rhinitis and conjuctivitis in a large percentage of the population. In order to further test the general applicability of the teachings of the invention to other antigens, the methods for generating antigen-specific GIF-producing T-cells and T-cell hybridomas (described above) were applied to peripheral blood mononuclear cells from patients allergic to Japanese cedar allergen.

The major allergen in Japanese cedar (Sugi, *Cryptomeria japonica*) is a 40 kDa glycoprotein designated cryj-1 (Yasueda, et al., *J. Allergy and Clin. Immunol.*, 71: 77, 1983). For these studies, the allergen was isolated from extracts of cedar pollen by this method with slight modifications. Briefly, pollen was defatted with ether, and extracted 3 times with 0.125M ammonium bicarbonate. Carbohydrate in the extracts were removed by hexadecyltrimethyl ammonium bromide. Proteins in the extracts were precipitated with 80% saturated ammonium sulfate, and the precipitate dissolved in 0.05M Tris-HCl buffer, pH 7.8. After extensive dialysis against the Tris-HCl buffer, the protein fraction was applied to a DEAE cellulose column (DE-52, Whatman), and a flow-through fraction was obtained. The fraction was concentrated, dialyzed against 0.01M acetate buffer, pH 5.0, and applied to a CM cellulose column (CM-52, Whatman), which was equilibrated with the buffer. The column was washed with the buffer, and proteins retained in the column eluted with 0.1M phosphate buffer containing 0.3M sodium chloride. Proteins in the eluate were further fractioned by gel filtration through a Sephacryl S-200 HR column to obtain a major protein fraction containing cryj-1. The major protein in the fraction was 42 kDa as determined by SDS-polyacrylamide gel electrophoresis, and N-terminal amino acid sequence of the protein was identical to that of cryj-1. The protein was conjugated to Affigel 10 at 1.5 mg/ml gel.

A synthetic phospholipase A$_2$ inhibitor, 2-(p-amylcinnamoyl)-amino-4-chlorobenzoic acid, (ONO-RS-082, ONO Pharmaceutical Co.) was used instead of recombinant human lipocortin I. Previous experiments had shown that ONO-RS-82 is a specific inhibitor of phospholipase A$_2$ and facilitates the generation of GIF-producing cells in mouse spleen cell cultures (Ohno, et al., *International Immunology*, 1: 425, 1989). When spleen cells of ovalbumin-primed mice were stimulated with ovalbumin, and antigen-activated T-cells were propagated with IL-2 in the presence of either 2 µM ONO-RS-082, or 3 µg/ml recombinant human lipocortin I, GIF-producing, antigen-specific T-cells were generated. Antigen stimulated T-cells and construction of T-cell hybridomas were carried out essentially the same as described above, except that purified cryj-1 was used as antigen, and ONO-RS-082 was employed as a phospholipase A$_2$ inhibitor. Thus, mononuclear cells were obtained from peripheral blood of patients allergic to Japanese cedar pollen, and suspended in RPMI 1640 medium containing 10% fetal calf serum (FCS). A suspension of the mononuclear cells (3×10$^6$ cells/ml) were cultured for 3 days in the presence of 10 µg/ml cryj-1. Non-adherent cells were recovered, resuspended in RPMI medium containing 10% FCS, (3×10$^5$ cells/ml), and cultured for 4 days in the presence of 60 units/ml human IL-2 and 2 µM ONO-RS-082. Cells propagated in this manner were then recovered and fused with BUC cells to construct hybridomas.

Hybridomas were treated with the monoclonal anti-CD3 antibody SPB-T3b (Spits, et al., Hybridoma 2: 423, 1983), and the presence of CD3 on the cells were tested by immunofluorescence. Only CD3+ hybridomas were subcloned by limiting dilution.

The CD3+ hybridoma clones were maintained in complete DME medium containing 10% FCS, and culture supernatant of each clone was assessed for the presence of GIF by using the 12H5 cells. Results obtained with hybridomas from one patient are shown in Table V. GIF activity was detected in culture supernatants of three hybridomas; 31E9, 31B7, and 32B4. Supernatants of the other two hybridomas, 31H6 and 31H3, appear to have weak GIF activity. Thus, the GIF-producing hybridomas were treated with anti-CD3 antibody followed by anti-mouse immunoglobulin, and the cells were cultured for 24 hr. Culture supernatants were then fractionated on cryj-1 coupled immunosorbent. The presence of GIF activity in the flow-through fraction and the acid-eluate fraction from the immunosorbent was assessed by using the 12H5 cells. The results included in Table V indicate that GIF from the 31E9 cells bound to cryj-1-Affigel and could be recovered by elution at acid pH, whereas GIF from the 31B7 cells failed to bind to the antigen-coupled immunosorbent. The results indicate that the 31E9 cells produce GIF having affinity for cryj-1, upon stimulation with anti-CD3.

TABLE V

PRODUCTION OF HUMAN CEDAR ALLERGEN-SPECIFIC HYBRIDOMAS[a]

| Hybridoma Clone | % rosette inhibition[b] (effluent/eluate) | GIF activity in cryj-1 Sepharose[c] | |
|---|---|---|---|
| | | unbound | bound |
| none | 0/23 | 0/29 | — |
| 31H6 | 20/13(±) | 5/20 (−) | 12/10(±) |
| 31A11 | 0/25 (−) | ND | — |
| 31E9 | 28/5(+) | 0/22 (−) | 20/0(+) |
| 31H3 | 23/12(±) | 0/34 (−) | 38/16(±) |
| 31B7 | 32/5(+) | 20/5(+) | 4/24 (−) |
| 31F7 | 0/26 (−) | ND | — |
| 32B4 | 22/0(+) | 22/14(±) | 38/22(±) |

[a]Hybridomas in this table were derived from two separate experiments.
[b]Culture supernatants of unstimulated hybridomas were screened for the presence of GIF. Aliquots of 12H5 cells were incubated with culture supernatant of each hybridoma in the presence of mouse IgE. Culture supernatants of the 12H5 cells were filtered through CF50A to remove IgE, and filtrates were fractionated on lentil lectin Sepharose. IgE-BF in the effluent and eluate fractions was assessed by rosette inhibition. Numbers in the column represent the percent rosette inhibition by the effleunt/eluate fractions from lentil lectin Sepharose. (+)(−) signs indicate the presence or absence of GIF, respectively.
[c]Representative hybridomas were treated with anti-CD3 antibody and culture supernatants were fractionated on cryj-1 coupled Affigel. The presence of GIF activity in the flow-through (unbound) fraction, and acid eluate (bound) fraction was determined by using 12H5 cells. Culture filtrates of the 12H5 cells were fractionated on lentil lectin Sepharose. Numbers represent percent rosette inhibition by the effluent/eluate fractions from lentil lectin Sepharose. GIF from the 31E9 cells bound to-Affigel and was recovered by elution at acid pH, while GIF from the 31B7 cells failed to be retained in the cryj-1-Affigel column.

EXAMPLE 5

PREPARATION AND CHARACTERIZATION OF HYBRIDOMA CELL LINES PRODUCING MONOCLONAL ANTIBODIES SPECIFIC FOR HUMAN GIF

A. CONSTRUCTION AND SCREENING OF HYBRIDOMAS

Human GIF in culture supernatant of the T-cell hybridoma CL3 was purified by using anti-lipomodulin (141-B9)-Sepharose. The affinity-purified GIF was mixed in complete Freund's adjuvant, and BALB/c mice were immunized by intraperitoneal injections of the antigen, given 3 times at 2 week intervals. Two weeks after the last immunization, spleen cells of the immunized mice were obtained, and $1 \times 10^7$ spleen cells were transferred into syngeneic BALB/c mice which had been irradiated with 625R γ ray. The recipients were immunized immediately after cell transfer and 2 weeks later with purified GIF included in incomplete Freund's adjuvant. One week after the booster, their spleen cells were fused with HPRT-deficient B cell line SP 2/0-14AG. The cells were cultured in HAT medium with BALB/c macrophages as feeder layer. One hundred and two hybridoma clones obtained in the culture were selected for the formation of mouse immunoglobulin, and Ig-forming hybridomas were selected for anti-GIF antibody production by ELISA assay, followed by bioassay using the 12H5 cells.

In ELISA assay, Immulon I plates (Dynatech) were coated with affinity-purified GIF. Control wells were filled with DPBS. After blocking the wells with 2% BSA, culture supernatants were applied to each well, and the binding of mouse Ig to the wells was determined by using alkaline-phosphatase-coupled anti-mouse Ig antibodies. As shown in Table VI, culture supernatants of 11 hybridoma clones gave a significant ELISA signal.

TABLE VI

Selection of Anti-GIF-Producing Hybridomas[a]

| Hybridoma Ig Clone | Isotype | ELISA Signal/Control[b] | GIF Activity[c] Effluent/Eluate |
|---|---|---|---|
| none | — | 0/0 | 29/1 (+) |
| 334F | IgM | 0.195/0.003 | 33/1 (+) |
| 355C | IgM | 0.388/0.012 | 28/0 (+) |
| 338H | IgM | 0.316/0.050 | 0/29 (−) |
| 318H | IgM | 0.149/0.046 | 0/31 (−) |
| 388F | IgG | 0.892/0.100 | 0/28 (−) |
| 476B[1] | IgM[2a] | 0.100/0.020 | 0/20 (−) |
| 489G | IgM | 0.174/0.00 | 7/15 (?) |
| 481F | IgM | 0.460/0.092 | 18/0 (+) |
| 335C | IgM | 0.203/0.073 | 0/27 (−) |
| 419A | IgM | 0.542/0.15 | 27/1 (+) |
| 312F | IgM | 0.533/0.029 | 14/8 (±) |
| Medium Control | — | 0/0 | 0/31 |

[a]Culture supernatants, which were positive in the ELISA assay, were assessed for the ability to bind GIF from CL3 clone.
[b]Binding of mouse Ig in culture supernatants of the hybridomas to GIF-coated wells, as compared with nonspecific binding of Ig in the same supernatants to BSA-coated wells. Optical density at 410 mµ.
[c]Mixtures of purified GIF with culture supernatants of hybridomas were filtered through YM100 membranes, and the filtrates were assessed for GIF activity. The 12H5 cells were cultured with mouse IgE in the presence of the filtrate. IgE-BF formed by the cells was fractionated on lentil lectin Sepharose and IgE-BF in the effluent and eluate fractions from the lectin-coupled Sepharose were assessed by rosette inhibition. Numbers represent the percent rosette inhibition by the effluent-eluate fractions. GIF switched the nature of IgE-BG formed by the cells (top column vs. bottom column). (+) indicates the presence of GIF.

The presence of anti-GIF in the culture supernatants of the 11 hybridoma clones was then determined by using the 12H5 cells (Iwata, et al., J. Immunol., 140: 2534, 1988). The globulin factor of culture supernatant from each clone was obtained by precipitation with 50% saturated ammonium sulfate. After dialysis against phosphate buffered saline, the fraction was adjusted to 1/5 volume of the original culture supernatant. Aliquots of an affinity-purified GIF prepared from CL3 clone using 141B9 Sepharose. These aliquots were mixed with an equal volume of the globulin fraction from each clone, and the mixtures were incubated overnight at 4° C. The mixtures were then filtered through YM100 membranes, and the presence of GIF in the filtrates was assessed. Then, aliquots of a suspension of the 12H5 cells were mixed with an equal volume of the filtrate, and the cell suspensions were cultured for 24 hours in the presence of 10 µg/ml mouse IgE. The culture supernatants were filtered through CF50A membranes to remove IgE, and IgE binding factors in the filtrates were fractionated on lentil lectin Sepharose. The results of the experiments, included in Table VI, indicate that GIF was removed by the culture supernatants of 338H, 318H, 388F$_1$, 476B, and 335C clones, indicating that these hybridomas produce anti-GIF.

B. PURIFICATION OF HUMAN GIF WITH MONOCLONAL ANTI-GIF

Among the six hybridoma clones which produced monoclonal antibodies to GIF, only 388F$_1$ produced IgG antibody. This hybridoma was subcloned and cultured in high glucose Dulbecco's medium supplemented with 5% FCS. Culture supernatants were concentrated by ultra filtration and IgG in the supernatants was recovered by using Protein A-Sepharose. The monoclonal antibody was then coupled to Tresyl-activated Sepharose to prepare immunosorbent. In order to determine whether the monoclonal antibody could bind the same molecules as those bound to anti-lipomodulin (141B9) Sepharose, GIF in culture supernatant was absorbed with 141-B9-Sepharose, and was recovered by elution at acid pH. The affinity-purified GIF preparation was then fractionated with anti-GIF (388F$_1$)-coupled Sepharose. After the effluent fraction was obtained, the immunosorbent column was washed with 10 column volumes of Dulbecco's phosphate buffered saline (DPBS), and then eluted with glycine HCl buffer, pH 3.0. A serial dilution of the effluent and eluate fractions were assessed for GIF activity by using the 12H5 cells. The results shown in Table VII indicate that GIF in the acid eluate fraction from 141B9-Sepharose bound to the anti-GIF (388F$_1$)-Sepharose and was recovered again by elution at acid pH. The results indicate that both anti-lipomodulin and anti-GIF bind human GIF.

TABLE VII

Fractionation of Partially Purified Human GIF on the Anti-GIF (388F$_1$) Coupled Sepharose[a]

| Fraction from 388F$_1$-Sepharose | Dilution | GIF Activity[b] Effluent/Eluate |
|---|---|---|
| Effluent | 1:10 | 0/35 (−) |
|  | 1:20 | 0/29 (−) |
| Eluate | 1:20 | 39/0 (+) |
|  | 1:40 | 26/0 (+) |
| Unfractionated | 1:40 | 27/0 (+) |
| Media Control |  | 0/27 |

[a]GIF in culture supernatants of CL-3 clone was purified by using the anti-lipomodulin Sepharose. The affinity purified GIF (1.5 ml) was fractionated on 0.75 ml of 388F$_1$-coupled Sepharose. After recovering the effluent fraction, the column was washed with 10 column volumes of DPBS, and then eluted with 3 column volumes of glycine HCl, pH 3.0.

TABLE VII-continued

Fractionation of Partially Purified Human GIF on the Anti-GIF (388F$_1$) Coupled Sepharose[a]

| Fraction from 388F$_1$-Sepharose | Dilution | GIF Activity[b] Effluent/Eluate |
|---|---|---|

[b]GIF activity was assessed by using the 12H5 cells by the same procedures described in Table IV. Numbers in the column indicate the percentage rosette inhibition by the effluent/eluate fractions from lentil lectin Sepharose. (+) indicates the presence of GIF.

In order to determine if the anti-human GIF could bind mouse GIF, mouse GIF from Ts hybridoma, 231F$_1$ cells were purified by using 141B9-Sepharose, and aliquots of the purified mouse GIF were fractionated on either 141B9-Sepharose or 388F$_1$-Sepharose. After the effluent fractions were obtained, immunosorbents were washed with 3 column volumes of DPBS, and then eluted with 3 column volumes of glycine HCl buffer, pH 3.0. As expected, all GIF activity was absorbed to 141B9 Sepharose, and recovered by elution at acid pH. Neither the effluent nor washing fraction contained GIF activity. When the same GIF preparation was fractionated on 388F$_1$-Sepharose, weak GIF activity was detected in the effluent fraction. The majority of the activity was detected in washings with DPBS, but the acid eluate fraction did not contain a detectable GIF activity. It appears that mouse GIF bind to anti-human GIF with extremely low affinity, and disassociate from the immunosorbent by washing at neutral pH. These results indicate that the monoclonal antibody 388F$_1$ is specific for human GIF.

C. PURIFICATION OF HUMAN GIF BY ION EXCHANGE CHROMATOGRAPHY

AC5 cells were subcloned by limiting dilution and CD3$^+$ clones obtained. These cells were then adjusted to serum-free ABC medium. Expression of CD3 on the subclones cultured in the medium was confirmed by fluorocytometry. Culture supernatants of CD3$^+$ subclones were concentrated 10–30 fold, and GIF activity in serial dilutions of the preparations was determined. Based on these results, subclone (AC5-23) was selected, since a 1:3 dilution of the 10-fold concentrated supernatant of this subclone could switch the 12H5 cells from the formation of glycosylated IgE-BF to the formation of unglycosylated IgE-BF.

Studies were done to determine whether human GIF could be purified by ion-exchange column chromatography. Culture supernatant of the AC5 subclone in ABC medium was concentrated 25-fold. A 10 ml aliquot of the concentrated culture supernatant was adjusted to pH 8.0 with Tris, diluted 8-fold with distilled water, and then applied to a DEAE-Sepharose column. Proteins bound to the column were eluted with 10 mM Tris buffers containing increasing concentrations of NaCl. Each fraction was concentrated to 10 ml and assessed for GIF activity.

TABLE VIII

Distribution of GIF Activity in DEAE-Sepharose Fractions

| Fraction | Tris HCl + NaCl (mM) [a] | Protein Content (µg) [b] | GIF ACTIVITY[c] |
|---|---|---|---|
| 1 | 20 | 65.5 | 21/0(+) |
| 2 | 50 | 35.0 | 20/6 (+) |
| 3 | 75 | 42.5 | 7/20 (−) |
| 4 | 100 | 38.5 | 3/19 (−) |
| 5 | 150 | 41.5 | 0/21 (−) |
| 6 | 200 | 42.0 | 0/20 (−) |

TABLE VIII-continued

Distribution of GIF Activity in DEAE-Sepharose Fractions

| Fraction | Tris HCl + NaCl (mM) [a] | Protein Content (μg) [b] | GIF ACTIVITY [c] |
|---|---|---|---|
| medium control | | | 0/22 (−) |

[a] Concentrated culture supernatants of the AC5 cells were diluted 8-fold with distilled water, and applied to DEAE-Sepharose column. Fraction 1 represents passed through fraction combined with washing with 10 mM Tris HCl pH 8.0 containing 20 mM NaCl. The column was eluted stepwise with 10 mM Tris hCl containing increasing concentrations of NaCl.
[b] Total protein recovered after concentration of each fraction. After elution with Tris buffer containing 200 mM NaCl, much protein retained in the column.
[c] GIF activity was detected by using the 12H5 cells. Numbers represent the percent rosette inhibition by the affluent/eluate fractions from lentil lectin Sepharose. The proportion of RFC in the absence of IgE-BF was 22.6 ± 0.7 (SD) %. (+)(−) indicate the presence or absence of GIF.

As shown in Table VIII, the GIF activity was detected in the passed-through fraction and in the eluate with 50 mM NaCl, but not in the other fractions.

Titration of a serial dilutions of the first two fractions indicated that the pass-through fraction had higher GIF activity than the 50 mM fraction.

Repeated experiments with a separate culture supernatant confirmed that the majority of GIF in culture supernatants could be recovered from a DEAE-Sepharose column, when culture supernatant of AC5 cells were concentrated 100-fold, diluted 3-fold with distilled water, and then passed-through the column. The passed-through fraction and washings with 10 mM Tris buffer containing 50 mM NaCl were combined, and concentrated to the original volume of the sample applied to DEAE-Sepharose. Titration of GIF activity in serial dilutions of the concentrated culture supernatant and the passed-through (50 mM NaCl) fraction showed that a 1:30 dilution of both samples could switch the 12H5 cells from the formation of glycosylated IgE-BF to the formation of unglycosylated IgE-BF. It was also found that 75 to 80% of protein in the culture supernatant could be removed by passing through the DEAE-Sepharose.

In order to estimate the molecular mass of GIF, 0.5 ml of the concentrated passed-through fraction from the DEAE-Sepharose was applied to a Superose-12 column and proteins were eluted at a flow rate of 1 ml/min. In this experiment, 5 ml fractions were collected, and each fraction was assessed for GIF activity by using the 12H5 cells. GIF activity was detected in fraction 9, which was recovered between 70 and 75 min. Since Fractions 6 and 8 may also have a weak activity, GIF activity in the serial dilutions of fractions 6, 8, 9 was assessed. The GIF was detected in a 1:10 dilution of fraction 9, but not in a 1:2 dilution of the other fractions. The results suggested that the molecular mass of the major species of human GIF is in the range of 11 KDa to 18 KDa. For better estimation of the size of GIF molecules, gel filtration on a Superose-12 was repeated in the same design, except that 1 ml fraction or 2.5 ml fractions were collected. Three separate experiments indicated that the majority of GIF was recovered between 68 and 72 min. It appears that the molecular mass of GIF is 12–18 KDa, as estimated by gel filtration.

Studies were also done identifying GIF by SDS PAGE. Two liter culture supernatant of the hybridoma in ABC medium were concentrated 100-fold, and fractionated on a DEAE-Sepharose column. Based on the experiments described above, the concentrated supernatant was diluted 3-fold with deionized water and passed through the DEAE-Sepharose. The passed-through fraction was concentrated, pre-absorbed with human IgG-coupled Sepharose, and GIF in the fraction was purified by affinity chromatography on the 388F1-coupled Affigel. In some experiments, the acid eluate fraction from the immunosorbent was adjusted to pH 8.0, and affinity-purification with 388F1-Affigel was repeated. Analysis of the affinity purified GIF preparation by SDS PAGE was performed under reduced and non-reduced conditions. The major band in the affinity-purified material has the molecular mass of 14 KDa under reduced conditions and 15 KDa under non-reduced conditions. In addition, a 67 KDa band was frequently observed. A portion of the affinity-purified preparation was dialyzed against DPBS and the GIF activity in the preparation was titrated. Assuming 100% recovery of GIF during dialysis and lyophilization, the sample applied to SDS-PAGE should have a GIF titer of 1:250.

Experiments were carried out to determine the relationship between the 14 KDa protein and GIF. The GIF in 2 liter culture supernatant of AC5 clone was purified by DEAE-Sepharose chromatography followed by affinity-purification using 388F1-Affigel. Acid eluates from the immunosorbent was adjusted to pH 8.0, concentrated to 1 ml by ultrafiltration and fractionated on a Superose 12 column. Every 2.5 ml eluate fractions were assessed for activity by using the 12H5 cells. In this experiment, the majority of GIF activity was detected in the fraction eluated between 67.5 and 70 minutes. The presence of GIF in the fraction was confirmed by ELISA using biotin-coupled mAb 141-B9. Although the ELISA signal was weak, only the GIF-containing fraction gave ELISA signal. One ml of the GIF-containing fraction was lyophilized and analyzed by SDS PAGE. The results confirmed that the 14 KDa peptide is present in the GIF-containing fraction.

EXAMPLE 6
PURIFICATION OF MURINE GIF AND AMINO ACID SEQUENCING

Murine GIF was purified from culture supernatant of GIF-producing murine T cell hybridoma $231F_1$ cells using anti-lipomodulin monoclonal antibody 141B9 (Iwata, et al., J.Immunol., 132: 1286, 1984). The monoclonal antibody 141B9 was purified from ascitic fluid of BALB/c mice injected with the hybridoma 141B9 by using a FAST-γ column. Approximately 10 mg of $IgG_1$ in the preparation were coupled to 1 ml of Affigel 10 beads. In order to obtain GIF, the $231F_1$ cells were cultured in high glucose Dulbecco's modified Eagle's medium, supplemented with 10% Nu-serum (Collaborative Research). After the number of $231F_1$ cells in the culture reached $1-2 \times 10^6$/ml, the cells were recovered, resuspended in serum-free DMEM at the concentration of $1.5 \times 10^6$ cells/ml, and cultured for 48 hr. Culture supernatants of the cells were concentrated 1000 fold by ultra filtration, and 10 ml of the concentrated culture supernatant were mixed with 2 ml of 141B9-coupled Affigel for 6–12 hr at 4° C. The immunosorbent was washed extensively with 10 mM phosphate buffer containing 50 mM NaCl, followed by the same buffer containing 500 mM NaCl. Proteins retained in the immunosorbent were then eluted with 0.1M sodium acetate buffer, pH 3.0. Affinity-purified GIF was mixed with a 1/10th volume of 100% (wt/vol) trichloracetic acid. The mixture was kept at −20° C. for 15 min, and centrifuged at 15,000×g for 5 min to recover the precipitates. Proteins in the precipitates were electrophoresed in 15% polyacrylamide/SDS gel under reducing conditions, and electroblotted to polyvinylidene difuroride (PVDF) membrane in 10 mM CAPS buffer, pH 11.0. After visualizing protein bands by staining with Coomassie Brilliant Blue (CBB), a 14 kDa band was excised for determination of amino acid sequence.

The PVDF-immobilized protein was reduced and S-carboxymethylated in situ, and then digested with 1 pmol Achromobacter protease I (Wako Pure Chemicals) in 90 mM Tris buffer (pH 9.0) containing 8% acetonitrile for 20 hours at 30° C. Digested peptides were separated by reverse-phase HPLC using a 5 μC8-300A column (Waters) equilibrated with 0.05% trifluoroacetic acid in water as mobile phase. Peptides were eluted by a linear gradient (2 to 50%) of 0.02% trifluoroacetic acid in 2-propanol/acetonitrile (7:3). Major peptide peaks showing absorbance at 214 nm were collected and amino acid sequence analysis of the peptides was performed using a gas-phase sequencer (Applied Biosystems Model 470A) with modified program for micro sequencing (Iwamatsu, et al., *J. Biochem.*, 110: 51–158, 1991). The amino acid sequences of the isolated peptides are shown below.

| PEPTIDES | SEQUENCE |
| --- | --- |
| AP-1 | (K)-I-G-G-A-Q-N-R-N-Y-S-K |
| AP-23 | (K)-L-L-C-G-L-L-S-D-R-L-H-I-S-P-D-R-V-Y-I-N |

PVDF-retained peptide fragments after Achromobacter protease I digestion were sub-digested with 2 pmol of endoproteinase Asp-N (Boehringer Mannheim) in 100 mM ammonium bicarbonate (pH 7.8) containing 8% acetonitrile for 16 hours at 30° C. After the digestion, four major peptides were collected by HPLC and sequenced as described above. The amino acid sequence of each peptide is as follows.

| PEPTIDES | SEQUENCE |
| --- | --- |
| AN-4 | D-M-N-A-A-N-V-G-X-N-G-S-T-F-A |
| AN-5 | D-P-C-A-L-C-S-L-H-S-I-G-K |
| AN-7 | D-R-L-H-I-S-P-D-R-V-Y-I-N-Y-Y |

X in AN-4 was not detected.

Peptides retained on the membrane after endoproteinase Asp-N digestion were further sub-digested with 1 pmol trypsin-TPCK (Worthington Biochemical) in 100 mM ammonium bicarbonate (pH 7.8) containing 8% acetonitrile for 20 hr at 30° C. One major peptide (T-1) was collected and sequenced.

| PEPTIDES | SEQUENCE |
| --- | --- |
| T-1 | P-M-F-I-V-N-T-N-V-P-R |

The N-terminal amino acid sequence was directly sequenced by injecting a small piece of PVDF-immobilized protein sequencer (Shimazu PSQ-1).

| N-terminal | (M)-P-M-F-I-V-N-T-N-V-P-R-A-S-V |
| --- | --- |

Approximately 85% of the analyzed peptides showed a deletion of N-terminal methionine residue.

EXAMPLE 7
cDNA CLONING AND SEQUENCING OF MURINE GIF

Based on the N-terminal amino acid sequence and the sequence of another peptide (AN-5) described above, oligo- nucleotides were synthesized. Attempts were made to amplify a partial cDNA by polymerase chain reaction, and to use the cDNA obtained to probe a murine cDNA library. The synthesized primers used in the PCR were:

5'-ATGCCGATGTTCATCGTAAACACCAACGTGCCCCGC-3'

5'-GCCGATGCTGTGCAGGCTGCAGAGCGCGCACGGCTC-3'

Cytoplasmic RNA was isolated from GIF-producing murine T hybridoma 231F$_1$. After purification of mRNA by using oligo(dT)-cellulose, single strand cDNA was synthesized on the mRNA template by reverse transcription primed by dT$_{15}$ on 231F$_1$. RNA template. PCR was carried out in standard conditions. Briefly, the template DNA was denatured at 94° C. for 1 min, annealed with the primers described above at 59° C. for 1 min, followed by an extension at 72° C. for 45 sec. A 0.2 Kb fragment amplified in the PCR was ligated to pCR 1000 vector (Invitrogen, La Jolla, Calif.) for subsequent cloning and DNA sequencing. After confirming the nucleotide sequence of the fragment, the insert was cut out with EcoRI digestion to screen the cDNA library of murine T cell hybridoma, 231F$_1$ cells, which was constructed by using Uni-ZAP cDNA synthesis kit (Stratagene, La Jolla, Calif.). EcoRI recognition site was attached to double stranded cDNA, which was then digested with XhoI, and cDNA was ligated into Uni-ZAP XR vector. The cDNA library was screened by hybridization with the 0.2 Kb DNA described above. Seven clones were isolated after screening a half million independent clones. Restriction mapping of all of the 7 clones showed a single pattern.

The longest clone (0.65 Kb) was chosen for DNA sequencing by a standard dideoxy method. The nucleotide sequence and deduced amino acid sequence of murine GIF is shown in FIG. 1. Underlines indicate location of the identified peptides in the Edman degradation of purified murine GIF. Estimated size of GIF protein is 13 kDa, which correlates with that of purified GIF from the T hybridoma 231F$_1$ cells. The nucleotide sequence flanking the first methionine codon favors the translation initiation rule. The length of this insert was 0.65 Kb. Northern blot analysis of murine T cell and tissue RNA showed the presence of a single species of mRNA at 0.65–0.70 Kb, suggesting that the obtained cDNA was full length. It was also found that the murine GIF protein lacks a signal peptide, since no methionine residues were found in the 5' upstream of nucleotide 82 (FIG. 1).

EXAMPLE 8
ISOLATION OF cDNA ENCODING HUMAN GIF

Human T cell hybridoma AC5 was stained with anti-CD3 antibody and a GIF-producing CD3+ subclone was employed as a source of mRNA. Fractionation of RNA on oligo (dT)-cellulose was repeated to isolate mRNA, which was then employed as a template to synthesize cDNA using a ZAP-cDNA synthesis kit. After an EcoRI recognition site was attached, double stranded cDNA was digested with XhoI and size selected by filtration through Sephacryl S-400 spin columns. The cDNA was then ligated into the Uni-ZAP XR vector to construct a recombinant phage library. In the library, the proportion of phage containing an insert was 88 to 96% of total phage. The cDNA library was screened by hybridization with a fragment of cDNA encoding murine GIF. *E. coli* XL1 were cultured with phagemid containing murine GIF-cDNA and DNA in the bacteria was extracted. Plasmid was purified by centrifugation and digested with BamHI and XhoI. After electrophoresis on agarose, a 500 bp band was extracted, and purified by using Gene clean II kit (BIO 101). This cDNA was labeled with α-$^{32}$P-ATP using Prime-It gold kit from Stratagene.

E. coli PLK-F were cultured with the library which contained 5×10$^4$ pfu, and phage were transferred to nylon membranes (Duralose, Stratagene) which had been coated with E. coli. The membranes were placed on an LB bottom plate and kept at 37° C. overnight. After treatment with 0.5M NaOH, neutralization with Tris and washing with 2×SSC, the membranes were dried at 80° C. to fix DNA on the membranes.

For screening of the cDNA library, the membranes were pretreated with sonicated salmon sperm DNA, and then incubated overnight at 60° C. with $^{32}$P-labeled mouse GIF cDNA, which had been heated for 5 min at 100° C. The membranes were washed twice each with 6×SSC containing 0.1% SDS and 0.1×SSC plus 0.1% SDS and exposed to radioautographic film. Phage was extracted from positive clones and screening was repeated twice more to isolate positive clones. Among 200,000 phage which were screened, 27 positive clones were isolated. In order to confirm that the positive phage clones actually contained cDNA homologous to mouse GIF cDNA, phagemid DNAs were obtained form each positive phage clone, electrophoresed in 1% agarose gel, blotted in Zeta-probe membrane and then hybridized with $^{32}$P-labeled mouse GIF cDNA.

In order to determine the nucleotide sequence of human GIF cDNA, phagemid from each phage clone was digested with EcoRI and XhoI, and electrophoresed to obtain the insert. Among 27 clones, several clones having a 0.5 Kb insert were sequenced in the dideoxy-method. The insert was digested with SacI, PstI and SmaI and fragments were subcloned in pUC19 or pBluescript SK-vectors. Plasmid DNA was purified by the alkaline-SDS method and clones were sequenced using sequence Ver 2 (USB). The entire nucleotide sequence of full length cDNA (PNY 106) is shown in FIG. 2. The sequence was homologous to the sequence of a purported human MIF cDNA (Weiser, et al., Proc.Natl.Acad.Sci.U.S.A. 86: 7522–7526, 1989), except that the codon from nucleotides 390 to 392 is AAT (asparagine) in GIF cDNA, whereas the MIF cDNA has a codon of AGT (serine). Another difference was that 5' end noncoding region in pYN 106 was 40 base longer than that of MIF.

An RNase protection assay was performed in several T hybridoma cells to determine whether there was any redundancy in the structure of mRNA detected by GIF cDNA. The results confirmed that there is only a single species of mRNA corresponding to GIF.

EXAMPLE 9

EXPRESSION OF RECOMBINANT GIF IN E. COLI

A. Construction of bacterial expression systems

This example relates to expression of human and mouse GIF polypeptides in E. coli. The human GIF cDNA inserted into BlueScript at EcoRI and XhoI sties was annealed with the oligonucleotide primers:

5'-AACCTTAAGAAAAACCAAGGAGGTAATAAATAATG
CCGATGTTCATCGTAAACACCAACG-3'

3'-CACCCGACCTTGTTGAGGTGGAAGCGGATTATCCCT
AGGCAA-5'

These primers were synthesized by the phosphoramidite method (McBride, et al., Tetrahedron Lett., 24: 245–248, 1983). The 5'-end primer contained Shine-Dalgano sequence for preferred bacterial expression (Scherer, et al., Nucl. Acids. Res., 8: 3895–3950, 1980), and each primer contained AflIII and BamHI sites, respectively.

The human GIF cDNA was amplified using the polymerase chain reaction (PCR) (Mullis, et al., Method in Enzymol, 155: 335–350, 1987). Unless otherwise noted, the denaturation step in each PCR cycle was set at 94° C. for 1 min, and elongation was at 72° C. for 2 min. The temperature and duration of annealing was variable from reaction to reaction often representing a compromise based on the estimated requirement of several different PCRs being carried out simultaneously.

Figure 4:
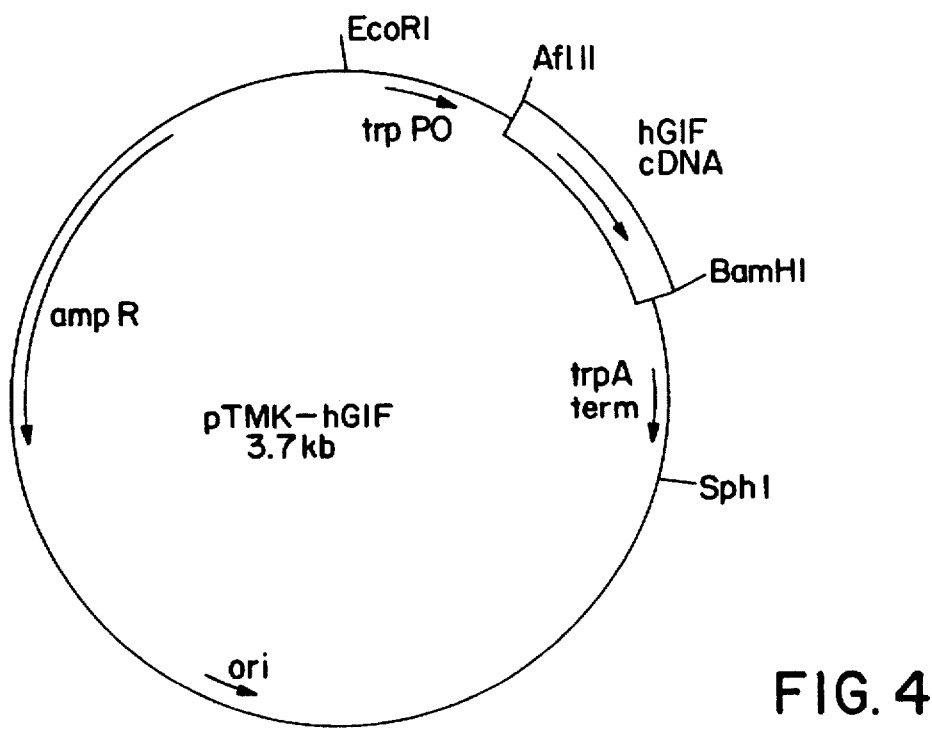
FIG. 4 shows a map of the pTMK-hGIF vector.

Amplified cDNA fragment, isolated from agarose gel, was digested with AflIII and BamHI, and ligation inserted into a pST811 vector carrying a Trp promoter and a TrpA terminator (FIG. 3, Japanese patent, Kokaikoho 63-269983) at the unique AflIII and BamHI sites. This new plasmid, called pTMK-hGIF (FIG. 4) was transformed into competent RR1 E. Coli host cells. Selection of plasmid-containing cells was on the basis of the ampicillin resistance (marker gene carried on the pST811 vector). The DNA sequence of the synthetic oligonucleotides and the entire human GIF gene was confirmed by DNA sequencing of plasmid DNA.

The bacterial expression system of mouse GIF was constructed from the mouse GIF cDNA inserted into BlueScript by the same procedures as human GIF. The primers to generate AflIII and BamHI sites at both ends of mouse GIF cDNA using PCR were:

5'-AACCTTAAGAAAAACCAAGGAGGTAATAAATAATG
CCTATGTTCATCGTGAACACCAATG-3'

3'-GCACCCGACCTTGCCAAGGTGGAAGCGAACTATCCC
TAGGCAA-5'

The plasmid containing mouse GIF cDNA in pST811 vector was designated pTMK-mGIF.

Alternatively, the human or the mouse GIF coding sequence could be recovered from pTMK-hGIF or pTMK-mGIF by excision with AflIII and BamHI, and inserted into any desired bacterial vector, having a PL, lac, tac or OmpF promoter using procedures described in Molecular Cloning: A Laboratory Manual, Maniatis, et al., 1982. These exemplary bacterial vectors, as well as others known in the art, could be transformed into bacterial host cells and GIF expressed.

B. Culture of E. coli Producing GIF

RR1 E. coli carrying plasmid pTMK-hGIF or pTMK-mGIF were cultured in 20 ml Luria broth containing 50 μg/ml of ampicillin, and grown overnight at 37° C. The inoculum culture was aseptically transferred to 1 liter of M9 broth which was composed of 0.8% glucose, 0.4% casamino acid, 10 mg/liter thiamine and 50 mg/liter ampicillin, and cultured for 3 hrs at 37° C. At the end of this initial incubation, 40 mg of indoleacrylic acid was added and the culture incubated for an additional 5 hours at 37° C.

EXAMPLE 10

PURIFICATION OF RECOMBINANT GIF PRODUCTS EXPRESSED IN E. Coli

About 5 g wet weight of harvested cells were suspended in water to a volume of 30 ml and broken by French-Press (8000 psi repeated 4 times). Supernatants and broken cell pellets were separated by centrifugation at 15000×g for 10 min at 4° C. The cell pellet was washed twice with water. By the use of SDS-polyacrylamide gel electrophoresis, it was evident that most of the pellet was human GIF protein. The supernatant also contained soluble human GIF protein. The ratio of soluble to insoluble GIF was about 1:3.

A. Purification of Soluble GIF

Soluble GIF fraction was frozen overnight at −80° C. and slowly thawed at room temperature. Insoluble material was removed by centrifugation at 15000×g for 15 min. In this step, most of the bacterial contaminants could be removed. The supernatant was adjusted to pH 6.0 by adding 50 mM sodium acetate buffer (pH 5.0) and applied to a CM-Sepharose Fast Flow (Pharmacia) column (5×18 cm) equilibrated with 20 mM sodium acetate buffer (pH 6.0) at 4° C. The column was washed with 20 mM sodium acetate buffer (pH 6.0) at a flow rate of 2 ml/min and proteins eluted by an NaCl step gradient. GIF was eluted with 0.5 NaCl in the 20 mM sodium acetate buffer (pH 6.0). The purity of human GIF was estimated by SDS-polyacrylamide gel electrophoresis and determined to be more than 95% pure.

B. Purification and refolding of insoluble GIF

The pellet fraction containing insoluble human GIF was suspended in 10 ml of 0.2M Tris-HCl buffer (pH 8.0) containing 6M guanidine HCl and 25 mM EDTA and incubated at room temperature for 3 hrs by gentle mixing to solubilize human GIF. Remaining insoluble material was removed by centrifugation for 15 min at 15000 g.

The soluble GIF fraction was applied to a Sephacryl S-200 Super Fine (Pharmacia) column (5×100 cm) equilibrated with 6M guanidine-HCl, 25 mM EDTA and 0.2M Tris buffer (pH 8.0) and eluted at a flow rate of 2 ml/min at room temperature. After the void volume had eluted, 10 ml fractions were collected and analyzed for GIF by SDS-polyacrylamide gel electrophoresis by Western blot staining. About 120 ml of GIF positive fractions were concentrated to 5 ml using a YM5 Millipore ultrafiltration membrane.

For refolding of the solubilized GIF, the sample was added slowly to 2 liters of 20 mM Tris buffer (pH 8.0) with gentle stirring at room temperature. After 24 hours, the mixture was concentrated 10 fold using a YM5 membrane.

For removal of remaining E. coli contaminants, a sample was applied to a TSK DEAE-5PWD (Toyo Soda) column (7.5×75 mm) equilibrated with 20 mM Tris buffer (pH 8.0). After sample application, the column was washed with the same buffer and GIF eluted with a gradient of 0 to 0.1M NaCl in column buffer at flow rate of 0.5 ml/min at room temperature. GIF-containing fractions, as determined by Western blot, were concentrated using a YM5 membrane. The purity of human GIF was estimated by SDS-polyacrylamide gel electrophoresis and was determined to be more than 95% pure. Recombinant mouse GIF was purified using the same procedures described above.

EXAMPLE 11

AMINO ACID SEQUENCING AND ANALYSIS OF RECOMBINANT GIF

A. Amino Acid Sequencing of Recombinant Human GIF

The purified recombinant human GIF obtained from a DEAE column was subjected to SDS-polyacrylamide gel electrophoresis and blotted onto a PVDF membrane. The membrane was stained with Ponceau S and the GIF band was excised from the membrane. The N-terminal amino acid sequence was determined by using a Shimazu PSQ-1 protein sequencer. About 60% of recombinant human GIF had the following 10 amino acids at the N-terminus:

$^1$Met-$^2$Pro-$^3$Met-$^4$Phe-$^5$Ile-$^6$Val-$^7$Asn-$^8$Thr-$^9$Asn-$^{10}$Val SEQ ID NO:7

This sequence was identical to the sequence deduced from the cDNA sequence of human GIF. About 40% of GIF lacked an N-terminal $^1$Met residue.

B. Amino Acid Analysis of Recombinant Murine GIF

The purified recombinant mouse GIF obtained from a DEAE column was hydrolyzed in twice-distilled 5.7M HCl containing 0.2% phenol for 24 hours at 110° C. in an evacuated tube. This hydrolyzed sample was suspended in 0.02M HCl and the amino acid composition determined (HITACHI 835S amino acid analyzer). In analyzing these results (Table IX), it was generally recognized that lower numbers of Cys, Thr, Met and Trp residues were obtained than was deduced from cDNA sequence due to degradation which occurs during acid hydrolysis. The lower value for His residues could be due to insufficient separation from $NH_3$. Inclusion of a known amount of an internal standard such as Leu in the amino acid composition analyses allowed quantitation of protein in the sample. Extinction coefficients of recombinant mouse GIF at 280 nm was 1.89.

TABLE IX

QUANTITATIVE AMINO ACID COMPOSITION OF E. Coli DERIVED mGIF

| MOLECULE<br>AMINO ACID | AMINO ACID COMPOSITION MOLES PER MOLE OF PROTEIN | | | PREDICTED RESIDUES PER MOLECULE |
|---|---|---|---|---|
| | RUN1 | RUN2 | RUN3 | |
| ASP + ASN | 10.19 | 10.12 | 10.31 | 14 |
| GLU + GLN | 6.98 | 6.97 | 7.93 | 8 |
| CYS | 0.96 | 0.59 | 1.08 | 3 |
| SER | 9.11 | 9.03 | 9.12 | 9 |
| GLY | 8.98 | 8.97 | 8.78 | 9 |
| HIS | 0.000 | 1.70 | 1.86 | 3 |
| ARG | 5.07 | 4.81 | 4.84 | 4 |
| THR | 3.85 | 3.78 | 3.82 | 6 |
| ALA | 10.37 | 10.43 | 10.30 | 10 |
| PRO | 8.42 | 8.17 | 8.19 | 7 |
| TYR | 4.63 | 4.60 | 4.55 | 5 |
| VAL | 7.47 | 7.49 | 7.57 | 8 |
| MET | 3.13 | 3.03 | 3.05 | 4 |
| ILE | 6.14 | 6.09 | 6.10 | 6 |
| LEU | 11.00 | 11.00 | 11.00 | 11 |
| PHE | 4.28 | 4.02 | 4.35 | 4 |
| TRP | 0.00 | 0.00 | 0.00 | 1 |
| LYS | 2.92 | 2.95 | 2.87 | 3 |

EXAMPLE 12

PRODUCTION OF POLYCLONAL ANTIBODY AGAINST GIF

Three rabbits were injected subcutaneously with 100 µg of the same GIF sample in Freund's incomplete adjuvant every 2 to 3 weeks. After 114 days, the rabbit serum was collected and the IgG purified by protein A affinity column chromatography (Prosep-A. BioProcessing). About 150 mg of IgG was obtained from 25 ml of serum. This antibody recognized mouse GIF and human GIF, and could be used for Western blotting and purification of GIF.

EXAMPLE 13

EXPRESSION OF RECOMBINANT GIF IN MAMMALIAN CELLS

A. Construction of Mammalian Cell Expression Systems for Direct Expression

This example relates to expression of human GIF polypeptide in mammalian cells. The human GIF cDNA inserted into BlueScript at EcoRI and XhoI sites was annealed with the oligonucleotides primers:

5'-CCCAGATCTAAGCGGATGCCGATGTTCATCGTAAACACC-3'

3'-CCTTGTTGAGGTGGAAGCGGATTCCATGGCAA-5'

Figure 5:
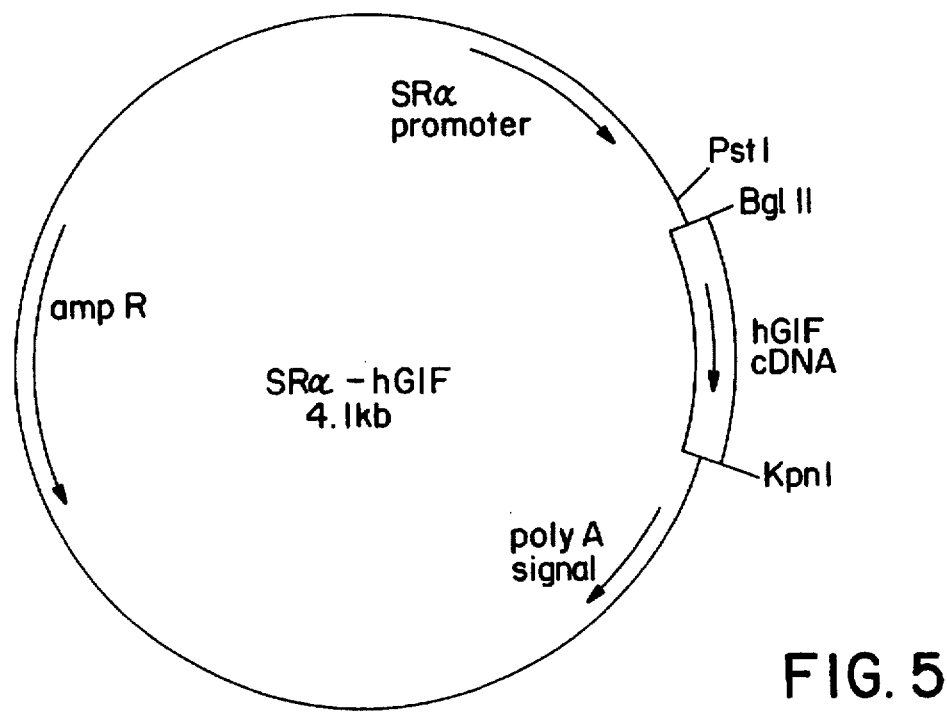
FIG. 5 shows a map of the SRα-hGIF vector.

Each primer contained a BglII or KpnI site. The human GIF cDNA was amplified using PCR, isolated from agarose gel, and digested with BglII and KpnI. This fragment was inserted by ligation into a modified SRα vector (Takabe, et al., *Mol. Cell. Biol.*, 8: 466–472, 1988) having a BglII site following a PstI site. The plasmid, called SRα-hGIF (FIG. 5) was transformed into competent DH5 *E. coli* cells. Plasmid-containing cells were selected on the basis of an Amp$^r$ gene carried on the SRα vector. Plasmid DNA was isolated from cultured cells and the nucleotide sequence of the entire human GIF gene was confirmed by DNA sequencing.

B. Construction of Mammalian Expression Systems Having an Additional Signal Sequence Since GIF did not appear to have a signal sequence based on analysis of the DNA structure, another expression system was constructed to introduce a signal sequence to GIF, so that the GIF polypeptide would be secreted from the transfected cells through a constitutive secretory pathway. Many secretory proteins, including polypeptide hormones, growth factors and plasma proteins are synthesized as precursors and undergo post-translation proteolytic processing which is frequently required for their secretion and expression of biological activity. For example, human calcitonin is synthesized by endocrine C cells of the thyroid as the large precursor molecule procalicitonon (Craig, et al., *Nature*, 295: 345–347, 1982). Procalcitonin, which consists of N-terminal pro-region, calcitonin, and a C-terminal pro-region, undergoes proteolytic processing at the flanking dibasic sites to generate the calcitonin peptide (Burns, et al., *Mol. Endocrinol.*, 3: 140–147, 1989). Therefore, it was speculated that procalcitonin is cleaved by protein convertases of neuroendocrine origin (Smeekens, et al., *J. Biol. Chem.* 265: 2997–3000, 1990; *Proc. Natl. Acad. of Sci.*, 88: 340–344, 1991). In addition, the N-terminal pro-region of human procalcitonin has an additional Arg residue at the −4 position and has the sequence of Arg-Ser-Lys-Arg (amino acid residues 5-8 of SEQ ID NO:26) at the carboxy terminus which is a cleavage motif that can be recognized by the processing enzyme, furin (Fuller, et al., *Science*, 246: 482–486, 1989).

In the present example, human GIF cDNA was fused in-frame with the 3' end of the gene encoding the N-terminal pro-region of human calcitonin precursor, and inserted into the SRα vector. Human furin cDNA was also cloned and inserted into the SRα vector. Both vectors were co-transfected to COS-1 cells (ATCC CRL 1650) which resulted in secretion of mature human GIF.

1. Cloning of cDNAs

The cDNA fragment encoding the signal peptide and N-terminal pro-region of human pro-calcitonin (pro-CT) (Steerbergh, et al., *FASEB Letter* 207: 94, 1986) was amplified by PCR using human calcitonin cDNA as template. mRNA was isolated from human thyroid carcinoma TT cells (ATCC CRL 1803), and reverse transcribed into cDNA which was used as a template for PCR.

Oligonucleotide primers having a PstI site, as shown below, were synthesized and the human calcitonin precursor gene was amplified.

5' AACTGCAGATGGGCTTCCAAAAGTTC-3'

-continued

3'-GACCTGTCGGGGTCTAGATTCGCCGACGTCCA-5'

The amplified gene was cloned into PstI digested SRα vector. Human GIF cDNA inserted into BlueScript was annealed with the oligonucleotide primers shown below.

5'-CCAGATCTAAGCGGATGCCGATGTTCATCGTAAACACC-3'

3'-CCTTGTTGAGGTGGAAGCGGATTCCATGGCAA-5'

Figure 6:
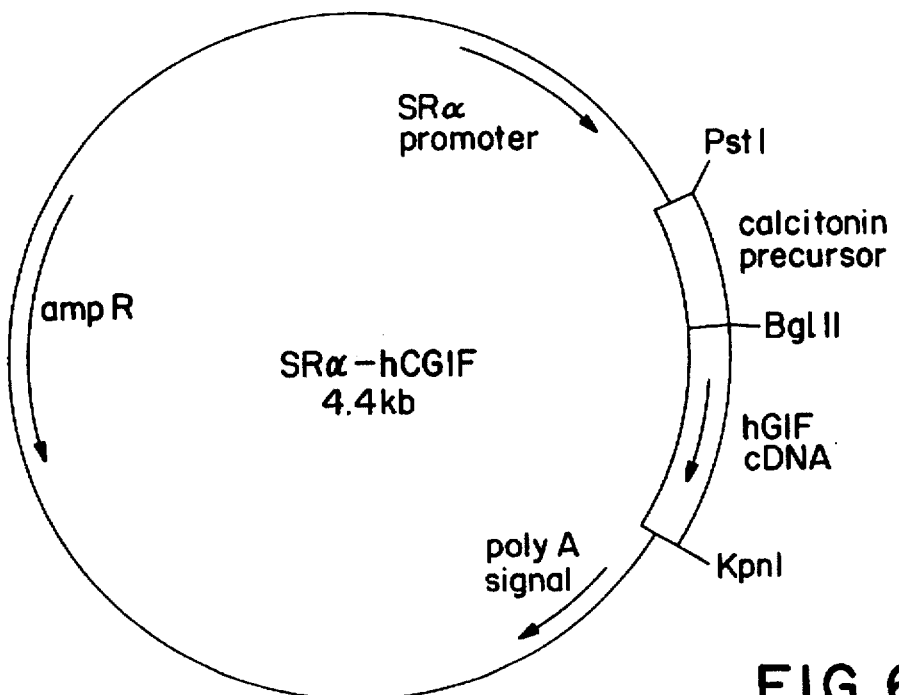
FIG. 6 shows a map of the SRα-hcGIF vector.

The primers had a BglII site and KpnI site, respectively. The amplified gene codes for Arg-Ser-Lys-Arg sequence followed by the hGIF sequence. This gene was then inserted by ligation into BglII and KpnI digested SRα which had human calcitonin precursor gene as previously described. This new plasmid, designated SRα-hcGIF (FIG. 6) was transformed into DH5 *E. coli* cells. Plasmid DNA was isolated from cultured cells and the DNA sequence of entire human calcitonin precursor and the human GIF genes were confirmed by DNA sequencing.

Human furin cDNA was cloned by the same PCR amplification method. Poly(A)$^+$ mRNA was isolated from the human bladder carcinoma cell line HT1376 (ATCC, CRL 1472), reverse-transcribed into cDNA, and used as a PCR template. Six oligonucleotide primers (F1–F6, shown below) were prepared based on the published furin cDNA sequence (Fuller, et al., *Science*, 246: 482, 1989) using an ABI 394 DNA synthesizer (Applied Biosystems, Inc. Calif.). Three cDNA fragments, covering coding sequences 1–951, 922–1604, and 1565–2385 bp of human furin DNA, respectively, were purified from the corresponding PCR products. The cDNA fragment encoding the amino terminal protein sequence was annealed with the adjoining cDNA fragment by using of a 27 bp overlap between the two fragments. The resulting cDNA mixture was re-amplified using primers corresponding to the 5' end of the first fragment and the 3' end of the second fragment. The resulting 1.6 kb cDNA was ligated via the Bsp HI site with the third cDNA fragment encoding the remaining carboxyl terminal furin. The whole cDNA construct was subcloned into the TA cloning vector pCR1000 (Invitrogen, La Jolla, Calif.). Human furin cDNA sequences were determined using the Sequenase kit (United States Biochemical Corp., OH). Restriction site mapping and partial sequence analysis revealed that the cloned cDNA was identical to previously reported human furin. An Eco RI-Not I fragment containing the full-length human furin was cloned into the mammalian expression vector pEFneo, which was generated by inserting a neo-expression unit into a modified PEF-BOS (Mizushima, et al., *Nucl. Acids Res.*, 18: 5322, 1990).

The six synthesized oligonucleotide primers used for cloning human furin cDNA by PCR were:

F1  5'-AAGAATTCCCCCATGGAGCTGAGGCCCTGGTTG-3'

F2  3'-GTGGTTGTCATAGATGTGCGACAGGTAG-5'

F3  5'-ACACCAACAGTATCTACACGCTGTCCAT-3'

F4  3'-TACCCAAATTACTGACCCGGAAGTACTG-5'

F5  5'-ACTACTCCGCAGATGGGTTTA-3'

F6  3'-TTTCTGGTCTCGCGGGAGACTCTTAAGAA-5'

F1 and F2, were used to amplify the furin coding sequence of 1–951 and F3 and F4 were used to amplify 922–1604. Both PCR products were annealed by using a 27 bp overlap and the resulting cDNA mixture was re-amplified by using primers of F1 and F4. The derived cDNA of 1.6 Kb was ligated via the BspHI site with a F5 and F6 amplified cDNA fragment which encoded fragment 1565–2385 bp of the human furin gene. The entire furin cDNA was inserted into EcoRI digested SRα vector. This new plasmid, designated SRα-hfurin, was transformed into DH5 E. coli cells. Plasmid DNA was isolated from cultured cells and the DNA sequence of the synthetic oligonucleotides and entire human furin gene was confirmed by DNA sequencing.

C. Expression of GIF in COS-1 Cells

The plasmids SRα-hGIF or SRα-hcGIF plus SRα-hfurin were transfected into COS-1 cells. Plasmid DNA was added to DMEM/F12 (1:1) medium containing 10% Hanks' BSS, 2% FCS, 40 μg/ml DEAE dextran, 100 μM chloroquine at the concentration of 1 μg/ml. This mixture was overlaid onto COS-1 cells in culture dishes and incubated (5 hours, 37° C., 5% $CO_2$). After incubation, cells were washed and cultured overnight (37° C. in DMEM/F12 (1:1) medium with 10% FCS). After washing again, cells were cultured in serum free DMEM/F12 medium containing 20 μg/ml bovine insulin (Sigma), 20 μg/ml human transferrin (Sigma), 40 mM monoethanolamine, 0.1 μM sodium selenite, and 1 mg/ml BSA for 1 week at 37° C. As a control, the vector without insert was transfected to COS-1 cells.

The amount of GIF in the culture supernatants was estimated by Western blotting using anti-mouse GIF polyclonal antibodies. The supernatants derived from SRα-hcGIF transfected COS-1 cells was shown to contain a mature form of GIF. Furin expressed together with calcitonin-GIF cleaved the calcitonin precursor sequence allowing the secretion of GIF. The amount of GIF secreted from the COS-1 cells was comparable to the amount of calcitonin precursor-GIF secreted.

One skilled in the art can also construct other mammalian expression vectors comparable to SRα-hGIF or SRα-hcGIF. The human GIF coding sequence could be recovered from SRα-hGIF or SRα-hcGIF by excision with BglII and KpnI, and inserted by ligation into many vectors such as pCD (Okayama, et al., Mol. Cell. Biol., 2: 161,170, 1982), pCDM8 (Seed, et al., Proc. Natl. Acad. Sci. USA USA, 84: 3365–3369, 1987) and pDSVE (U.S. Ser. Nos. 025,344 and 152,045). The transformation of these vectors into appropriate host cells, such as CHO, 3T3 and BHK cells, can result in expression of GIF. It would be routine to select a preferred vector system, a GIF cDNA with or without signal sequence, and an appropriate host cell, for increasing secretion of GIF.

D. Construction of a unique fusion expression vector for the secretion of recombinant truncated peptide without co-transfection with furin cDNA Furin is expressed in many tissues, and appears to be predominantly localized to the Golgi region (Bresnaham, P. A., et al., J.Cell.Biol. 111: 2851, 1990; Mitsui, Y., et al., J. Biol. Chem., 266: 16954, 1991), suggesting that furin or a furin-like enzyme is involved in the cleavage of proproteins for the secretion of a mature protein through a constitutive secretory pathway. The presence of a furin-like enzyme in COS cells was predicted by Smeekens, et al., (Proc.Natl.Acad.Sci., U.S.A., 89: 8822, 1992). Therefore, the furin-like enzyme in COS cells can be utilized for processing of a recombinant fusion protein for the secretion of a mature peptide, if a proper cleavage motif for the enzyme is used.

An Fc cDNA was utilized for test purposes to design an efficient proteolytic cleavage site. The Fc fragment of human IgG has no signal peptide and the cDNA fragment encoding the Fc fragment does not carry the translation initiation codon ATG, the protein cannot ordinarily be expressed by transfection of the cDNA into mammalian cells. Pro-CT was used for a carrier peptide for the Fc fragment, and amino acid sequences of the carboxyl terminal end of the pro-CT were modified to create an appropriate cleavage motif which can be recognized by the putative furin-like enzyme in COS-1 cells. Based on previous information on cleavage motifs for processing enzymes, four different amino acid sequences were introduced into pro-CT. The cDNA encoding pro-CT was amplified by PCR with the human calcitonin cDNA as the template, using one 5' end primer (CT1), and four different 3' end primers (CT2, CT3, CT4 and CT5) as listed in Table X. The primers CT2, CT3, CT4, and CT5 were modified by introducing several basic residues in different locations in order to study the effect of such changes on the processing efficiency by the putative endoprotease of COS-1 cells.

TABLE X

LIST OF OLIGONUCLEOTIDE PRIMER
FOR PCR AMPLIFICATION OF HUMAN PRO-CT

|  |  |  |  | Met | Gly | Phe | Gln | Lys | Phe |  |
|---|---|---|---|---|---|---|---|---|---|---|
| CT1(28 MER) | GAAT | TCT | GTC | ATG | GGC | TTC | CAA | AAG | TTC |  |
|  |  |  |  |  |  |  |  | ↓ |  |  |
| CT2 (30 MER) |  |  | −6 | −5 | −4 | −3 | −2 | −1 | +1 |  |
|  | Leu | Asp | Ser | Pro | Arg | Ser | Lys | Arg | Ser | Arg |
|  | CTG | GAC | AGC | CCC | AGA | TCC | AAG | AGA | TCT | AGA |
|  | GAC | CTG | TCG | GGG | TCA | AGG | TCT | TCT | AGA | TCT |
|  |  |  |  |  |  |  |  |  | ← |  |
| CT3 (30 MER) | Leu | Asp | Arg | Pro | Met | Ser | Lys | Arg | Ser | Arg |
|  | CTG | GAC | AGA | CCC | ATG | TCC | AAG | AGA | TCT | AGA |
|  | GAC | CTG | TCT | GGG | TAC | AGG | TTC | TCT | AGA | TCT |
|  |  |  |  |  |  |  |  |  | ← |  |
| CT4 (30 MER) | Leu | Asp | Arg | Pro | Arg | Ser | Lys | Arg | Ser | Arg |
|  | CTG | GAC | AGA | CCC | AGA | TCC | AAG | AGA | TCT | AGA |
|  | GAC | CTG | TCT | GGG | TCT | AGG | TTC | TCT | AGA | TCT |
|  |  |  |  |  |  |  |  |  | ← |  |

TABLE X-continued

LIST OF OLIGONUCLEOTIDE PRIMER
FOR PCR AMPLIFICATION OF HUMAN PRO-CT

| CT5 (30 MER) | Leu | Asp | Ser | Pro | Met | Ser | Lys | Arg | Ser | Arg |
|---|---|---|---|---|---|---|---|---|---|---|
| | CTG | GAC | AGC | CCC | ATG | TCC | AAG | AGA | TCT | AGA |
| | GAC | CTG | TCG | GGG | TAC | AGG | TTC | TCT | AGA | TCT |
| | | | | | | | | | ← | |

Arrow with dashed lines indicate the synthesized primer in the 5' and 3' direction. CT1 encodes the amino terminus of pro-CT and the four other primers encode the carboxyl terminus of pro-CT. Arrow with plain line indicates the cleavage site by endoprotease. The nucleotide sequence AGATCTAGA in CT2 - CT5 is recognized by BglII and XbaI.

Figure 7:
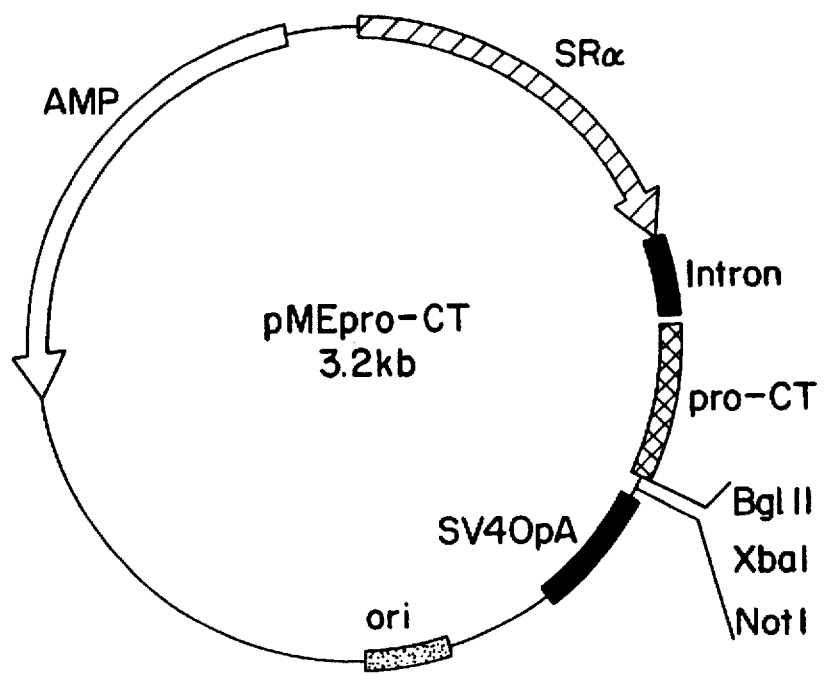
FIG. 7 shows a map of the fusion expression vector, pMEproCT.

In order to construct plasmids, an EcoRI restriction site was introduced into CT1, and Bgl II plus Xba I restriction sites were introduced into four other primers. After generating the four corresponding pro-CT cDNA fragments they were subcloned into the EcoRI and XbaI sites of the plasmid pBluescript II KS (+) (Stratagene). Since Not I became a neighbor restriction site after Xba I on this plasmid vector, the pro-CT cDNAs could be excised with EcoRI and Not I. Next, each of the four different pro-CT cDNAs with mutated 3'ends were inserted into the mammalian expression vector pME18S, which carries the chimeric retroviral promoter, SRα (Takabe, et al., *Mol. Cell. Biol.*, 8: 466, 1988). This new plasmid vector was designated pMEpro-CT (FIG. 7). This vector consists of i) a chimeric promoter SRα, fused by SV40 promoter plus the R region of long terminal repeat of the retrovirus, ii) pro-CT, and iii) SV40 early poly(A) addition signal. A multiple cloning site for Bgl II, Xba I, and Not I was included, following the carboxyl terminal proteolytic cleavage site of pro-CT, for insertion of a foreign gene of interest. The nucleotide sequences (AGATCTAGA) recognized by Bgl II and Xba I, encode Arg-Ser-Arg residues in the reading frame. Therefore, foreign cDNA can be introduced and fused with the pro-CT cDNA according to this frame.

The Fc cDNA of human IgG was obtained using PCR amplification method with two 28 nucleotide primers, G1 and G2, and with poly(A)+ mRNA from a human leukemia cell ine ARH-77 (ATCC, CRL1621) as the template. The 5' end primer G1 (5'-C TCTAGAGACAAAACTCACACATGC-3') and the 3' end primer G2 (5'-G GCGGCCGCCGCACTCATTTACCCGGAG-3') contain an Xba I site and a Not I site underlined respectively. The Fc cDNA thus obtained was subcloned into the Xba I and Not I sites of the plasmid pBluescript II KS (+). The cDNA fragment was sequenced using an ABI 270A sequencer (Applied Biosystems, Inc., CA). The Fc cDNA encoded a sequence beginning at the Asp residue which is located after the first of three Cys residues in the hinge region (Ellison, et al., *Nucl. Acids Res.*, 10: 4071, 1982). The cDNA was inserted in-frame after the pro-CT region into pMEpro-CT.

1. Secretion and cleavage of the chimeric proteins

To test whether the fusion protein comprising of the pro-CT region and the Fc fragment could be produced in a secreted form from the plasmid-transfected COS-1 cells, the chimeric plasmid containing cDNA encoding pro-CT with only dibasic Lys-Arg residues was used. Immunoblot analysis of the culture supernatant of the transfected cells with anti-human IgG showed that the fusion protein was detected predominately at a molecular weight of approximately 66 kDa under non-reducing conditions and 37 kDa under reducing conditions. Similar immunoblot analysis of the culture supernatant of the cell transfected with plasmid DNA of pMEpro-CT confirmed that the protein having reactivity with anti-IgG CT was not produced.

Based on the finding that the molecular size of the major protein in the non-reduced form was approximately twice that found for the reduced form, it was hypothesized that the fusion protein must be synthesized as a dimer protein. Since no Cys residue exists in the pro-CT region, the dimer could arise from the disulfide bonds formed between the Cys residues in the hinge region of the Fc fragment. Nevertheless, the molecular size of the protein (66 kDa as a dimer and 37 kDa as a monomer) indicated that the protein represents a fusion protein consisting of pro-CT and Fc fragment, but not the mature Fc fragment.

Processing efficiency was determined by transfecting the chimeric cDNAs with different cleavage motifs into COS-1 cells. Immunoblot analysis showed that the Fc fragment, released by proper proteolytic cleavage, was not detectable when the chimeric plasmid contained pro-CT cDNA encoding the dibasic Lys-Arg motif at the cleavage site. All of the secreted protein which reacted with anti-IgG CT antibodies was a fusion protein of 37 kDa under reducing conditions. Similar results were obtained when the fusion protein had an Arg residue at the P6 position, in addition to the Lys-Arg motif. When the fusion protein had an Arg residue at the P4 position, in addition to the Lys-Arg motif, the Fc fragment was detected in transfected COS-1 supernatant. However, the mature Fc fragment represented only a small fraction of secreted proteins reactive to anti-IgG. In contrast, the fusion protein with the Arg residues at both P4 and P6 positions at the carboxyl end of the pro-CT was processed most effectively to secrete a mature Fc fragment. When COS cells were transfected with the chimeric plasmid for the formation of the fusion protein with the cleavage motif of Arg-Pro-Arg-Ser-Lys-Arg, only a minute quantity of the fusion protein and a large quantity of the fusion protein and a large quantity of mature Fc fragment were detected in the supernatant. The results indicated that COS cells possess a processing enzyme which recognized the sequence of Arg-X-Arg-X-Lys-Arg.

2. Application of pMEpro-CT plasmid for the expression of bioactive recombinant GIF Since the experiment described above for the secretion of Fc fragment indicated that the cleavage motif of a putative furin-like enzyme in COS cells was Arg-X-Arg-X-Lys-Arg, this sequence was used for the formation of bioactive recombinant GIF. Pro-Ct cDNA was amplified by PCR using CT1 and CT4 primers (see Table X), and the amplified cDNA was inserted into the PME-pro-CT plasmid. The human GIF cDNA was introduced into the plasmid by methods described above for SRαhcGIF, and fused with the pro-CT cDNA. Transfection of the plasmid into COS cells resulted in the secretion of the 13 kDa GIF.

EXAMPLE 14

PURIFICATION OF RECOMBINANT GIF PRODUCTS EXPRESSED IN MAMMALIAN CELLS

For affinity purification, either the monoclonal anti-human GIF, 388F1 (Thomas, et al., *J. Immunol.*, 148: 729, 1992), or polyclonal rabbit antibodies against recombinant mouse GIF were coupled to Affigel 10 (Biorad) or HiTrap NHS-activated column (Pharmacia) following the procedures recommended by manufacturer. Monoclonal antibody (2–3 mgs) or γ globulin fraction of polyclonal antiserum (8–12 mgs) were coupled to 1 ml gel.

Fractionation of culture supernatants on the immunosorbent was carried out at 4° C. Culture supernatants of COS-1 cells were concentrated 10–20 fold by ultrafiltration and 10–15 volumes of the concentrated supernatant were passed through one volume of the immunosorbent column overnight. When the volume of the concentrated material was limited, 2 to 4 volumes of the supernatant were mixed overnight with one volume of the immunosorbent, and the suspension was packed into a column. The column was washed with 7–10 column volumes of PBS and proteins retained in the column were eluted with 3 to 4 column volumes of 0.1M glycine HCl buffer, pH 3.0. After the pH was adjusted to pH 7–8 with Tris buffer, the samples were analyzed by SDS-PAGE and GIF was detected by either silver staining or western blot with polyclonal anti-recombinant GIF. A portion of the wash fraction and acid eluated fraction were dialyzed against RPMI 1640 medium for bioassay. Purity of the 13 kDa protein in the acid eluate fraction was higher than 90%.

Alternatively, mammalian cell-derived GIF was purified using conventional column chromatography. In this example, 100 ml of COS-1 supernatant was concentrated ten fold and applied to TSK G2000SW (Toyo Soda) column (21.5×600 mm) equilibrated with PBS. The column was run at a flow rate of 3 ml/min at room temperature. GIF was eluted in estimated low molecular weight fractions, as determined by Western blotting using polyclonal anti GIF antibodies. GIF-containing fractions were pooled and concentrated by ultrafiltration and applied to a TSK DEAE-5PW (Toyo Soda) column equilibrated with 20 mM Tris HCl buffer, pH 8.0. The column was run at a flow rate of 0.5 mL/min at room temperature. After application, the column was washed with the same buffer, and GIF was recovered in this wash step. The differences in binding ability to DEAE between $E.$ $coli$ derived GIF and COS-1 derived GIF can be explained by the existence of O-linked glycosylation or phosphorylation.

Further purification of GIF was carried out using Vydac Protein C4 reverse phase column (The Separations Group) (4.6×150 mm). GIF fractions (10 ml) from the DEAE column was applied to C4 column, equilibrated with 100 mM ammonium acetate buffer, and GIF purified with a gradient of 0 to 90% ethanol in column buffer at a flow rate of 0.4 ml/min at room temperature. GIF was eluted in the fractions containing 50 to 60% ethanol, and was identified by SDS-polyacrylamide gel electrophoresis and Western blotting using polyclonal anti-GIF antibodies.

EXAMPLE 15

BIOLOGICAL ACTIVITIES OF RECOMBINANT GIF

A. Evaluation of GIF activity of recombinant GIF

The glycosylation inhibitory activity of recombinant human GIF was evaluated by the ability of test samples to switch murine T cell hybridoma 12H5 cells from producing glycosylated IgE-binding factors (IgE-BF) to producing unglycosylated IgE-BF (Iwata and Ishizaka, $J.Immunol.$, 141: 3270, 1988). In this assay, 12H5 cells were cultured for 24 hr with 10 μg/ml mouse IgE in the presence or absence of a test sample. Culture supernatant was filtered through CF50A membranes to remove IgE. The filtrate was passed through a lentil lectin Sepharose column and the column washed with 2 column volumes of DPBS. Proteins retained on the column were eluted with 0.2M α methylmannoside. The flow-through fraction combined with the wash and the eluate fraction were each dialyzed for 2 days against DPBS, and the fractions concentrated. The presence of IgE-BF in the fractions was evaluated by the ability of a fraction to inhibit rosette formation of FcεR+ B cells with IgE-coated fixed ox erythrocytes by the procedures previously described (Yodoi, et al., $J.Immunol.$, 124: 425, 1980). Mesenteric lymph node cells of rats infected with the nematode, $Nippostrongylus$ $brasiliensis$ were employed as a source of FcεR+ cells. When the 12H5 cells were cultured with mouse IgE alone, essentially all IgE-BF produced by the cells bound to lentil lectin Sepharose and was recovered by elution with a methylmannoside. Thus, the ratio of the percent rosette inhibition between the effluent/eluate fraction was less than 0.2. If a sufficient amount of GIF was added to the culture of 12H5 cells together with mouse IgE, the majority of IgE-BF formed by the cells failed to be retained in the lentil lectin Sepharose, and was recovered in the effluent fraction. Thus, GIF in a test sample was taken as (+) if the ratio of the percent rosette inhibition between the effluent/eluate fraction was 2.0 or higher.

Culture supernatants of COS-1 cells co-transfected with the plasmid SRα-hcGIF and SRα-furin have the ability to switch 12H5 cells from producing glycosylated IgE-BF to producing unglycosylated IgE-BF. When serial dilution of a 20-fold concentrated culture supernatant was assessed for GIF activity by the method described above, the activity was detected at the dilution of 1:100. A 4 ml aliquot of the concentrated supernatant was fractionated on 2 ml 388F$_1$ (monoclonal anti-GIF)-coupled Sepharose; essentially all activity (>75%) was recovered in the acid eluate fraction, in which only the 13 kDa peptide was detected. The protein was identified as GIF by Western blot. Titration of GIF bioactivity in flow-through and acid eluate fractions indicated that the activity in the former fraction was less than 1/10 of that recovered in the eluate fraction. The concentration of this 13 kDa protein in the maximal dilution of the eluate fraction for the detection of GIF activity was approximately 10 ng/ml.

The acid eluate fraction from the 388F$_1$ Affigel was further fractionated on Affigel-coupled with the γ globulin fraction of polyclonal anti-recombinant mGIF. All GIF bioactivity and the 13 kDa peptide in the fraction bound to the immunosorbent and were recovered in the acid eluate fraction. The concentration of the 13 kDa peptide in the fraction was estimated by comparison with serial dilutions of $E.$ $coli$-derived rGIF as controls. The minimum concentration of the protein required for the detection of GIF bioactivity was 5 ng/ml. The results collectively showed that the active, recombinant hGIF bound to both monoclonal anti-human GIF and polyclonal antibodies against recombinant GIF (13 kDa protein) and could be recovered by acid elution.

The same culture supernatant was fractionated on Sepharose coupled with the monoclonal anti-lipomodulin 141-B9. Again, acid eluate fraction from the immunosorbent had GIF activity.

Since human GIF could be obtained by transfection of COS-1 cells with pME pro-CT-hGIF plasmid (Example 13, D2), culture supernatant of the transfected COS cells was fractionated on 388F1 affigel, and the 13 kDa peptide recovered by acid elution was assessed for GIF biological activity. 10–20 ng/ml of the 13 kDa peptide obtained by this method was sufficient for the detection of GIF activity. The results indicated that the procedure described in Example 13D is an effective method for the formation of highly bioactive GIF.

In order to determine whether the bioactivity of recombinant hGIF is comparable to that of hybridoma-derived GIF, the GIF-producing human T cell hybridoma, 31E9 was cultured in DMEM, and GIF in culture supernatant was purified by using immunosorbent coupled with polyclonal anti-rGIF antibodies. The concentration of 13 kDa GIF in acid eluate fraction was estimated by Western blot, and the fraction was titrated for GIF activity by using 12H5 cells. The results showed that 5–14 ng/ml of the 13 kDa peptide was sufficient to switch 12H5 cells to the production of unglycosylated IgE-BF. Thus, it appears that recombinant GIF is comparable to hybridoma-derived GIF with respect to the capacity to switch the glycosylation of IgE-BF. The experiments also show that hybridoma-derived GIF reacted with the antibodies to recombinant GIF.

Since previous experiments had shown that bioactivity of murine hybridoma-derived GIF increased by 3 to 10 fold upon treatment with alkaline phosphatase (Ohno, et al., Internat.Immunol., 1: 425, 1989), it was decided to investigate this affect on the biologic activity of recombinant hGIF. Bovine serum albumin was added to affinity purified rGIF from $388F_1$-Affigel at the concentration of 2 mg/ml and dialyzed against 50 mM Tris HCl buffer (pH 8.2) containing 0.1M NaCl. One half of the preparation was mixed with sufficient insoluble alkaline phosphatase (Sigma) to give a concentration of the enzyme of 5 unit/ml, and the suspension gently mixed for 2 hr at room temperature. After this time, the enzyme was removed by centrifugation, dialyzed against RPMI 1640 medium, and GIF activity in the alkaline phosphatase-treated and untreated samples assessed. These studies showed that untreated recombinant GIF switched the 12H5 cells to the production of unglycosylated IgE-BF at a dilution of 1:30, but not at 1:60, while GIF activity in the alkaline-phosphatase-treated sample was detectable at the dilution of 1:200.

Recombinant GIF preparations obtained by transformation of E. coli or obtained by transfection of COS-1 cells with the plasmid SRαhGIF were compared for bioactivity. Purified GIF derived from the soluble fraction of E. coli (see Example 10A) was further fractionated on $388F_1$-Affigel, or polyclonal anti-GIF-couped affigel, and recovered by elution at acid pH. All of the preparations gave a single band of 13 kDa in SDS-PAGE. The concentration of the 13 kDa GIF was estimated by silver staining and GIF bioactivity of the affinity-purified GIF was titrated by using the 12H5 cells. The results showed that 100–200 ng/ml of GIF were required for switching the cells from the production of glycosylated IgE-BF to the production of unglycosylated IgE-BF. GIF from culture supernatants of COS-1 cells transfected with the plasmid SRα-hGIF was also purified using the $388F_1$-Affigel and assessed for GIF activity. The minimum concentration of the 13 kDa GIF for switching the 12H5 cells was approximately 150 ng/ml (Table XI).

TABLE XI

BIOLOGICAL ACTIVITY OF AFFINITY-PURIFIED RECOMBINANT GIF

| Recombinant GIF | Immunosorbent | Concentration[a] µg/ml | GIF-titer[b] | Minimum concentration of 13 kDa protein[c] ng/ml |
|---|---|---|---|---|
| hcGIF | $388F_1$ | 0.8 | 1:100 | 8 |
|  | 388F1 followed by poly anti-GIF 141B9 | 0.2 | 1:40 | 5 |
|  |  | 0.1 | 1:10 | 10 |
| hGIF | $388F_1$ | 1.5 | 1:10 | 150 |
| E.coli-derived GIF | $388F_1$ | 2.0 | 1:20 | 100 |
|  | unfractionated | 10.0 | 1:10 | 1000 |
|  | poly anti-GIF | 2.0 | 1:10 | 200 |

[a]Concentration of the 13 kDa GIF protein in each preparation, estimated by SDS-PAGE.
[b]GIF activity of the preparations were titrated by using the 12H5 cells.
[c]Minimum concentration of 13 kDa GIF required for switching the 12H5 cells from the formatin of glycosylated IgE-BF to the formation of unglycosylated IgE-BF.

B. Lack of macrophage migration inhibitory activity

Because of the homology between GIF and MIF in cDNA nucleotide sequences (Weiser, et al., supra, 1989), GIF was tested for MIF activity. Human MIF inhibits migration of human monocytes and the macrophages of guinea pigs and mice, therefore the activity of recombinant hGIF was determined using mouse macrophages. Three ml of sterile mineral oil was injected intraperitoneally into normal BALB/c mice and peritoneal exudate cells were recovered 3 days later. Mononuclear cells were recovered by centrifugation through a FCS layer, and a cell pellet containing approximately $5 \times 10^7$ mononuclear cells was suspended in 50 µl of prewarmed 0.35% agarose in DMEM containing 15% FCS. One µl droplets of the suspension were dispersed into the center of each well of a flat-bottomed 96-well microtiter plate, which was kept for 5 minutes on ice. DMEM supplemented with 15% FCS was added to the wells, together with a sample to be tested in a total volume of 100 µl. One test sample was assessed in triplicate or quadruplicate. The diameter of each droplet was measured under an inverted microscope. After incubation for 20–24 hours, the diameter of the outer area of the migrating cells was measured, and the migration index was calculated. The percent inhibition of migration was calculated by the following formula:

Percent inhibition=[1−migration index of test sample\migration index of migration without sample]×100

The MIF activity of rhGIF was assessed using mouse γ-interferon as a positive control. Serial dilutions of recombinant hGIF obtained by cotransfection of COS-1 cells with SRα-hcGIF and SRα-hfurin, and affinity purified by using 388F1-affigel as described above. Even though the GIF titer of the preparation was 1:100, no significant inhibition of macrophage migration was detected at the final dilution of 1:8 or 1:4. In the same experiments, 1 unit/ml of IFNγ inhibited microphage migration by 20 to 48%.

The results were confirmed by using human monocytes in agar droplets (Remold, H. G. and Menddis, A. D., Methods in Enzymology 116: 379,1985) using human MIF as a positive control. The recombinant hGIF which could switch the 12H5 cells for the formation of unglycosylated IgE-BF at a dilution of 1:100 and contained approximately 0.8 µg/ml of the 13 kDa GIF peptide, failed to inhibit the migration of human monocytes at the final dilution of 1:5. The results indicated that rhGIF was different from MIF in biological activity.

EXAMPLE 16

IN VITRO GENERATION OF ANTIGEN-SPECIFIC SUPPRESSOR T CELLS BY RECOMBINANT hcGIF

Previous experiments have shown that GIF from the rat-mouse T cell hybridoma 23A4 cells facilitated the generation of antigen-specific suppressor T cells from antigen-primed spleen cells (Iwata, M. and Ishizaka, K; *J. Immunol.* 141: 3270, 1988). When $BDF_1$ mice were immunized with alum-absorbed ovalbumin for IgE antibody response, their spleen cells constitutively secrete glycosylation enhancing factor (GEF) and produced both IgE potentiating factor (glycosylated IgE-BF) and antigen-binding GEF upon antigenic stimulation. If the antigen-primed spleen cells were stimulated by ovalbumin, and antigen-stimulated T cells were propagated by IL-2 in the presence of GIF, the cells secreted GIF. Upon antigenic stimulation, these cells produced unglycosylated IgE-BF and antigen-binding GIF, the latter of which suppressed the antibody response of syngeneic mice to DNP-OVA in carrier-specific manner. In order to explore this phenomenon more fully, it was decided to determine whether recombinant hcGIF may have the ability to generate GIF-producing T cells in vitro.

$BDF_1$ mice were primed with 1 μg ovalbumin (OVA) absorbed to aluminum hydroxide gel for IgE antibody response. Two weeks after immunization, spleen cells were obtained, and a suspension ($5 \times 10^6$ cells/ml) cultured for 3 days with 10 μg/ml OVA to activate antigen-primed T cells. An aliquot of the antigen activated cells ($2.5 \times 10^5$ cells/ml) were then propagated using recombinant mouse IL-2 (50 units/ml) in the presence or absence of rhcGIF (0.25 μg/ml). After a 4-day culture, the cells were recovered, washed 3 times, and resuspended in fresh culture medium at the concentration of $1.5 \times 10^6$ cells/ml. Four ml of the cell suspension recovered from GIF (+) or GIF (−) cultures were incubated for 24 hours with $8 \times 10^5$ OVA-pulsed LB27.4 cells which have both $Ia^b$ and $Ia^d$ (American Type Culture Collection, Rockville, Md.). Culture supernatants of antigen-stimulated T cells were absorbed with IgE-coupled Sepharose, and IgE-BF was recovered from the immunosorbent by acid elution. The flow-through fraction from the IgE-Sepharose was then fractionated on OVA-coupled Sepharose, and OVA-binding factors were recovered by elution with glycine-HCl buffer, pH 3.0. Eluates from IgE-Sepharose (i.e., IgE-BF) were fractionated on lentil lectin Sepharose to determine the nature of the factors. The results shown in Table XII indicate that the majority of IgE-BF from the T cells propagated by IL-2 alone bound to lentil lectin Sepharose and were recovered by elution with a-methylmannoside. In contrast, T cells propagated by IL-2 in the presence of hcGIF formed unglycosylated IgE-BF, which failed to be retained on lentil lectin Sepharose. Association of GEF or GIF activity with OVA-binding factors was also assessed. Upon antigenic stimulation, T cells propagated with IL-2 alone formed OVA-binding GEF, whereas T cells propagated in the presence of recombinant GIF formed OVA-binding GIF (Table XII). It has been shown that OVA-binding GIF from such T cells suppressed the antibody response of $BDF_1$ mice in an antigen (carrier)-specific manner (Iwata, M. and Ishizaka, K; *J. Immunol.*, 1988). Thus, the recombinant GIF facilitated the generation of suppressor T cells which produced antigen-specific suppressor T cell factor.

TABLE XII

GENERATION OF GIF-PRODUCING CELLS BY RECOMBINANT hcGIF AND IL-2

| Propagation of OVA-specific T cells[a] | Nature of IgE-BF[b] | OVA-binding factor[c] | |
|---|---|---|---|
| | | GEF | GIF |
| IL-2 | 4/28 | + | − |
| IL-2 + hcGIF | 26/6 | − | + |

[a]Antigen-stimulated T cells were propagated with IL-2 in the presence or absence of recombinant hcGIF.
[b]T cells propagated with IL-2 were stimulated with antigen-pulsed LB27.4 cells. IgE-BF in the supernatants were fractionated on lentil lectin Sepharose. Numbers represent percent rosette inhibition by the effluent/eluate fractions from elntil lectin Sepharose, respectively.
[c]Acid eluate fraction from OVA-Sepharose was assessed for GIF and GEF activities by using the 12H5 cells and 23A4 cells, respectively.

EXAMPLE 17

IN VIVO ACTIVITY OF RECOMBINANT GIF

In vivo activity of recombinant GIF

Previous experiments have shown that repeated injections of a GIF-enriched fraction of culture filtrates of GIF-producing hybridoma into immunized mice beginning on the day of priming resulted in suppression of both IgE and IgG antibody responses (Akasaki, M., et al., *J. Immunol.* 136: 3172, 1986). In order to determine whether recombinant GIF has the same in vivo effects, rhGIF expressed in *E. coli* (Example 10A) and that expressed in COS-1 cells (Example 13A), were purified to homogeneity by the methods described in Examples 10 and 14, and assessed for their ability to suppress the IgE and IgG1 antibody responses. $BDF_1$ mice were immunized by an i.p. injection of 0.2 μg DNP-OVA absorbed to 2 mg alum. Recombinant GIF was injected i.p. on day 0, 2, 4, 6, 8, 10 and 12, and anti-DNP antibodies in serum were measured by ELISA.

In the first experiment, *E. coli*-derived rGIF in PBS was administered at a dose of 18 μg/injection and control mice received PBS alone. Minimum concentration of rGIF for switching the 12H5 cells from the formation of glycosylated IgE-BF to the formation of unglycosylated IgE-BF was approximately 1 μg/ml. In both control and GIF-treated mice, IgE antibody titer reached maximum at 2 weeks and then declined, while IgG1 anti-DNP antibody titer continued to increase for 4–5 weeks after the immunization. Thus, IgE antibody titer at 2 weeks and IgG1 antibody titer at 4 weeks were used for comparison between the GIF-treated and untreated groups.

| Effect of *E. coli* Derived rGIF | | | |
|---|---|---|---|
| Sample | N | Anti-DNP IgE[a] | IgG1[b] |
| control | 6 | 6.7 ± 3.5 | 78.0 |
| rGIF | 3 | 1.5 ± 1.3 (p < 0.05) | 4.5 |

[a]2 weeks after immunization (μg/ml)
[b]4 weeks after immunization (μg/ml).

In the second experiment, COS-1 derived rhGIF, which was expressed by using SRα-hcGIF vector, was administered i.p. at a dose of 2.5 μg/injection. The minimum concentration of hGIF for switching the 12H5 cells for the formation of unglycosylated IgE-BF was 0.2 μg/ml. Control mice received PBS alone. The results are shown below.

| Effect of Mammalian Cell Line Derived rGIF | | |
|---|---|---|
| Sample | N | anti-DNP IgE[a] (μg/ml) |
| control | 8 | 2.6 ± 1.2 |
| rGIF | 5 | 0.70 ± 0.55 (p < 0.05) |

[a] 2 weeks after immunization.

None of the animals had adverse reactions to GIF. The example illustrates immunosuppressive effects of GIF.

EXAMPLE 18

PRODUCTION OF mAB TO ANTIGEN-SPECIFIC GLYCOSYLATION INHIBITING FACTOR

A. MATERIALS AND METHODS

1. Antigens and antibodies: Lyophilized bee venom phospholipase $A_2$ ($PLA_2$) was from Sigma Chemical Co., St. Louis, Mo. Crystalline ovalbumin (OVA) was from Nutritional Biochemical Corp., Cleveland, Ohio. Synthetic peptide corresponding to amino acid residues 13-28, and that corresponding to amino acid residues 25-40 in $PLA_2$ molecules were supplied by Dr. Howard Grey (Cytel Corp., La Jolla, Calif.). The peptide corresponding to amino acids 19-35 in $PLA_2$ molecules was synthesized by Kirin Pharmaceutical Laboratory, Maebashi, Japan. All of the synthetic peptides were purified by HPLC, and their amino acid sequences were confirmed.

The monoclonal anti-human GIF antibody, $388F_1$ (ATCC HB 10472), was described in Examples 5.

2. Cell lines: The human T cell hybridoma AC5 cells described in Example 3 expresses both CD3 and $TCR\alpha\beta$, and constitutively secretes GIF. The cells were cultured in high glucose DMEM supplemented with 10% FCS, 10% NCTC 135 medium (Gibco, Grand Island, N.Y.), 10 mM HEPES buffer, 0.2 u/ml bovine insulin (Sigma), 50 μg/ml sodium pyruvate, 150 μg/ml oxaloacetic acid and antibiotics.

B cell hybridomas that produce anti-human GIF were constructed from spleen cells of BALB/c mice (Jackson Lab, Bar Harbor, Me.) that had been immunized with affinity-purified antigen-binding GIF (see below). One week after the last booster immunization, the spleen cells were fused with hypoxanthine phosphoribotransferase-deficient Sp2/0 AG14 cells (Schulman, et al., *Nature*, 271: 269, 1978) by the procedures described (Iwata, et al., *J. Immunol.*, 132: 1286, 1984). Subcloning of the hybridomas was carried out by lmiting dilution. The hybridomas were maintained in complete DMEM described above.

3. Fractionation and purification of GIF: Nonspecific GIF in culture supernatants of unstimulated AC5 cells in serum-free medium was enriched by chromatography on a DEAE Sepharose column. Culture supernatants were concentrated 20 to 100 fold, diluted 3 fold with distilled water, adjusted to pH 8.0 with Tris, and then passed through a DEAE Sepharose (Pharmacia) column which had been equilibrated with 10 mM Tris HCl buffer, pH 8.0, containing 50 mM NaCl. Flow-through fraction and washing of the column with the buffer were combined and concentrated. Nonspecific GIF in the original culture supernatant was affinity-purified by using 388 $F_1$-coupled Affigel. Concentrated culture supernatant was recycled overnight through the immunosorbent. After washing with 30 column volumes of DPBS, proteins bound to the immunosorbent were recovered by elution with 0.1M glycine HCl buffer, pH 3.0.

To produce antigen-binding GIF, AC5 cells were stimulated by cross-linking of CD3 (Thomas, et al., *J.Immunol.* 148: 729, 1992). The cells ($5\times10^6$ ml) were treated with 5 μg/ml of monoclonal anti-CD3 ($SPV-T_3b$) for 30 minutes at 4° C., and the antibody-treated cells were incubated for 30 minutes at 4° C. with 10 μg/ml anti-mouse Ig. After washing, the cells were resuspended in ABC medium at $2\times10^6$ cells/ml, and cultured for 24 hours. Culture supernatants were concentrated 10 to 15 fold by ultrafiltration, and recycled overnight through a $PLA_2$-coupled Sepharose column. The column was washed with DPBS and proteins remaining in the column were recovered by elutin with 0.1M glycine HCl buffer, pH 3.0.

Affinity purified GIF was fractionated by gel filtration through a Superose 12 column (1.6×50 cm, Pharmacia) connected to HPLC (Beckman System Gold, Fullteron, Calif.). Proteins were eluted from the column with PBS at a flow rate of 0.85 ml/min. The column was calibrated with BSA (m.w. 67,000), OVA (m.w. 43,000), soybean trypsin inhibitor (m.w. 20,100) and cytochrome c. (m.w. 12,500). In some experiments, affinity-purified GIF preparation was reduced and alkylated. The GIF preparation in 0.05M Tris HCl buffer containing 0.15M NaCl was incubated for 1 hour at room temperature with 10 mM dithiothreitol and then alkylated with 30% molar excess of iodoacetamide. The reduced and alkylated sample was applied to the same Superose 12 column, and proteins were eluted with PBS.

4. ELISA assays: Each well of a Nunc F plate (Max Sorp, Nunc) was coated with 50 μl of serial dilutions of a GIF preparation overnight at 4° C. in duplicate or triplicate. Plates were washed five times with phosphate buffered saline containing 0.05% Tween 20 (Sigma) between each of the following steps except the step prior to addition of substrate. The plates were blocked with 2% BSA in Tween/PBS for 1 hour at 37° C. Binding of mAb $388F_1$ to GIF was detected with an amplification system. Fifty μl of PBS containing 150 ng/ml of biothinylated mAb $388F_1$ were added to each well. After 2 hours of incubation at 37° C., followed by washing, 50 μl of an appropriate dilution (1:6000) of streptavidin-coupled alkaline phosphatase (Zymed) was added to each well and the plate was incubated for 2 hours at 37° C. The plate was washed with 0.05% Tween 20 in 0.05M Tris HCl buffer, pH 7.5, containing 0.15M NaCl, and an ELISA signal was developed by 30 min incubation with 50 μl of alkaline phosphatase substrate followed by amplifier solution (GIBCO/Bethesda Research Lab). Absorbances at 490 nm was determined in an ELISA reader MR 5000 (Dynatech).

ELISA was also set up with mAB against antigen-binding GIF. After Max-Sorp plates were coated with a GIF-preparation and blocked with BSA, 50 μl of the mAb (200 ng/ml) in PBS was added to each well and the plate was incubated for 2 hours at 37° C. Depending on the isotype of the mAb, a 1:3000 dilution of horse radish peroxidase (HRP)-coupled goat anti-mouse IgM (Biorad) or anti-mouse IgG (Zymed) or a 1:2000 dilution of HRP-coupled anti-mouse IgG+A+M (Zymed) was added to each well. ELISA signal was developed by peroxidase substrate (Zymed), and determined by absorption at 405 nm.

5. SDS-PAGE and immunoblotting: Affinity-purified GIF was dialyzed against 0.01% SDS and lyophilized. Samples were then analyzed by SDS gel electrophoresis in 15% polyacrylamide slab gel by using the Laemeli system (Laemeli, U.K., *Nature*, 227: 680, 1980). Protein bands were detected by silver staining (Ochs, et al., *Electrophoresis*, 2: 304, 1981). For immunoblotting, affinity-purified GIF was analyzed by SDS-PAGE under reducing conditions. Purified recombinant GIF from *E.coli* was electrophoresed in parallel as a standard. Proteins in SDS-PAGE gel were blotted to PVDF membrane (Immobilon-P, Millipore), and the membrane was blocked by incubating with Blocker Blotto (Pierce) overnight at 4° C. After washing with 0.05% Tween 20 in PBS, pH 7.5, membrane was treated with 1 μg/ml of IgG fraction of rabbit anti-rGIF for 1 hour at 37° C. Binding of rabbit IgG to protein bands was detected by using HRP-coupled donkey anti-rabbit IgG and ECL Western blotting detection reagents (Amersham), followed by autoradiography. The position of rGIF band on x-ray film was used as 14 kDa standard.

B. Preparation of monoclonal antibodies specific for antigen-binding GIF

AC5 cells were treated with anti-CD3 followed by anti-MGG, and antigen-binding GIF in the supernatant was affinity purified by using PLA$_2$-coupled Sepharose. The preparation could switch the 12H5 cells from the production of glycosylated IgE-BF to the production of unglycosylated IgE-BF at a dilution of 1:30 to 1:60. BALB/c mice were immunized by an i.p. injection of 0.1 ml of the preparation in CFA followed by 5 booster injections of the same antigen in incomplete Freund's adjuvant. Two weeks after the last booster injection, the animals were sacrificed and their spleen cells fused with the B cell line SP 2/0 AG14.

Culture supernatants of hybridomas were tested for the presence of mouse Ig. Those hybridomas which produced Ig were further tested for the presence of anti-GIF by ELISA assays. Maxi-Sorp wells were coated with PLA$_2$-binding GIF, and binding of mouse Ig in the culture supernatant to the GIF-coated wells was determined by using HRP-coupled anti-mouse IgG+A+M. Culture supernatants of 8 hybridomas gave substantial absorbance by ELISA. The presence of anti-GIF antibody in the supernatants of the 8 hybridomas was confirmed by incubating an aliquot of affinity-purified PLA$_2$-binding GIF with each culture supernatant, followed by filtration of the mixture through Centricon 100 (Amersham). Assay of the filtrates for GIF activity showed that the antibodies from all 8 of the hybridomas bound GIF, whereas filtrate of PLA$_2$-binding GIF itself had the activity.

The same culture supernatants were then examined for the presence of monoclonal antibody against nonspecific GIF. Maxi-Sorp plates were coated with either affinity-purified nonspecific GIF or antigen-specific GIF, and culture supernatant of each B cell hybridoma was added to the wells. After 2 hr incubation at 37° C., the wells were washed and a 1:2000 dilution of HRP-coupled goat anti-mouse IgG+A+M was added to each well. ELISA signal was developed by peroxidase substrate and measured at 405 nm. Absorption of control wells, which were coated with GIF and incubated with HRP-coupled antibodies and substrates, was subtracted. The results of the experiments indicated that only two hybridomas, i.e., 110 and 205, gave substantially higher ELISA signal with PLA$_2$-binding GIF (i.e., antigen specific GIF) than with antigen non specific GIF. The hybridomas 110 and 205 were subcloned by limiting dilutions, and culture supernatant of each clone was tested again by ELISA for the selective binding of monoclonal antibodies to PLA$_2$-binding GIF. After repeated subclonings, subclones of each of the two hybridomas, i.e., 110BH3 and 205AD2, were obtained whose culture supernatants gave ELISA signals only with antigen binding GIF. The monoclonal antibody 110BH3 was μκ isotype, while 205AD2 was γ$_1$κ isotype.

Confirmation that both monoclonal antibodies bound PLA$_2$-specific GIF but failed to bind nonspecific GIF was performed in a bioassay. Aliquots of the GIF preparations were incubated overnight with the culture supernatant of either 110BH3 cells or 205AD2 cells, and the mixtures were filtered through Centricon 100. Determination of GIF activity in the filtrates by using the 12H5 cells showed that both antibodies bound PLA$_2$-binding GIF, but failed to bind nonspecific GIF. Next, the mAb 110BH3 was enriched from the culture supernatant of the hybridoma by precipitation with 1/3 saturation of ammonium sulfate, and 5 mg of IgM were coupled to 1.5 ml of Sepharose. The PLA$_2$-binding GIF and nonspecific GIF from the AC5 cells were then fractionated on the antibody-coupled Sepharose. The PLA$_2$-binding GIF was prepared from culture supernatants of anti-CD3-treated AC5 cells by affinity-purification on PLA$_2$-coupled Sepharose, while nonspecific GIF was prepared from culture supernatants of unstimulated AC5 cells by using 388F$_1$-coupled Sepharose. The results shown in Table XII indicated that PLA$_2$-binding GIF bound to the immunosorbent and was recovered by elution at acid pH, while nonspecific GIF failed to be retained on the immunosorbent.

TABLE XIII

FRACTIONATION OF GIF PREPARATIONS ON 110 BH3-COUPLED SEPHAROSE$^a$

| FRACTION FROM IMMUNOSORBENT$^b$ | PLA$_2$-BINDING GIF | | NON-SPECIFIC GIF | |
|---|---|---|---|---|
| | Dilution | GIF Activity$^c$ | Dilution | GIF activity$^c$ |
| Unfractionated | 1:10 | 25/0(+) | 1:30 | 28/0(+) |
| Flow-through | 1:2 | 0/30(−) | 1:30 | 29/4(+) |
| Wash | 1:2 | 0/23(−) | 1:2 | 3/32(−) |
| Eluate | 1:10 | 25/0(+) | 1:2 | 0/30(−) |
| Medium control | | 0/33 | | 1/30 |

$^a$PLA$_2$-binding GIF and nonspecific GIF could switch the 12H5 cells from the formation of glycosylated IgE-BF to the formation of unglycosylated IgE-BF at the dilution of 1:10 and 1:30, respectively.
$^b$One ml of GIF preparation was mixed with 0.25 ml of 110 BH3-coupled Sepharose. Flow-through fraction and 1 ml washing with DPBS were combined (Flow-through fraction). Columns were washed with 5 ml BPBS (wash) and then eluted with 1 ml glycine HCl buffer, pH 3.0 (Eluate). After dialysis, each fraction was concentrated to 1.0 ml for GIF assay.
$^c$GIF activity was determined by using 12H5 cells. Numbers in this column represent percent rosette inhibition by the effluent/eluate fractions from lentil lectin Sepharose (c.f. method). (+)(−) indicate presence or absence of GIF activity.

Attempts were made to detect antigen-binding GIF and nonspecific GIF by ELISA. Nonspecific GIF was enriched by fractionation of culture supernatants of unstimulated AC5 cells by ion-exchange column chromatography on a DEAE-Sepharose column. Flow-through fraction with Tris buffer containing 50 mM NaCl was concentrated. The antigen-binding factors in the culture supernatants of anti-CD3-stimulated cells were purified by using PLA$_2$-coupled Sepharose, and the factors in acid eluates was further fractionated on 110BH3-coupled Sepharose. Both antigen-specific and nonspecific GIF preparations switched the 12H5 cells from the formation of glycosylated IgE-BF to the formation of unglycosylated IgE-BF at a dilution of 1:60. Next, Max-Sorb wells were coated with serial dilutions of one of the preparations and, after blocking, the mAb 388F$_1$ or 110 BH3 was applied to the wells. mAb 388F$_1$ gave ELISA signals with both nonspecific GIF and antigen-binding GIF preparations, while mAb 110-BH3 reacted with antigen-binding factor, but not with the nonspecific GIF. The ELISA signals appear to be due to specific binding of mAb because no signal was detected when the mAb was replaced with irrelevant IgG$_{2a}$ or IgM in the assays.

Since the affinity purified antigen-binding factor described above was obtained by using PLA$_2$-Sepharose followed by 110BH3-Sepharose, and the preparation was analyzed by SDS-PAGE. Antigen-binding GIF was purified by using PLA$_2$-coupled Sepharose, followed by 110BH3-coupled Sepharose. Acid eluate fraction from the immunosorbent was dialyzed against distilled water in the presence of 0.01% SDS and lyophilized. The preparation was analyzed by SDS-PAGE under reducing and non-reducing conditions and silver staining. Under non-reducing conditions, the preparation gave three major bands of 85 kDa, 66 kDa, 58 kDa and a minor band of 13 kDa. Under reducing conditions, the 85 kDa band disappeared and several new bands were detected. Since one of the major bands detected under reducing conditions was 14 kDa, the mobility of which corresponded to that of nonspecific GIF, analysis was done to determine if this band was GIF. Another preparation of antigen-binding GIF was obtained from the culture supernatant of anti-CD3-stimulated AC5 cells by affinity chromatography on 110BH3-Sepharose. Titration of GIF activity in serial dilutions of flow-through fraction and acid eluate fractions from the immunosorbent using 12H5 cells showed that the majority of GIF activity in the culture supernatant bound to the immunosorbent and was recovered by acid elution. Activity was detected in a 1:30 dilution of the eluate fraction, while the flow-through fraction gave the GIF titer of 1:6. As shown in Table XIV, the eluate fraction gave ELISA signal with both mAb 110BH3 and 205AD2, while the effluent fraction failed to give a significant ELISA signal with the antibody. When antibody to nonspecific GIF (388F$_1$) was employed, however, the flow-through fraction gave a weak but definite ELISA signal, although the eluate fraction contained much higher concentration of GIF. The eluate fraction was then analyzed by SDS-PAGE under reducing conditions followed by immunblotting using polyclonal antibodies against rGIF. Recombinant GIF from *E. coli* was applied to the next well of the same gel. After electrophoresis under reducing conditions, proteins in the gels were transferred to PVDF membranes, which were then treated with γ globulin fraction of anti-rGIF. In both membranes, rGIF employed as a control gave a clear band on X-ray film (not shown). Since molecular weight markers did not include any protein of less than 18 kDa, rGIF band on x-ray film was used as 13 kDa marker. The results indicated that the antibodies actually bound to the 13 kDa band. The relationship between the 13 kDa band and nonspecific GIF was confirmed by analyzing nonspecific GIF, which was purified from culture supernatant of unstimulated AC5 cells by affinity chromatography on 388F$_1$-coupled Sepharose. Analysis of the nonspecific GIF preparation by SDS-PAGE and immunoblotting with anti-rGIF antibodies showed that this preparation also contained a 13 kDa protein which reacted with the antibodies.

TABLE XIV

DISTRIBUTION OF GIF ACTIVITY AND GIF ANTIGENS BETWEEN FLOW-THROUGH AND ELUATE FRACTIONS FROM 110BH3-SEPHAROSE[a]

| FRACTION FROM 110-BH3-SEPHAROSE | GIF[b] TITER | ELISA SIGNAL | | |
|---|---|---|---|---|
| | | 205DA2[c] | 110BH3[c] | 388F$_1$[d] |
| Flow-through | 1:3 | 0.063 | 0.093 | 0.36 |
| Acid-eluate | 1:15 | 0.750 | 1.068 | 0.86 |

[a]Culture supernatant of anti-CD3-treated cells was concentrated and fractionated on 110BH3-Sepharose. Fractions were concentrated to original volume of the concentrated supernatant, diluted twice and then titrated for GIF activity and ELISA assays.
[b]Maximal dilution of the fraction that could switch the 12H5 cells from the formation of glycosylated IgE-BF to the formation of unglycosylated IgE-BF.
[c]Absorption at 405 nm.
[d]Absorption at 490 nm.

It was suspected that the 13 kDa GIF and an antigen-binding polypeptide chain were associated with each other to form antigen-binding GIF. If this was the case, the molecular size of antigen-binding GIF would be larger than that of nonspecific GIF under physiological conditions. To test this possibility, PLA$_2$-binding GIF from AC5 cells was partially purified by using 110-BH3-Sepharose, and the preparation was fractionated by gel filtration through a Superose 12 column. Each fraction was assessed for antigen-binding GIF by ELISA using mAb 388F$_1$ and 110 BH3. The results indicated that the majority of GIF, which was detected by mAb 388F$_1$, was eluted from the column between 55.5 and 60.5 min. with a peak at 58.5 min. The size of the molecule, estimated from its elution time, was 74 kDa. As expected, the fractions contained GIF activity as determined by bioassay using 12H5 cells. It should be noted that the GIF-containing fractions gave ELISA signal with mAb 110BH3. The results strongly suggest that the antigenic determinant recognized by mAb 388F$_1$ and that recognized by mAb 110BH3 are associated with the same molecules.

If antigen-binding GIF actually consists of an antigen-binding chain and nonspecific GIF, the antigen-binding GIF may be dissociated into separate polypeptides by reduction and alkylation treatment.

In order to investigate this possibility, affinity-purified antigen-binding GIF was reduced in 10 mM DTT. After alkylation with iodoacetamide, the sample was applied to the same Superose 12 column, and the distribution of 388F$_1$-antigen and 110BH3-antigen was determined by ELISA. The results indicated that approximately one half of GIF in the reduced and alkylated material was recovered in a fraction of which elution time corresponded to that of 15 kDa molecule. Since the same fraction did not contain GIF when the original antigen-binding GIF was fractionated, the 15 kDa GIF appears to be derived from the antigen-binding GIF. The experiment also showed two peaks of molecules recognized by 110BH3; the first peak corresponded to the original antigen-binding GIF, while the elution time of the second peak corresponded to 62–64 kDa. Since the latter fraction did not contain a significant amount of GIF, as determined by ELISA, the protein in the fraction should represent a cleavage product of antigen-binding GIF responsible for antigen specific binding.

C. Epitope specificity of antigen-binding GIF

Experiments were carried out to confirm that the PLA$_2$-binding GIF is specific for bee venom PLA$_2$. The antigen-binding GIF was purified from culture supernatants of anti-CD3-stimulated AC5 cells by absorption with PLA$_2$-coupled Sepharose followed by elution of bound proteins at acid pH. An aliquot of the preparation was mixed overnight with OVA-coupled Sepharose, and GIF activity in the flow-through and acid eluate fractions was determined. As expected, essentially all GIF activity failed to be retained in OVA-Sepharose, and was recovered in a flow-through fraction. The OVA-Sepharose was washed with DPBS, and the immunosorbent was eluted with glycine-HCl buffer, pH 3.0. However, GIF activity was not detected in the acid eluate fraction.

Since previous experiments on PLA$_2$-binding GIF from the murine Ts hybridoma 3B3 have shown that the factor had affinity for the peptide representing amino acid residues 19-34 in bee venom PLA$_2$ molecules, it was decided to investigate whether human antigen-binding GIF from AC5 cells might bind to Sepharose coupled with the synthetic peptide, representing amino acids 19-35 from PLA$_2$ molecules. As shown in Table XV, essentially all GIF activity in the preparation was absorbed with the p19-35-Sepharose, and was recovered by elution at acid pH. In order to confirm the epitope specificity, aliquots of the PLA$_2$-binding GIF were incubated for 6 hours with 0.2 mg/ml of a synthetic peptide, representing amino acid 13-28, 19-35, or 25-40, and each mixture was absorbed with PLA$_2$-Sepharose. Determination of GIF activity in the flow-through fraction and acid eluate fraction indicated that the binding of GIF to PLA$_2$-Sepharose was prevented by p13-28 or p19-35, but not by p25-40 (Table XV). The results were confirmed by ELISA. When the PLA$_2$-binding GIF was absorbed with PLA$_2$-Sepharose in the presence or absence of p25-40, acid eluate fraction from the immunosorbent gave ELISA signal with 110BH3, while the flow-through fraction failed to give the signal. If the same PLA$_2$-binding GIF was absorbed with the same immunosorbent in the presence of p19-35, the flow-through fraction, but not the acid eluate fraction, gave ELISA signal with the monoclonal antibody. The results collectively show that the sequence of amino acid 19-28 in the PLA$_2$ molecule contained the epitope which was recognized by antigen-binding GIF.

TABLE XV

EPITOPE SPECIFICITY OF PLA$_2$-BINDING GIF

| EXP | IMMUNOSORBENT | PEPTIDE ADDED | GIF ACTIVITY[c] Flow-through | Eluate |
|---|---|---|---|---|
| 1[a] | PLA$_2$-Sepharose | none | 2/28(−) | 23/6(+) |
|  | P19-35-Sepharose | none | 3/30(−) | 28/4(+) |
|  | Medium Control | none | 4/28 | — |
| 2[b] | PLA$_2$-Sepharose | none | 0/28(−) | 27/3(+) |
|  |  | P13-28 | 22/0(+) | 0/23(−) |
|  |  | P19-35 | 20/5(+) | 0/28(−) |
|  |  | P25-40 | 2/25(−) | 23/0 (+) |
|  | Medium Control | none | 3/24 | — |

[a]6 ml of acid eluate fraction from PLA$_2$-Sepharose, of which GIF titer was 1:10, was fractionated on 1.5 ml of Sepharose coupled with P19-35. Each of the flow-through, wash and acid eluate fractions were adjusted to 6.0 ml, and their GIF activity was determined by using 12H5 cells.
[b]A 0.5 ml aliquot of the acid eluate fraction from PLA$_2$-Sepharose, of which GIF titer was 1:30, was mixed overnight with 0.5 ml PLA$_2$-Sepharose in the presence or absence of the appropriate peptide. Both flow-through and acid eluate fractions from PLA$_2$-sepharose were adjusted to 1.0 ml, dialyzed against RPMI 1640 medium, and assessed for GIF activity. One ml of a suspension of 12H5 cells was mixed with an equal volume of a sample to be tested, and cultured in the presence of IgE.
[c]Values represent precent rosette inhibition by the effluent/eluate fractions from lentil lectin Sepharose. (+)(−) indicate the presence or absence of GIF.

Deposit of Materials

The following cell lines have been deposited with the American Type Culture Collection, 1301 Parklawn Drive, Rockville, Md., USA (ATCC):

| Cell Line | ATCC Accession No. | Deposit Date |
|---|---|---|
| 388F$_1$ | HB 10472 | May 31, 1990 |
| AC5 | HB 10473 | May 31, 1990 |
| 31E9 | HB 11052 | June 2, 1992 |
| 110BH3 | Y | May 14, 1993 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

SUMMARY OF SEQUENCES

Sequence ID No. 1 is the amino acid sequence of peptide AP-1 (page 64, line 16);

Sequence ID No. 2 is the amino acid sequence of peptide AP-23 (page 64, line 17);

Sequence ID No. 3 is the amino acid sequence of peptide AN-4 (page 65, line 2);

Sequence ID No. 4 is the amino acid sequence of peptide AN-5 (page 65, line 3);

Sequence ID No. 5 is the amino acid sequence of peptide AN-7 (page 65, line 5);

Sequence ID No. 6 is the amino acid sequence of peptide T-1 (page 65, line 12);

Sequence ID No. 7 is the amino acid sequence of the N-terminal PVDF-immobilized protein of murine GIF (page 65, line 15);

Sequence ID No. 8 is the nucleotide sequence of a 5'→3' primer used for murine GIF cDNA cloning (page 66, line 1);

Sequence ID No. 9 is the nucleotide sequence of a 5'→3' primer used for murine GIF cDNA cloning (page 66, line 2);

Sequence ID No. 10 is the nucleotide sequence of a 5'→3' primer used for human GIF cDNA cloning (page 70, lines 1 and 2);

Sequence ID No. 11 is the nucleotide sequence of a 3'→5' primer used for human GIF cDNA cloning (page 70, line 3);

Sequence ID No. 12 is the nucleotide sequence of a 5'→3' primer used to generate AflII and BamHI restriction sites at both ends of murine GIF cDNA (page 71, lines 5 and 6);

Sequence ID No. 13 is the nucleotide sequence of a 3'→5' primer used to generate AflII and BamHI restriction sites at both ends of murine GIF cDNA (page 71, line 7);

Sequence ID No. 14 is the nucleotide sequence of a 5'→3' primer used to generate BglII or KpnI sites on human GIF cDNA (page 76, line 17; page 78, line 17);

Sequence ID No. 15 is the nucleotide sequence of a 3'→5' primer used to generate BglII or KpnI sites on human GIF cDNA (page 76, line 18; page 78, line 18);

Sequence ID No. 16 is the nucleotide sequence of a 5'→3' primer having a PstI (page 78, line 12);

Sequence ID No. 17 is the nucleotide sequence of a 3'→5' primer having a PstI (page 78, line 13);

Sequence ID Nos. 18, 20, and 22 are nucleotide sequences of 5'→3' primers for cloning human furin cDNA (page 80, lines 3, 5, and 7);

Sequence ID Nos. 19, 21, and 23 nucleotide sequences of 3'→5' primers for cloning human furin cDNA (page 80, lines 4, 6, and 8);

Sequence ID No. 24 is the nucleotide sequence of a primer (CT1) for human pro-ct (page 83, line 5);

Sequence ID No. 25 is the nucleotide sequence (and deduced amino acid sequence) of a primer (CT2) for human pro-ct (page 83, line 5);

Sequence ID No. 26 is the deduced amino acid sequence for the primer (CT2) for human pro-ct;

Sequence ID No. 27 is the nucleotide sequence (and deduced amino acid sequence) of a primer (CT3) for human pro-ct (page 83, line 5);

Sequence ID No. 28 is the deduced amino acid sequence for the primer (CT3) for human pro-ct;

Sequence ID No. 29 is the nucleotide sequence (and deduced amino acid) of a primer (CT4) for human pro-ct (page 83, line 5);

Sequence ID No. 30 is the deduced amino acid sequence for the primer (CT4) for human pro-ct;

Sequence ID No. 31 is the nucleotide sequence (and deduced amino acid) of a primer (CT5) for human pro-ct (page 83, line 5);

Sequence ID No. 32 is the deduced amino acid sequence for the primer (CT5) for human pro-ct;

Sequence ID No. 33 is the nucleotide sequence of a 5' end primer, G1, for isolation of Fc cDNA (page 84, line 23);

Sequence ID No. 34 is the nucleotide sequence of a 3' end primer, G2, for isolation of Fc cDNA (page 84, line 24);

Sequence ID No. 35 is the nucleotide sequence (and deduced amino acid sequence) for a murine GIF (FIG. 1);

Sequence ID No. 36 is the deduced amino acid sequence for the murine GIF (FIG. 1);

Sequence ID No. 37 is the nucleotide sequence (and deduced amino acid sequence) for a human GIF (FIG. 2); and Sequence ID No. 38 is the deduced amino acid sequence for the human GIF (FIG. 2).

---

We claim:

1. The method of producing a substantially pure, biologically active antigen non-specific glycosylation inhibiting factor (GIF) which comprises:

culturing a eukaryotic cell transformed with a polynucleotide sequence encoding a fusion polypeptide of the formula:

$R_1$-$R_2$ wherein $R_1$ is a pro-region of a precursor of a secretory protein, $R_2$ is an amino acid sequence as in SEQ ID NO:36 or SEQ ID NO:38, the carboxy terminus of the pro-region contains or is modified to contain the sequence $((X_1X_2)_n$-Lys-Arg), wherein n is either 1 or 2, $X_1$ is Lys or Arg, and $X_2$ is any amino acid; and isolating substantially pure antigen non-specific GIF.

2. The method of claim 1, wherein the pro-region is calcitonin precursor.

3. A substantially pure fusion polypeptide of the formula:

$R_1$-$R_2$ wherein $R_1$ is a pro-region of a precursor of a secretory protein, $R_2$ is an amino acid sequence as in SEQ ID NO:36 or SEQ ID NO:38, and the carboxy terminus of the pro-region contains or is modified to contain the sequence $(X_1X_2)_n$-Lys-Arg), wherein n is either 1 or 2, $X_1$ is Lys or Arg, and $X_2$ is any amino acid.

4. The fusion polypeptide of claim 3, wherein the pro-region is calcitonin precursor.

5. An isolated polynucleotide sequence which encodes a substantially pure fusion polypeptide of the formula:

$R_1$-$R_2$ wherein $R_1$ is a pro-region of a precursor of a secretory protein, $R_2$ is an amino acid sequence as in SEQ ID NO:36 or SEQ ID NO:38, and the carboxy terminus of the pro-region contains or is modified to contain the sequence $((X_1X_2)_n$-Lys-Arg), wherein n is either 1 or 2, $X_1$ is Lys or Arg, and $X_2$ is any amino acid.

6. A recombinant expression vector containing the polynucleotide of claim 5.

7. The vector of claim 6, wherein the vector is a virus.

8. The vector of claim 6, wherein the vector is a plasmid.

9. A host cell containing the vector of claim 6.

10. The host cell of claim 9, wherein the host cell is a eukaryote cell.

11. The host cell of claim 10, wherein the host cell is a COS-1 cell.

12. An isolated polynucleotide sequence encoding antigen non-specific GIF polypeptide as in SEQ ID NO:36 or SEQ ID NO:38.

13. The polynucleotide of claim 12, wherein the GIF sequence is selected from the group consisting of SEQ ID NO:35 and SEQ ID NO:37.

14. A recombinant vector containing the polynucleotide sequence of claim 12.

15. The vector of claim 14, wherein the vector is a virus.

16. The vector of claim 14, wherein the vector is a plasmid.

17. A host cell containing the vector of claim 14.

18. The host cell of claim 17, wherein the host cell is a prokaryote cell.

19. The host cell of claim 18, wherein the host cell is *E.coli*.

20. The host cell of claim 17, wherein the host cell is a eukaryote cell.

21. The host cell of claim 20, wherein the host cell is a COS-1 cell.

22. A method of producing biologically active GIF which comprises:

a) culturing a host cell of claim 17; and b) isolating substantially pure GIF from the culture.

23. The method of claim 22, wherein the host cell is a eukaryote cell.

24. The method of claim 23, wherein the host cell is a COS-1 cell.

25. The method of claim 22, wherein the host cell is a prokaryote cell.

26. The method of claim 25, wherein the prokaryote cell is *E. coli*.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: AP-1

( i x ) FEATURE:
      ( A ) NAME/KEY: Peptide
      ( B ) LOCATION: 1..11

( x i ) SEQUENCE DESCRIPTION: SEQ ID NO:1:

```
Ile Gly Gly Ala Gln Asn Arg Asn Tyr Ser Lys
 1               5                   10
```

( 2 ) INFORMATION FOR SEQ ID NO:2:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: AP-23

( i x ) FEATURE:
      ( A ) NAME/KEY: Peptide
      ( B ) LOCATION: 1..20

( x i ) SEQUENCE DESCRIPTION: SEQ ID NO:2:

Leu Leu Cys Gly Leu Leu Ser Asp Arg Leu His Ile Ser Pro Asp Arg
1               5                   10                  15

Val Tyr Ile Asn
            20

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: AN-4

(ix) FEATURE:
        (A) NAME/KEY: Peptide
        (B) LOCATION: 1..15

(xi) SEQUENCE DESCRIPTION: SEQ ID NO:3:

Asp Met Asn Ala Ala Asn Val Gly Xaa Asn Gly Ser Thr Phe Ala
1               5                   10                  15

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: AN-5

(ix) FEATURE:
        (A) NAME/KEY: Peptide
        (B) LOCATION: 1..13

(xi) SEQUENCE DESCRIPTION: SEQ ID NO:4:

Asp Pro Cys Ala Leu Cys Ser Leu His Ser Ile Gly Lys
1               5                   10

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: AN-7

(ix) FEATURE:
        (A) NAME/KEY: Peptide
        (B) LOCATION: 1..15

(xi) SEQUENCE DESCRIPTION: SEQ ID NO:5:

Asp Arg Leu His Ile Ser Pro Asp Arg Val Tyr Ile Asn Tyr Tyr
1               5                   10                  15

(2) INFORMATION FOR SEQ ID NO:6:

(i) SEQUENCE CHARACTERISTICS:
        (A) LENGTH: 11 amino acids (B) TYPE: amino acid
                (C) STRANDEDNESS: single
                (D) TOPOLOGY: linear (ii) MOLECULE TYPE: peptide (vii) IMMEDIATE SOURCE:
                (B) CLONE: T-1

(ix) FEATURE:
                (A) NAME/KEY: Peptide
                (B) LOCATION: 1..11

(xi) SEQUENCE DESCRIPTION: SEQ ID NO:6:

Pro  Met  Phe  Ile  Val  Asn  Thr  Asn  Val  Pro  Arg
    1                   5                        10

(2) INFORMATION FOR SEQ ID NO:7:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: peptide (vii) IMMEDIATE SOURCE:
                (B) CLONE: N-terminal (ix) FEATURE:
                (A) NAME/KEY: Peptide
                (B) LOCATION: 1..15

(xi) SEQUENCE DESCRIPTION: SEQ ID NO:7:

Met  Pro  Met  Phe  Ile  Val  Asn  Thr  Asn  Val  Pro  Arg  Ala  Ser  Val
    1                   5                        10                        15

(2) INFORMATION FOR SEQ ID NO:8:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: CDS
                (B) LOCATION: 1..36

(xi) SEQUENCE DESCRIPTION: SEQ ID NO:8:

ATGCCGATGT TCATCGTAAA CACCAACGTG CCCCGC                                    36

(2) INFORMATION FOR SEQ ID NO:9:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: CDS
                (B) LOCATION: 1..36

(xi) SEQUENCE DESCRIPTION: SEQ ID NO:9:

GCCGATGCTG TGCAGGCTGC AGAGCGCGCA CGGCTC                                    36

( 2 ) INFORMATION FOR SEQ ID NO:10:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..60

( x i ) SEQUENCE DESCRIPTION: SEQ ID NO:10:

AACCTTAAGA AAAACCAAGG AGGTAATAAA TAATGCCGAT GTTCATCGTA AACACCAACG        60

( 2 ) INFORMATION FOR SEQ ID NO:11:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..42

( x i ) SEQUENCE DESCRIPTION: SEQ ID NO:11:

CACCCGACCT TGTTGAGGTG GAAGCGGATT ATCCCTAGGC AA        42

( 2 ) INFORMATION FOR SEQ ID NO:12:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..60

( x i ) SEQUENCE DESCRIPTION: SEQ ID NO:12:

AACCTTAAGA AAAACCAAGG AGGTAATAAA TAATGCCTAT GTTCATCGTG AACACCAATG        60

( 2 ) INFORMATION FOR SEQ ID NO:13:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..43

( x i ) SEQUENCE DESCRIPTION: SEQ ID NO:13:

GCACCCGACC TTGCCAAGGT GGAAGCGAAC TATCCCTAGG CAA        43

( 2 ) INFORMATION FOR SEQ ID NO:14:

( i ) SEQUENCE CHARACTERISTICS:
    ( A ) LENGTH: 39 base pairs ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..39

( x i ) SEQUENCE DESCRIPTION: SEQ ID NO:14:

CCCAGATCTA AGCGGATGCC GATGTTCATC GTAAACACC   39

( 2 ) INFORMATION FOR SEQ ID NO:15:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..32

( x i ) SEQUENCE DESCRIPTION: SEQ ID NO:15:

CCTTGTTGAG GTGGAAGCGG ATTCCATGGC AA   32

( 2 ) INFORMATION FOR SEQ ID NO:16:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..26

( x i ) SEQUENCE DESCRIPTION: SEQ ID NO:16:

AACTGCAGAT GGGCTTCCAA AAGTTC   26

( 2 ) INFORMATION FOR SEQ ID NO:17:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..32

( x i ) SEQUENCE DESCRIPTION: SEQ ID NO:17:

GACCTGTCGG GGTCTAGATT CGCCGACGTC CA   32

( 2 ) INFORMATION FOR SEQ ID NO:18:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear (i i) MOLECULE TYPE: DNA (genomic)

(i x) FEATURE:
    (A) NAME/KEY: CDS
    (B) LOCATION: 1..33

(x i) SEQUENCE DESCRIPTION: SEQ ID NO:18:

AAGAATTCCC CCATGGAGCT GAGGCCCTGG TTG     33

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..28

(x i) SEQUENCE DESCRIPTION: SEQ ID NO:19:

GTGGTTGTCA TAGATGTGCG ACAGGTAG     28

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..28

(x i) SEQUENCE DESCRIPTION: SEQ ID NO:20:

ACACCAACAG TATCTACACG CTGTCCAT     28

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..28

(x i) SEQUENCE DESCRIPTION: SEQ ID NO:21:

TACCCAAATT ACTGACCCGG AAGTACTG     28

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS ( B ) LOCATION: 1..21

( x i ) SEQUENCE DESCRIPTION: SEQ ID NO:22:

ACTACTCCGC AGATGGGTTT A                                                                 21

( 2 ) INFORMATION FOR SEQ ID NO:23:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..29

( x i ) SEQUENCE DESCRIPTION: SEQ ID NO:23:

TTTCTGGTCT CGCGGGAGAC TCTTAAGAA                                                         29

( 2 ) INFORMATION FOR SEQ ID NO:24:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..28

( x i ) SEQUENCE DESCRIPTION: SEQ ID NO:24:

GAATTCTGTC ATGGGCTTCC AAAAGTTC                                                          28

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..30

( x i ) SEQUENCE DESCRIPTION: SEQ ID NO:25:

```
CTG  GAC  AGC  CCC  AGA  TCC  AAG  AGA  TCT  AGA                                        30
Leu  Asp  Ser  Pro  Arg  Ser  Lys  Arg  Ser  Arg
 1                   5                        10
```

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Leu  Asp  Ser  Pro  Arg  Ser  Lys  Arg  Ser  Arg
 1                   5                        10
```

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..30

( x i ) SEQUENCE DESCRIPTION: SEQ ID NO:27:

```
CTG  GAC  AGA  CCC  ATG  TCC  AAG  AGA  TCT  AGA              30
Leu  Asp  Arg  Pro  Met  Ser  Lys  Arg  Ser  Arg
 1               5                        10
```

( 2 ) INFORMATION FOR SEQ ID NO:28:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Leu  Asp  Arg  Pro  Met  Ser  Lys  Arg  Ser  Arg
 1               5                        10
```

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..30

( x i ) SEQUENCE DESCRIPTION: SEQ ID NO:29:

```
CTG  GAC  AGA  CCC  AGA  TCC  AAG  AGA  TCT  AGA              30
Leu  Asp  Arg  Pro  Arg  Ser  Lys  Arg  Ser  Arg
 1               5                        10
```

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Leu  Asp  Arg  Pro  Arg  Ser  Lys  Arg  Ser  Arg
 1               5                        10
```

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 1..30

( x i ) SEQUENCE DESCRIPTION: SEQ ID NO:31:

| CTG | GAC | AGC | CCC | ATG | TCC | AAG | AGA | TCT | AGA | 30 |
|-----|-----|-----|-----|-----|-----|-----|-----|-----|-----|----|
| Leu | Asp | Ser | Pro | Met | Ser | Lys | Arg | Ser | Arg | |
| 1 | | | | 5 | | | | | 10 | |

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| Leu | Asp | Ser | Pro | Met | Ser | Lys | Arg | Ser | Arg |
|-----|-----|-----|-----|-----|-----|-----|-----|-----|-----|
| 1 | | | | 5 | | | | | 10 |

( 2 ) INFORMATION FOR SEQ ID NO:33:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..25

( x i ) SEQUENCE DESCRIPTION: SEQ ID NO:33:

CTCTAGAGAC AAAACTCACA CATGC    25

( 2 ) INFORMATION FOR SEQ ID NO:34:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..28

( x i ) SEQUENCE DESCRIPTION: SEQ ID NO:34:

GGCGGCCGCC GCACTCATTT ACCCGGAG    28

( 2 ) INFORMATION FOR SEQ ID NO:35:

( i ) SEQUENCE CHARACTERISTICS:
        ( A ) LENGTH: 635 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: murine GIF ( i x ) FEATURE:
    ( A ) NAME/KEY: CDS
    ( B ) LOCATION: 82..426

( x i ) SEQUENCE DESCRIPTION: SEQ ID NO:35:

```
GGCACGACGT CAGGTCCCTG GCTTGGGTCA CACCGCGCTT TGTACCGTCC TCCGGTCCAC      60

GCTCGCAGTC TCTCCGCCAC C ATG CCT ATG TTC ATC GTG AAC ACC AAT GTT       111
                       Met Pro Met Phe Ile Val Asn Thr Asn Val
                        1           5                       10

CCC CGC GCC TCC GTG CCA GAG GGG TTT CTG TCG GAG CTC ACC CAG CAG       159
Pro Arg Ala Ser Val Pro Glu Gly Phe Leu Ser Glu Leu Thr Gln Gln
             15                  20                  25

CTG GCG CAG GCC ACC GGC AAG CCC GCA CAG TAC ATC GCA GTG CAC GTG       207
Leu Ala Gln Ala Thr Gly Lys Pro Ala Gln Tyr Ile Ala Val His Val
         30                  35                  40

GTC CCG GAC CAG CTC ATG ACT TTT AGC GGC ACG AAC GAT CCC TGC GCC       255
Val Pro Asp Gln Leu Met Thr Phe Ser Gly Thr Asn Asp Pro Cys Ala
     45                  50                  55

CTC TGC AGC CTG CAC AGC ATC GGC AAG ATC GGT GGT GCC CAG AAC CGC       303
Leu Cys Ser Leu His Ser Ile Gly Lys Ile Gly Gly Ala Gln Asn Arg
 60                  65                  70

AAC TAC AGT AAG CTG CTG TGT GGC CTG CTG TCC GAT CGC CTG CAC ATC       351
Asn Tyr Ser Lys Leu Leu Cys Gly Leu Leu Ser Asp Arg Leu His Ile
 75                  80                  85                  90

AGC CCG GAC CGG GTC TAC ATC AAC TAT TAC GAC ATG AAC GCT GCC AAC       399
Ser Pro Asp Arg Val Tyr Ile Asn Tyr Tyr Asp Met Asn Ala Ala Asn
                 95                 100                 105

GTG GGC TGG AAC GGT TCC ACC TTC GCT TGAGTCCTGG CCCCACTTAC             446
Val Gly Trp Asn Gly Ser Thr Phe Ala
            110                 115

CTGCACCGCT GTTCTTTGAG CCTCGCCTCT CCACGTAGTG TTCTGTGTTT ATCCACCGGT     506

AGCGATGCCC ACCTTCCAGC CGGGAGAAAT AAATGGTTTA TAAGAGACCA AAAAAAAAA      566

AAAAAAAAAA AAAAAAAAAA AAAAAAAAAA AAAAAAAAAA AAAAAAAAAA AAAAAAAAA      626

AAAAAAAAA                                                            635
```

( 2 ) INFORMATION FOR SEQ ID NO:36:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Met Pro Met Phe Ile Val Asn Thr Asn Val Pro Arg Ala Ser Val Pro
 1               5                  10                  15

Glu Gly Phe Leu Ser Glu Leu Thr Gln Gln Leu Ala Gln Ala Thr Gly
             20                  25                  30

Lys Pro Ala Gln Tyr Ile Ala Val His Val Val Pro Asp Gln Leu Met
         35                  40                  45

Thr Phe Ser Gly Thr Asn Asp Pro Cys Ala Leu Cys Ser Leu His Ser
     50                  55                  60

Ile Gly Lys Ile Gly Gly Ala Gln Asn Arg Asn Tyr Ser Lys Leu Leu
 65                  70                  75                  80

Cys Gly Leu Leu Ser Asp Arg Leu His Ile Ser Pro Asp Arg Val Tyr
                 85                  90                  95

Ile Asn Tyr Tyr Asp Met Asn Ala Ala Asn Val Gly Trp Asn Gly Ser
                100                 105                 110
```

(2) INFORMATION FOR SEQ ID NO:37:

(i) SEQUENCE CHARACTERISTICS:
    (A) LENGTH: 557 base pairs
    (B) TYPE: nucleic acid
    (C) STRANDEDNESS: single
    (D) TOPOLOGY: linear (ii) MOLECULE TYPE: DNA (genomic)

(vii) IMMEDIATE SOURCE:
    (B) CLONE: human GIF cDNA (ix) FEATURE:
    (A) NAME/KEY: CDS
    (B) LOCATION: 75..419

(xi) SEQUENCE DESCRIPTION: SEQ ID NO:37:

```
CAGGCACGTA GCTCAGCGGC GGCGCGGCGC GTGCGTCTGT GCCTCTGCGC GGGTCTCCTG          60

GTCCTTCTGC CATC ATG CCG ATG TTC ATC GTA AAC ACC AAC GTG CCC CGC          110
              Met Pro Met Phe Ile Val Asn Thr Asn Val Pro Arg
                1               5                      10

GCC TCC GTG CCG GAC GGG TTC CTC TCC GAG CTC ACC CAG CAG CTG GCG          158
Ala Ser Val Pro Asp Gly Phe Leu Ser Glu Leu Thr Gln Gln Leu Ala
            15                  20                  25

CAG GCC ACC GGC AAG CCC CCC CAG TAC ATC GCG GTG CAC GTG GTC CCG          206
Gln Ala Thr Gly Lys Pro Pro Gln Tyr Ile Ala Val His Val Val Pro
        30                  35                  40

GAC CAG CTC ATG GCC TTC GGC GGC TCC AGC GAG CCG TGC GCG CTC TGC          254
Asp Gln Leu Met Ala Phe Gly Gly Ser Ser Glu Pro Cys Ala Leu Cys
45                  50                  55                  60

AGC CTG CAC AGC ATC GGC AAG ATC GGC GGC GCG CAG AAC CGC TCC TAC          302
Ser Leu His Ser Ile Gly Lys Ile Gly Gly Ala Gln Asn Arg Ser Tyr
                65                  70                  75

AGC AAG CTG CTG TGC GGC CTG CTG GCC GAG CGC CTG CGC ATC AGC CCG          350
Ser Lys Leu Leu Cys Gly Leu Leu Ala Glu Arg Leu Arg Ile Ser Pro
            80                  85                  90

GAC AGG GTC TAC ATC AAC TAT TAC GAC ATG AAC GCG GCC AAT GTG GGC          398
Asp Arg Val Tyr Ile Asn Tyr Tyr Asp Met Asn Ala Ala Asn Val Gly
        95                  100                 105

TGG AAC AAC TCC ACC TTC GCC TAAGAGCCGC AGGGACCCAC GCTGTCTGCG             449
Trp Asn Asn Ser Thr Phe Ala
110                 115

CTGGCTCCAC CCGGGAACCC GCCGCACGCT GTGTTCTAGG CCCGCCCACC CCAACCTTCT        509

GGTGGGGAGA AATAAACGGT TTAGAGACTA AAAAAAAAA AAAAAAA                       557
```

(2) INFORMATION FOR SEQ ID NO:38:

(i) SEQUENCE CHARACTERISTICS:
    (A) LENGTH: 115 amino acids
    (B) TYPE: amino acid
    (D) TOPOLOGY: linear (ii) MOLECULE TYPE: protein (xi) SEQUENCE DESCRIPTION: SEQ ID NO:38:

```
Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30
```

-continued

| | | | | | | | | | | | | | | | |
|---|---|---|---|---|---|---|---|---|---|---|---|---|---|---|---|
| Lys | Pro | Pro | Gln | Tyr | Ile | Ala | Val | His | Val | Val | Pro | Asp | Gln | Leu | Met |
| | | 35 | | | | | 40 | | | | | 45 | | | |
| Ala | Phe | Gly | Gly | Ser | Ser | Glu | Pro | Cys | Ala | Leu | Cys | Ser | Leu | His | Ser |
| | 50 | | | | | 55 | | | | | 60 | | | | |
| Ile | Gly | Lys | Ile | Gly | Gly | Ala | Gln | Asn | Arg | Ser | Tyr | Ser | Lys | Leu | Leu |
| 65 | | | | | 70 | | | | | 75 | | | | | 80 |
| Cys | Gly | Leu | Leu | Ala | Glu | Arg | Leu | Arg | Ile | Ser | Pro | Asp | Arg | Val | Tyr |
| | | | | 85 | | | | | 90 | | | | | 95 | |
| Ile | Asn | Tyr | Tyr | Asp | Met | Asn | Ala | Ala | Asn | Val | Gly | Trp | Asn | Asn | Ser |
| | | | 100 | | | | | 105 | | | | | 110 | | |
| Thr | Phe | Ala | | | | | | | | | | | | | |
| | | 115 | | | | | | | | | | | | | |